(12) United States Patent
Jones

(10) Patent No.: US 8,372,966 B2
(45) Date of Patent: Feb. 12, 2013

(54) OLIGONUCLEOTIDE DECOYS AND METHODS OF USE

(75) Inventor: Walter Keith Jones, Ft. Thomas, KY (US)

(73) Assignee: University of Cincinnati, Cincinnati, OH (US)

( * ) Notice: Subject to any disclaimer, the term of this patent is extended or adjusted under 35 U.S.C. 154(b) by 772 days.

(21) Appl. No.: 10/596,516

(22) PCT Filed: Dec. 20, 2004

(86) PCT No.: PCT/US2004/042950
§ 371 (c)(1),
(2), (4) Date: Dec. 16, 2008

(87) PCT Pub. No.: WO2005/079217
PCT Pub. Date: Sep. 1, 2005

(65) Prior Publication Data
US 2009/0099108 A1    Apr. 16, 2009

Related U.S. Application Data

(60) Provisional application No. 60/531,399, filed on Dec. 19, 2003, provisional application No. 60/574,131, filed on May 25, 2004.

(51) Int. Cl.
*C07H 21/04*    (2006.01)
*C07H 21/02*    (2006.01)

(52) U.S. Cl. .................. 536/24.5; 536/24.1; 536/24.2; 536/23.1

(58) Field of Classification Search ............... 536/24.5, 536/24.1, 24.2, 23.1
See application file for complete search history.

(56) References Cited

U.S. PATENT DOCUMENTS

| | | | | |
|---|---|---|---|---|
| 6,774,118 | B1 * | 8/2004 | Dzau et al. ................ | 514/44 R |
| 2003/0186922 | A1 * | 10/2003 | Dzau et al. ................ | 514/44 |
| 2009/0105115 | A1 | 4/2009 | Reineke et al. | |
| 2009/0124534 | A1 | 5/2009 | Reineke et al. | |
| 2009/0203131 | A1 | 8/2009 | Reineke et al. | |
| 2011/0183417 | A1 | 7/2011 | Reineke et al. | |

FOREIGN PATENT DOCUMENTS

| | | |
|---|---|---|
| EP | 0824918 | 2/1998 |
| EP | 1362600 | 11/2008 |
| WO | 2005062854 | 7/2005 |
| WO | 2005084180 | 9/2005 |

OTHER PUBLICATIONS

Tomita et al., Potential therapeutic applications of decoy oligonucleotides. Curr Opin Mol Ther. 4(2):166-70, 2002.*
Weintraub et al. Retinoblastoma protein switches the E2F site from positive to negative element, Nature 358(6383):259-61, 1992.*
Sharma et al. Transcription factor decoy approach to decipher the role of NF-kappaB in oncogenesis, Anticancer Research, 16(1):61-69, 1996.*
Baeuerle et al, Function and Activation of NF-kB in the Immune System, Annu. Rev. Immuol. 1994, 12:141-179.
Higgins et al, Antisense inhibition of the p65 subunit of NF-kB blocks tumorigenicity and causes tumor regression, Proc. Natl. Acad. Sci. USA, 1993, 90:9901-9905.
Narayanan et al, Evidence for Differential Functions of the p50 and p65 Subunits of NF-kB with a Cell Adhesion Model, 1993, 13(6):3802-3810.
Sharma et al, Transcription Factor Decoy Approach to Decipher the Role of NF-kB in Oncogenesis, Anticancer Research 1996, 16:61-70.
Tanaka et al, Sequence-specific interaction of alpha-beta-anomeric double-stranded DNA with the p50 subunit of NFkB: application to the decoy approach, Nucleic Acids Research 1994, 22(15):3069-3074.
Tomita et al, Potential therapeutic applications of decoy oligonucleotides, Current Opinion in Molecular Therapeutics 2002, 4(2):166-170.
Weintraub et al, Retinoblastoma protein switches the E2F site from positive to negative element, Nature 1992, 358:259-261.

* cited by examiner

*Primary Examiner* — Wu-Cheng Winston Shen
(74) *Attorney, Agent, or Firm* — Dinsmore & Shohl LLP

(57) ABSTRACT

The present invention describes reagents and methods for using a concatemerized double-stranded oligonucleotide molecules (CODN) for transcription factor decoys. In one embodiment, the concatemers consist of a variable number of end-to-end repeated copies of a short (more than 5, 10, 15, 20, 2, 3035, 40, 45, 50, 75, 100, or more by but generally less than about 3 kb) dsDNA containing a sequence or sequences that act as transcription factor decoys. The present invention also provides for the use of the polymers for CODN/polymer complexes to a specific cell type; thus the agent can be made organ, tissue and/or cell-type specific. In another embodiment, the present invention provides for use of the CODN's in vitro or in vivo, in isolated cells or intact animals in which specific blockade of transcription factors or delivery of DNA or other biological effector is desirable. In one embodiment, this includes use as a research tool, including studies of specific genes and studies to identify specific genes regulated by the transcription factors targeted. In another embodiment, the present invention provides for using polyamides for NF-kB-specific CODN delivery in the treatment of myocardial ischemia/reperfusion and myocardial infarction, heart failure and hypertrophy, cardioprotection, stroke, neuroprotection, sepsis, arthritis, asthma, heritable inflammatory disorders, cancer, heritable immune dysfunctions, inflammatory processes, whether caused by disease or injury or infection, oxidative stress to any organ whether caused by disease, surgery or injury. The decoys may be any transcription factors, including, but not limited to, NF-kB, AP-I, ATF2, ATF3, SP 1 and others.

9 Claims, No Drawings

OLIGONUCLEOTIDE DECOYS AND METHODS OF USE

This application claims the benefit of U.S. Provisional Patent Application Ser. No. 60/531,399, filed Dec. 19, 2003 and U.S. Provisional Patent Application Ser. No. 60/574,131, filed May 25, 2004, which applications are hereby incorporated by reference in their entirety.

FIELD OF THE INVENTION

The present invention is in the fields of molecular biology, biochemistry and pharmaceuticals. In general, the invention provides compositions for the cellular delivery of nucleic acids, polypeptides and/or molecular complexes comprising nucleic acids and polypeptides, and methods of making and using such compositions. The present invention provides a new class of non-viral transduction vectors that can be used for both in vivo and in vitro applications. The present invention provides for unique polycationic polymers that can associate with many suitable bioactive molecules, including proteins and other compounds that poses multiple cationic sites. The polymer can act as a delivery vehicle for the associated bioactive molecule, in vivo or in vitro, to the cells of interest for the bioactive molecule. In one embodiment, the present invention provides for a new series of polyamides for use as gene delivery agents. Also disclosed are methods of using the polymers to bind products, e.g., oligonuclotides, and facilitate cellular uptake. In one embodiment, the invention provides for the in vitro delivery of plasmid DNA into cells. The present also provides for the use of these polymers for the delivery of a nucleic acid is biologically active into a cell.

BACKGROUND OF THE INVENTION

Nucleic acids show great promise as new therapeutics to treat both acquired and inherited diseases. One of the greatest challenges with the successful application of nucleic acid drugs is the development of an efficacious delivery method.1 Delivery systems are needed to compact genetic material into nanostructures that can be taken up by cells, protect nucleic acids from enzymatic damage during cellular transport, and provide the possibility of targeting the delivery to specific cell types.2 Viral vectors are still the most effective and commonly used method of DNA transport even though many problems with this delivery method have been revealed.2,3

Polymer-mediated gene delivery has recently emerged as a viable alternative to viral-based transduction systems since polymers may not induce immune and inflammatory responses, have a lower cost of synthesis, and have a large nucleic acid loading capacity.1,2 Several studies have shown that polycations bind DNA electrostatically and form polyplexes (polymer+DNA complexes) that are endocytosed by many cell types and deliver DNA with varying degrees of delivery efficiency and toxicity.4,5 Although synthetic delivery systems show great promise, difficulties with polymer toxicity and low delivery efficiency have hampered clinical application of these vectors.1,2 For example, polyethylenimine (PEI), a polymer of ethylenediamine, exhibits efficient gene delivery but is also very cytotoxic.6 Conversely, chitosan, a polymer of glucosamine, is completely nontoxic yet reveals low delivery efficiency in many cell lines.7 Progress towards rationally-designed synthetic delivery systems has also been stalled by a lack of understanding of the fundamental polymer structure-biological property relationships that exist for synthetic delivery vehicles.4,5

Drug delivery is an important field for both clinical applications and research. Some biological systems possess unique delivery challenges.

In recent years gene therapy has received a greater amount of attention in academic and scientific circles. The potential for gene therapy for pharmaceutical, commercial, and clinical applications is tremendous. Gene transfection, the addition of a gene to a cell, is a critical component of gene therapy.

Presently there are several approaches to gene transfection. These include the use of viral based vectors (e.g., retroviruses, adenoviruses, and adeno-associated viruses) (Drumm, M. L. et al., *Cell* 62:1227-1233 (1990); Rosenfeld, M. A. et al., *Cell* 68:143-155 (1992); and Muzyczka, N., *Curr. Top. Micro. Immuno.* 158:97-129 (1992)), charge associating the DNA with an asialorosomucoid/poly L-lysine complex (Wilson, J. M. et al., (1992)), Charge associating the DNA with cationic liposomes (Brigham, K. L. et al., (1993)) and the use of cationic liposomes in association with a poly-L-lysine antibody complex (Trubetskoy, V. S. et al., *Biochem. Biophys. Acta* 1131:311-313 (1993)).

Viral vectors have exhibited the highest levels of transfection efficiency to date for nucleic acids. Viral vectors have been particularly effective in in vivo systems, where other transfection systems have fallen short. Viral vectors do have a tremendous downside, namely the potential to illicit a potentially life-threatening immune response. (Kingman, *Bioworld Int.*, 1(20):1 (1996)). This happens because the viral carrier actually infects the cell as part of the method of transfection.

Although non-viral based transfection systems have not exhibited the efficiency of viral vectors, they are still receiving significant scientific attention because of their probable increased safety for in vivo systems. This has also led to increased attention for in vitro systems as well. Synthetic cationic molecules have been reported to "coat" the nucleic acid through interactions on the cationic sites of the transfection reagent and the anionic sites on the nucleic acid. The positively charged coating reportedly interacts with the negatively charged cell membrane to facilitate the passage of the nucleic acid into the cytoplasm via non-specific endocytosis. (Schofield, *Brit. Microencapsulated. Bull.*, 51(1):56-71 (1995)).

Past attempts at nucleic acid transfection have also experienced difficulty with DNA precipitating out of solution. The problem is especially acute in in vivo applications where typically higher concentrations of DNA are present. These higher concentrations create solubility problems for the DNA/carrier systems. DNA precipitation can be avoided by increasing the concentration of mono- and polyvalent cations. In the past this had partly solved the DNA solubility problem, but it also increased the toxic effects upon the transfected cells.

SUMMARY OF THE INVENTION

The present invention provides a new class of non-viral transduction vectors that can be used for both in vivo and in vitro applications. In particular, these vectors can be used for gene transfer applications. These new gene transduction vectors can achieve transfer efficiencies far greater to commercially available polymeric and liposomal gene transfer vectors while maintaining little or no toxicity in vitro. Their low in vitro toxicity makes them ideal candidates for in vivo use. The present invention also provides a gene transfer vector that has comparable efficiency to a viral vector without the potential for a life-threatening immune response.

Furthermore, the unique polycationic structure of these polymers associates with many suitable biologically active molecule, including oligonucleotides and polypeptides and other compounds that poses multiple cationic sites. The polymer can act as a delivery vehicle for the associated biologically active molecule, in vivo or in vitro, to the cells of interest for the biologically active molecule.

In one embodiment, the invention encompasses a method of delivering a biologically active molecule to a cell, comprising contacting the cell with (a) a biologically active molecule and (b) a cellular delivery polymer.

In one embodiment, the present invention also provides for compositions and non-covalent complexes comprising one or more polymers of the present invention, e.g., polyamides, dendritic macromolecules (polymers comprising an oligoamine shell and a cyclodextrin core), and carbohydrate-containing degradable polyesters, and at least one nucleic acid molecule (e.g., one or more oligonucleotides) or at least one polypeptide or both. The invention also provides compositions comprising such complexes.

Complexes according to the invention or portions thereof, can comprise a cellular delivery molecule or agent that can facilitate the translocation of the complex or portion thereof into cells. In some embodiments, cellular delivery molecules for use in the present invention may comprise one or more one or more polymers of the present invention, e.g., polyamides, dendritic macromolecules (polymers comprising an oligoamine shell and a cyclodextrin core), and carbohydrate-containing degradable polyesters.

In some embodiments, a cell, tissue, organ or organism may be contacted with a complex of the invention. Preferably, the complex is taken up by the cell or by one or more cells of the tissue, organ or organism.

In another exemplary and non-limiting embodiment of the invention, compositions comprising complexes between cellular delivery polymers and oligonucleotides are formed and can be applied to cultured mammalian cells. The complex may also comprise a combination of labeled and nonlabeled nucleic acid and or peptide. These complexes allow mediation of an activity associated with the oligonucleotide, which, by way of non-limiting example, can be a gene-containing oligonucleotide, an antisense oligonucleotide, an aptamer, a short interfering RNA (siRNA), a short hairpin RNA (shRNA), a small temporally regulated RNA (stRNA), and the like. In some embodiments, oligonucleotides are preferred.

In other specific embodiments, the biologically active molecule and/or cell delivery agent is covalently labeled with a fluorophores (fluorescent moiety), for example with fluorescein or a derivative of fluorescein.

In another embodiment, the compositions may comprise one or more fluorescent molecules or moieties, which may be the same or different, and may be covalently attached to one or more polypeptides and/or nucleic acid molecules in the complexes of the invention. Alternatively, or in addition, complexes of the invention may comprise one or more "free" fluorescent molecule (i.e., one or more fluorescent molecules that are not covalently attached to either the polypeptide or the oligonucleotide but may still be associated with the complex). One or more of the compounds of the compositions or complexes can be a biologically active molecule.

Kits according to the invention may further comprise one or more transfection agents, one or more cells, one or more nucleic acids, one or more set of instructions, and one or more biologically active molecules.

Other additional kit components include without limitation: additional nucleic acids, such as oligonucleotides, iRNA molecules, plasmids, etc.; one or more recombinases, including without limitation site-specific recombinases; one or more recombination proteins; and/or one or more cells. In some embodiments, the cells are competent for transfection or transformation.

In other embodiments, the invention provides a complex comprising a cell delivery polymer and a biologically active agent that is desirably taken up by cells, wherein the cell delivery polymer or biologically active agent comprises a fluorescent moiety.

The nucleic acid of the complexes and other embodiments of the invention can comprise from 5 bases to about 200 kilobases. Any type of nucleic acid may be used, including by way of non-limiting example mRNA, tmRNA, tRNA, rRNA, siRNA, shRNA, PNA, ssRNA, dsRNA, ssDNA, dsDNA, DNA:RNA hybrid molecules, plasmids, artificial chromosomes, gene therapy constructs, cDNA, PCR products, restriction fragments, ribozymes, antisense constructs, and combinations thereof. Reviews of tmRNA include Muto A, Ushida C, Himeno H. A bacterial RNA that functions as both a tRNA and an mRNA. Trends Biochem Sci. 1998 January; 23(1):25-9; and Withey J H, Friedman D I. The biological roles of trans-translation. Curr Opin Microbiol. 2002 April; 5(2): 154-9). The nucleic acid may comprise one or more chemical modifications.

A complex according to the invention may further comprise one or more transfection agents, one or more recombinases and, additionally or alternatively, one or more recombination proteins.

A nucleic acid used in the invention includes, in some embodiments, a sequence that encodes a protein or a portion thereof. In some embodiments, a cellular nucleic acid encoding the protein, or a portion thereof, is desirably replaced by the sequence in one form of gene therapy. Additionally or alternatively, the protein is expressed in the cell. The protein may be exogenous or endogenous. In the latter case, the cells to be transfected may comprise a non-functional form of the protein.

A composition of the invention may be a pharmaceutical composition. In certain embodiments, the biologically active molecule is one or more of the nucleic acids that has a biological activity, including but not limited to therapeutic activity. By way of non-limiting example, biologically active nucleic acids are selected from the group consisting of mRNA, tmRNA, tRNA, rRNA, siRNA, shRNA, PNA, ssRNA, dsRNA, ssDNA, dsDNA, DNA:RNA hybrid molecules, plasmids, artificial chromosomes, gene therapy constructs, cDNA, PCR products, restriction fragments, ribozymes, antisense constructs, and combinations thereof.

Additionally or alternatively, polypeptide of the complex is biologically active. A biologically active polypeptide may be a therapeutic protein. By way of non-limiting example, bioactive proteins include antibodies or antibody fragments, hormones, enzymes, transcription factors, growth factors, and the like.

The invention further provides a method of providing gene therapy to an individual in need thereof, of treating an individual suffering from a disease or disorder, the method comprising contacting the individual, or cells therefrom, with one or more complexes, compositions and/or pharmaceutical compositions of the invention.

The invention further provides a method of testing a cellular response to a test compound, the method comprising: (a) contacting a first cell with, in any order or combination, a biologically active molecule and a cellular delivery molecule; (b) contacting a second cell with, in any order or combination, a second biologically active molecule and the cellular delivery molecule; (c) contacting the cells with the test compound, before (a); during (a) or (b); between (a) and (b); and, additionally or alternatively, after (b); (d) measuring and comparing at least one parameter of from the first cell with the signal from the second cell. In certain embodiments, one or more of the cells comprise one or more reporter genes that generate a detectable signal or interfere with the production of a detectable signal.

In one embodiment, the present invention provides for a new series of polyamides for use as gene delivery agents. These polymers bind products, e.g., oligonucliotides, and facilitate cellular uptake. In one embodiment, the invention provides for the in vitro delivery of plasmid DNA into cells. In one embodiment, the invention provides for the in vivo delivery of plasmid DNA into cells.

In one embodiment, the present invention relates to the use of polyamides for delivering nucleic acids into a cell. In one embodiment, the nucleic acid is an oligonucleotide. In another embodiment, the oligonucleotide contains from about 10 to about 1000 nucleotides. In another embodiment, the oligonucleotide is an antisense oligonucleotide or oligodeoxynucleotide. In another embodiment, the oligonucleotideis an oligonucleotide, an antisense oligonucleotide residue or oligodeoxynucleotide residue.

In another embodiment, the nucleic acid is selected from the group consisting of antisense constructs, antisense polynucleotide, artificial chromosomes, cDNA, concatemers, concatemeric decoy oligonucleotides, CpG oligomers, cyclic oligonucleotides, decoy oligonucleotides, DNA:RNA hybrid molecules, dsDNA, dsRNA, gene therapy constructs, LNA, morpholinos, mRNA, oligonucleotides and oligodeoxynucleotides with phosphorodiester backbones or phosphorothioate backbones, PCR products, plasmids, PNA, restriction fragments, ribozyme, RNA, RNAi, RNAi inducing polynucleotide, rRNA, shRNA, siRNA, spiegelners, ssDNA, ssRNA, trRNA, transgenes, tricyclo-DNA, triple helices, tRNA, and combinations thereof.

In another embodiment, the present invention provides for the use for polyamides to deliver a concatemer to a cell. In another embodiment, the present invention provides for the use for polyamides to deliver a concatemerized double-stranded oligonucleotide molecules (CODN) for transcription factor decoys. In one embodiment, the concatemers consist of a variable number of end-to-end repeated copies of a short (more than 5, 10, 15, 20, 2, 3035, 40, 45, 50, 75, 100, or more bp but generally less than about 3 kb) dsDNA containing a sequence or sequences that act as transcription factor decoys.

The use of the concatemers provides one or more of the following benefits: a) increased half-life of the nucleotide within the cell; b) increased efficacy of each single molecule, since each contains multiple copies of the specific decoy; c) the molar amount of decoy can be titrated to achieve a specific degree of transcription factor blockade; d) CODNs can be designed to block subsets of transcription factor binding sites that may underlie biological variation in transcription factor response; e) a combinatorial blockade, since each CODN can bind multiple transcription factors, where use of concatemers allows for delivery of decoys for 2 or more transcription factors to be done in a precisely controlled manner. This latter point is relevant to two important issues. First, to any use requiring titration of transcription factor blockade, especially of one transcription factor relative to another. For instance, if one wishes to completely block factor X and block factor Y only 25%, this can be done by empirically determining the ratio of the decoy for X and Y required and assembling the CODN to this requirement. Second, to the fact that transcription factors often act together to activate discrete subsets of genes. For instance, NF-kB and AP-1 each act primarily on a certain subset of promoters. There is however, a common subset that requires the cooperative binding of both transcription factors to nearby sites on the promoter to properly activate gene expression. The concatemer allows blocking of these genes with relative specificity by titrating the decoys for the two transcription factors, or by designing a unique CODN to the specific combination of NP-kB and AP-1 binding sites found in the specific promoter.

In another embodiment, the present invention provides for the use of the polymers for covalent addition of targeting peptides, receptor binding peptides/protein domains and antibody fragments that may be used to target the CODN/polymer complexes to a specific cell type; thus the agent can be made organ, tissue and/or cell-type specific.

In another embodiment, the present invention provides for using polyamides for targeting peptides and/or antibodies for specific stress and/or drug induced cellular receptors. In one embodiment, the polyamides target the CODN/polymer complexes to ischemic, inflamed or cancerous tissues.

In another embodiment, the present invention provides for using linker peptides containing the sequence recognized by the TNF-alpha converting enzyme (TACE) or another exopeptidase or endopeptidase in order to allow the agent to deliver the CODN/polymer complex to the cell and then cleave off the targeting peptide.

In another embodiment, the present invention provides for using the polyamides to deliver intact genes (transgenes), plasmids, RNAi, siRNA, morpholinos or other kinds of RNA, proteins and polynucleotides. In one embodiment, the genes incorporate tissue-specific promoters, controllable promoters, promoters that may be silenced by specific CODN/polymer combinations and may constitute two- and three-unit systems for gene expression, control and DNA transposition (i.e. insertion, excision and targeting of transgenes and other DNA molecules).

In another embodiment, the present invention provides for use of the polyamides in vitro or in vivo, in isolated cells or intact animals in which specific blockade of transcription factors or delivery of DNA or other biological effector is desirable. In one embodiment, this includes use as a research tool, including studies of specific genes and studies to identify specific genes regulated by the transcription factors targeted (relates to development of specific CODN/polymer complexes and related gene marker mouse lines described below). For clinical use, this would include, but is not limited to delivery of transcription factor decoys (e.g. CODNs) that block transcription factors implicated in disease, response to surgery and/or trauma, developmental defects, aging, toxic exposure, etc.

In another embodiment, the present invention provides for using polyamides for NF-kB-specific CODN delivery in the treatment of myocardial ischemia/reperfusion and myocardial infarction, heart failure and hypertrophy, cardioprotection, stroke, neuroprotection, sepsis, arthritis, asthma, heritable inflammatory disorders, cancer, heritable immune dysfunctions, inflammatory processes, whether caused by disease or injury or infection, oxidative stress to any organ whether caused by disease, surgery or injury. In another embodiment, the present invention provides for using polyamides for delivery of CODN/polymer complexes to delineate in animal models, specific situations in which NF-kB or other transcription factors contribute to injury, dysfunction, morbidity or mortality, determine whether blockade is beneficial in animals and then translating this to the clinic.

In another embodiment, the present invention provides for transgenic mice expressing marker genes (lacZ and/or GFP variants) under the control of promoter elements that are primarily controlled by specific transcription factors. In one embodiment, the mice are provided separately or as a kit including specific CODN/polymer complexes and the matching mouse, which serves to identify the cells in which the marker activation (experimentally activated) is blocked by the CODN. In another embodiment, there are transgenic mice with marker genes that are transcriptionally turned on, which can be specifically turned off using CODN/polymer complexes.

In another embodiment, the present invention provides for bi-transgenic (or multiple transgenic) systems designed to utilize the CODN/polymer complexes to regulate gene expression (up, down, on or off) or to mediate gene transposition (insertion, excision or moving in the genome). In one embodiment, transgene A may express a gene of interest under control of a promoter that is inducible by NF-kB or by a yeast or bacterial transcription factor (think tetR or Gal4). In one embodiment, the gene would be on after an NF-kB-inducing stimulus, or constitutively on in a tissue expressing the specific transcription factor (we are making mice for NF-kB activation; mice for gal4 and tetR already exist) and the gene could be turned off by simply providing the CODN/polymer complexes for the specific transcription factor (CODN-OFF). In another embodiment, the animals are continuously delivered CODN/polymer complexes and then the CODN/polymer complexes is withdrawn to turn the gene on. Other versions could have the gene off, due to expression in the same cells of a transcriptional repressor (has been described for tet), and the repression reversed by adding CODN/polymer complexes, allowing expression to turn on (CODN-ON).

Another embodiment provides for the delivery of transgenes that may be incorporated into the genome via retroviruses, transposons or retrotransposons. In one embodiment, the delivery is for long-term gene expression or genetic engineering in vitro, in vivo, in isolated cells or in whole animals or in the clinic. In another embodiment, germ cells are targeted using compositions of the present invention to achieve heritable transgenic lines of animals without having to do microinjection (optionally using a bi-transgenic system).

In another embodiment, the present invention provides for polymers designed for variable release/biodegradation; some may be designed, selected for quick degradation/release of CODN, others for long half-life (the CODN may be active whether or not it is released by the polymers, so we should safeguard the concept that long-lasting binding of the DNA by polymers, may be a way to prolong activity).

In another embodiment, the present invention provides for the delivery of one or more imaging agents for real-time and still imaging within a cell or tissue.

In another embodiment, the present invention provides for using polyamides for delivery of transcription factor decoys (including, but not limited to NF-kB), to block signaling and gene expression associated with pathogenesis.

In another embodiment, the present invention provides for using polyamides for delivery of linear duplications or chains of these decoys (i.e., concatemers), such that each strand contains a number of decoy transcription factor binding sites including more than 1, 2, 3, 4, 5, 6, 7, 8, 9, 10, 15, 20, 25, 39 or more. In another embodiment, the present invention provides for using polyamides for delivery of decoys having for multiple transcription factors into one of these strands, such that it can affect blockade of 2, 3, 4, 5, 6, or more transcription factors simultaneously in a cell. In another embodiment, the present invention provides for using polyamides for delivery of these strands, or the strands contained in a plasmid or other DNA vector (can include phage, viral or other DNA) to bind to the polymers to deliver the strands to the cytoplasm of the cell, to effect transcription factor blockade.

The decoys may be any transcription factors, including, but not limited to, NF-kB, AP-1, ATF2, ATF3, SP1 and others. This is all based on the novel concept, supported by data in our lab, that blocking key signaling molecules simultaneously can have additive or even synergistic therapeutic effects, particularly when the molecules chosen are key signaling hubs. In signaling, transcription factors participate by activating or turning down gene expression. In another embodiment, the present invention provides for using polyamides for treatment of MI by blocking NF-kB using decoys to iNOS and Cox2. In another embodiment, the present invention provides for using polyamides for delivery of decoys to metallothionein and heat shock protein 70.

Other features and advantages of the invention will be apparent from the following detailed description and claims.

DETAILED DESCRIPTION OF THE INVENTION

Polymeric materials are described for the delivery of therapeutic DNA. The use of synthetic delivery agents has many advantages over viral delivery vectors for several reasons such as they may not induce immune and inflammatory responses and thus can be used repeatedly in clinical administration. In addition, synthetic vectors have a lower cost, are easier to manufacture on a larger scale, and they have the ability to carry an unlimited amount of genetic information.

Polycations self assemble with DNA through electrostatic interactions and compact DNA into small complexes that have been termed polyplexes. The formation of polyplexes usually occurs at a N/P ratio [the ratio of polymer nitrogens (N)/phosphate groups (P) on DNA] greater than one. Polyplexes can be taken up by cells through the endocytotic pathway. Without wishing to be limited by theory in any way, it is believed that after uptake, some of the polyplexes are able to escape the endosomes and are transported into the nucleus (most likely during cell division) where the delivered gene is transcribed. The polyamides of the present invention are created from comonomers (x=1, L-tartrate and x=2, galactarate).

In one embodiment, the present invention provides for a series of polymers for use to probe the structure-property relationships for synthetic vectors. Described are a series of polyamides that vary in the amount of the hydroxyl and secondary amine groups along the polymeric backbone.

In addition, we have systematically increased the number of secondary amines between the carbohydrates, in order to elucidate how the number of basic groups within a polymer repeat unit facilitates efficient nucleic acid binding, condensation, and intracellular gene delivery. To this end, we have selected a series of co-monomers that has allowed us to design in these chemical characteristics to yield both biotolerable (i.e, a nontoxic) and highly efficient delivery vehicle.

Polycations self-assemble with biologically active, molecules, and in particular nucleic acids and peptides, through electrostatic interactions and they compact DNA into small complexes that have been termed polyplexes. This has previously been disclosed in U.S. Pat. No. 5,948,878, Burgess et al., which is herein incorporated by reference in its entirety. The formation of the polyplexes usually occurs at a N/P ratio [the ratio of polymer nitrogens (N) to phosphate groups (P) and the DNA] greater than one. Polyplexes can be taken be taken up by the cell by through the endocytic pathway. After endocytosis the polyplexes are able to escape the endosomes and are able to enter the nucleus where the delivered gene is transcribed and translated into the desired protein. The polymers can be used to deliver any type, length, sequence, and shape of nucleic acid to any cellular destination.

The polymer structure plays a large role in the binding affinity of DNA and the compaction of DNA into polyplexes. Also, the polymer chemistry dictates the efficiency of polyplex cellular uptake and endosomal release within the cytoplasm. Furthermore, the polymer structure has been shown to significantly affect both the delivery efficiency and toxicity that is observed during gene transport.

The Classes of Polymers

Note: The term "polymers" is used throughout the application and this refers to the classes of polymers used for polyplex formation. Therefore, the term polymer includes poly(hydroxylamidoamine), dendritic macromolecules, and also carbohydrate-containing biodegradable polyesters.

1) Poly(hydroxylamidoamine)s

These polyamides, including but not limited to poly(glycoamidoamine)s, (any carbohydrate) and poly(L-tartaramidoamine)s, may be prepared by condensation of an appropriately substituted diester or other substitutions that react with amines such as acid chlorides, carboxylic acids, lactones, anhydrides, etc. and an appropriately substituted diamine comonomer.

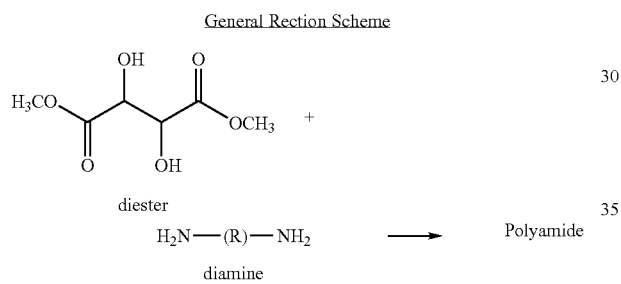

Diesters include, but are not limited to, those shown below, their stereoisomers, mixtures of isomers, and also include D-Mannaro-1,4-:6,3-dilactone, dimethyl-meso-galctarate, esterified glucaric acid, dimethyl D-glucarate (linear and closed ring forms of all stereoisomers), esters of methyl citric acid, methyltartronic acid, methyl D-arabinaric acid, and esters of xylaric acid and methyl heptaric acid.

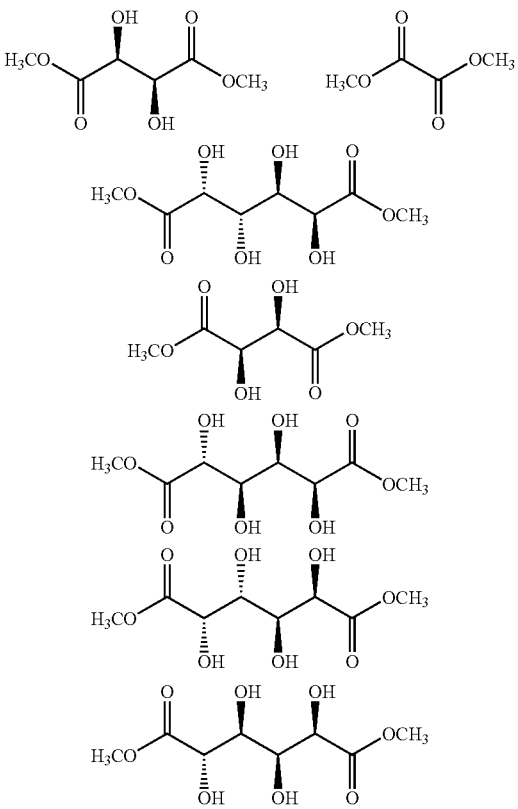

Examples of suitable diesters

Suitable diamines include but are not limited to those given in the formula below, where R may be an alkyl chain incorporating an variety of functional groups including ketones, amines, esters, alcohols, ethers, thiols, thioesters, phosphates, phosphonates. The R group is preferably are alkyl polyamine chain of varying lengths, with examples given in Table 1.

TABLE 1

| Diamine: NH$_2$—R—NH$_2$; | where R may be: |
|---|---|
| | —(CH$_2$)$_2$—NH—(CH$_2$)$_2$—; |
| | —(CH$_2$)$_2$—NH—(CH$_2$)$_2$—NH—(CH$_2$)$_2$—; |
| | —(CH$_2$)$_2$—NH—(CH$_2$)$_2$—NH—(CH$_2$)$_2$—NH—(CH$_2$)$_2$—; |
| | —(CH$_2$)$_2$—NH—(CH$_2$)$_2$—NH—(CH$_2$)$_2$—NH—(CH$_2$)$_2$—NH(CH$_2$)$_2$; |

An example of one class of polyamides of the present invention includes those shown below (x=0-10; n=1-infinity). This also includes all possible isomers, diastereomers and enantiomers, linear and branched forms.

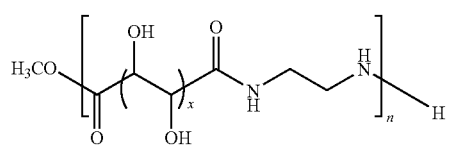

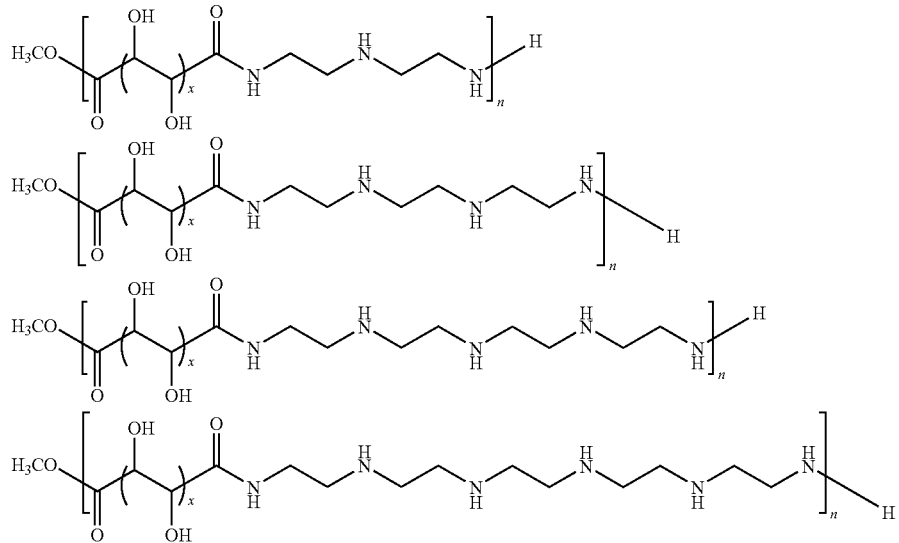

Preparation of poly(glycoamidoamine)s

The poly(glycoamidoamine)s are prepared by polycondensation of a diamine [such as diethylenetriamine, triethylenetetramine, tetraethylenepentamine, or pentaethylenehexamine] with a diester or dilactone carbohydrate derivative. After polymerization, each polymer product is dissolved in ultra pure water, dialyzed for 24 hours, and lyophilized to dryness. Examples of poly(glycoamidoamine)s which may be prepared by this process are shown below:

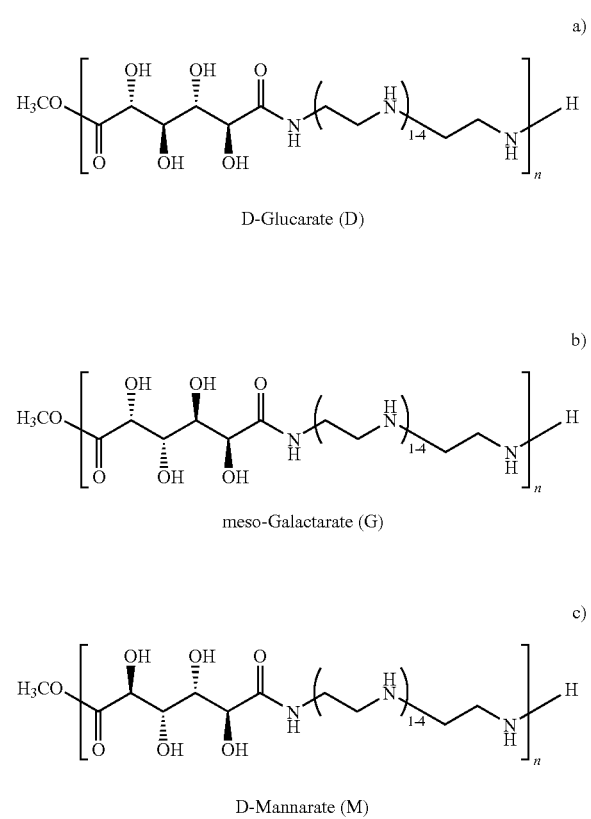

Preparation of poly(L-tartaramidoamine)s

Each polymer is synthesized through condensation polymerization of an amine comonomer (AA) with dimethyl L-tartarate (BB) in methanol at room temperature to yield a series of AABBAABB copolymers. All products obtained are of a white color.

Poly(L-tartaramidodiethyleneamine) (T1, see below): Diethylenetriamine (0.29 g, 2.80 mmol) is added to a methanol solution (2.80 mL) of dimethyl L-tartarate (0.50 g, 2.80 mmol) and stirred for 24 hours at room temperature. The mixture is dialyzed against ultra pure water to remove monomer, oligomer, and solvent impurities. Yield: 0.38 g, 1.75 mmol (62.5%). $^1$H NMR (D$_2$O): δ 4.46 (s, 2H), 3.31 (broad, 4H), 2.69 (broad, 4H).

Poly(L-tartaramidotriethylenediamine) T2, see below): Triethylenetetramine hydrate (containing 20.42% H$_2$O, 0.41 g, 2.81 mmol) is added and stirred in a methanol solution (2.80 mL) containing dimethyl L-tartarate (0.50 g, 2.80 mmol). After 24 hours, the mixture is dialyzed against ultra pure water. Yield: 0.60 g, 2.31 mmol (82.5%). $^1$H NMR (D$_2$O): δ 4.46 (s, 2H), 3.30 (broad, 4H), 2.68 (broad, 8H).

Poly(L-tartaramidotetraethylenetriamine) (T3, see below): Dimethyl L-tartarate (0.50 g, 2.80 mmol) is added to a methanol solution (10.0 mL) containing triethylamine (1.4 g, 14 mmol) and tetraethylenepentamine pentahydrochloride (1.04 g, 2.80 mmol). After 80 hours, the mixture is dialyzed against ultra pure water. Yield: 0.72 g, 2.38 mmol (84.8%). $^1$H NMR (D$_2$O): δ 4.45 (s, 2H), 3.31 (broad, 4H), 2.70 (broad, 12H).

Poly(L-tartaramidopentaethylenetetramine) (T4, see below): Dimethyl L-tartarate (0.50 g, 2.80 mmol) is added to a methanol solution (10.0 mL) of triethylamine (1.7 g, 17 mmol) and pentaethylenehexamine hexahydrochloride (1.26 g, 2.80 mmol). After 8 hours, the mixture is dialyzed against ultra pure water. Yield: 0.50 g, 1.44 mmol (51.4%). $^1$H NMR (D$_2$O): δ 4.45 (s, 2H), 3.31 (broad, 4H), 2.71 (broad, 16H).

Examples of the poly(L-tartaramidoamine)s are shown below:

The new poly(L-tartaramidoamine)s T1–T4.

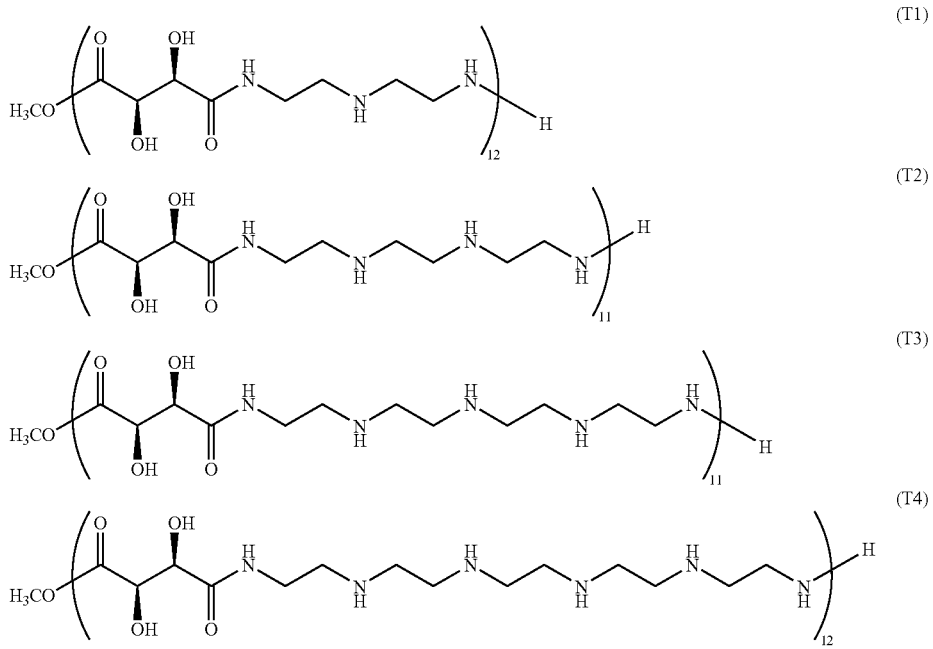

Preparation of poly(D-glucaramidoamine)s

Polymerization. Each polymer is synthesized through condensation polymerization of an amine comonomer with esterified D-glucaric acid in methanol at room temperature. All products obtained are of a white color.

Poly(D-glucaramidodiethyleneamine) (1, see below): Diethylenetriamine (0.09 g, 0.87 mmol) is added to a methanol solution (8.40 mL) of esterified D-glucaric acid (0.20 g, 0.84 mmol). The clear solution becomes cloudy after approximately 10-15 min while stirring at room temperature. After 48 hours, the polymerization mixture is dissolved in and dialyzed against ultra pure water to purity. Yield: 0.22 g, 0.79 mmol, 91.2%. $^1$H NMR (DMSO-$d_6$): δ 7.86 (s, 1H), 7.69 (s, 1H), 4.02 (d, 1H), 3.96 (d, 1H), 3.88 (t, 1H), 3.72 (t, 1H), 3.17 (s, 4H), 2.58 (s, 4H).

Poly(D-glucaramidotriethylenediamine) (2, see below):
Triethylenetetramine hydrate (containing 20.42% $H_2O$, 0.15 g, 0.82 mmol) is added to a methanol solution (8.40 mL) of esterified D-glucaric acid (0.20 g, 0.84 mmol). The clear solution becomes cloudy after approximately 10-15 min while stirring at room temperature. After 48 hours, the polymerization mixture is dissolved in and dialyzed against ultra pure water to purity. Yield: 0.18 g, 0.56 mmol, 68.6%. $_1$H NMR (DMSO-$d_6$): δ 7.89 (s, 1H), 7.70 (s, 1H), 4.05 (d, 1H), 3.97 (d, 1H), 3.89 (t, 1H), 3.73 (t, 1H), 3.20 (s, 4H), 2.60 (s, 8H).

Poly(D-glucaramidotetraethylenetriamine) (3, see below): Esterified D-glucaric acid (0.20 g, 0.84 mmol) is added to a methanol solution (8.40 mL) of triethylamine (0.42 g, 4.15 mmol) and tetraethylenepentamine pentahydrochloride (0.31 g, 0.83 mmol). The clear solution becomes cloudy after approximately 30 min while stirring at room temperature. After 6 hours, the polymerization mixture is dissolved in and dialyzed against ultra pure water to purity. Yield: 0.11 g, 0.30 mmol, 36.0%. $_1$H NMR (DMSO-$d_6$): δ 7.90 (s, 1H), 7.70 (s, 1H), 4.02 (d, 1H), 3.96 (d, 1H), 3.88 (t, 1H), 3.73 (t, 1H), 3.19 (s, 4H), 2.60 (s, 12H).

Poly(D-glucaramidopentaethylenetetramine) (4, see below): Esterified D glucaric acid (0.20 g, 0.84 mmol) is added to a methanol solution (5.60 mL) of triethylamine (0.51 g, 5.04 mmol) and pentaethylenehexamine hexahydrochloride (0.38 g, 0.84 mmol). The clear solution becomes cloudy after approximately 30 min while stirring at room temperature. After 8 hours, the polymerization mixture is dissolved in and dialyzed against ultra pure water to purity. Yield: 0.15 g, 0.37 mmol, 44.0%. $_1$H NMR (DMSO-$d_6$): δ 7.87 (s, 1H), 7.72 (s, 1H), 4.02 (d, 1 µl), 3.94 (d, 1H), 3.87 (t, 1H), 3.71 (t, 1H), 3.16 (s, 4H), 2.59 (s, 14H), 2.22 (s, 2H).

Examples of poly(D-glucaramidoamine)s are shown below:

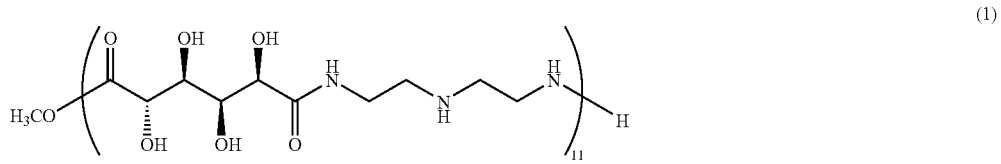

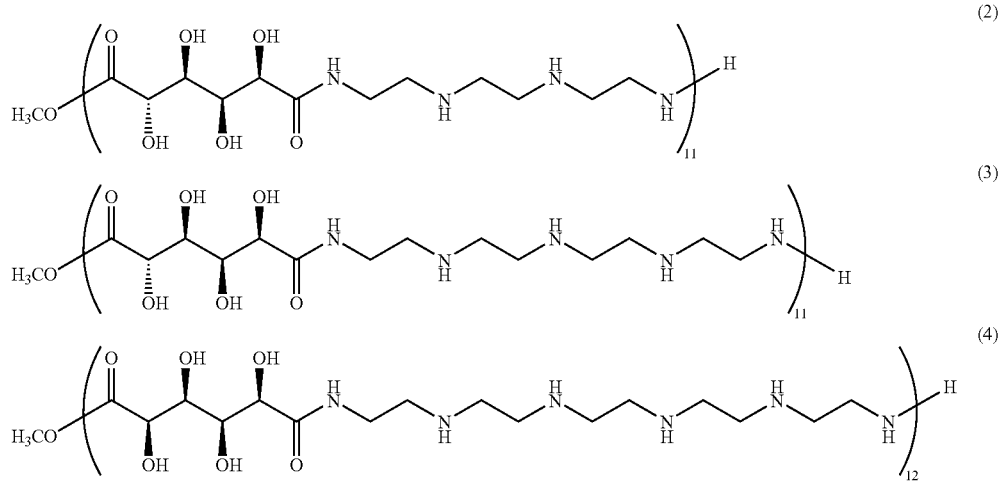

Related to the poly(glycoamidoamine)s, poly(D-glucaramidoamine)s and poly(L-tartaramidoamine)s are polyamides which include both anhydride-terminated and carboxylic acid-terminated and mixtures thereof. Examples of a carboxylic acid-terminated polyamides of the present invention includes the following (this also includes all possible isomers, diastereomers and enantiomers), wherein X=0-10, and n=1-infinity).

2) Polymeric Dendritic Polymers

Another class of polymers comprising an oligoamine shell and a cyclodextrin core is created by reacting an appropriately substituted cyclodextrin with a polyamine, such those give in Table 1, to arrive at a cyclodextrin-polyamide structure. Suitable cyclodextrins include alpha, beta and gamma cyclodextrins. These cyclodextrins may be substituted in such a way as to produce linear and branched polyamides by reaction with the appropriate polyamine. In such systems, a dedrimer-type array would be formed, in which the amine chains would be attached to the cyclodextrin base.

One specific type of dendrimer is a cyclodextrin/oligoamine which has been synthesized by selectively halogenating all of the primary hydroxyl groups around the cyclodextrin ring. An example of an oligoamine-dendron which has been prepared by this process and contains a thioacetyl group is shown below:

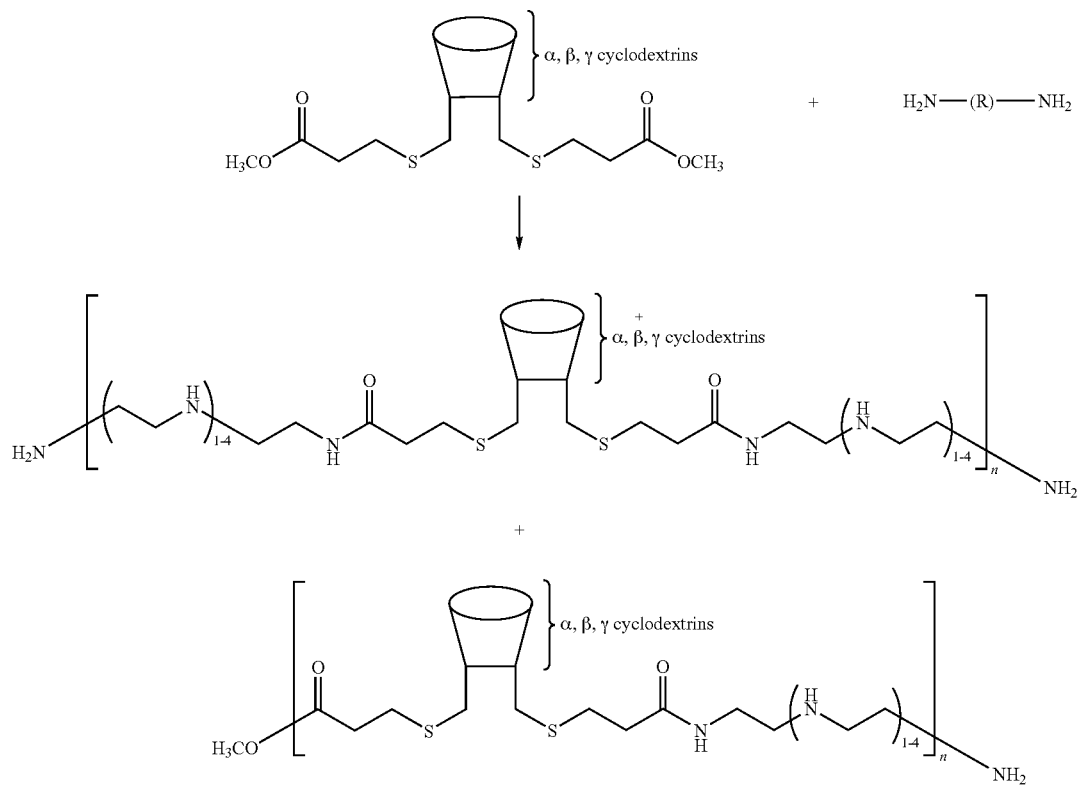

Examples of β-cyclodextrin/thiol-diethylentiamine dendrimers prepared by this process include those shown below:

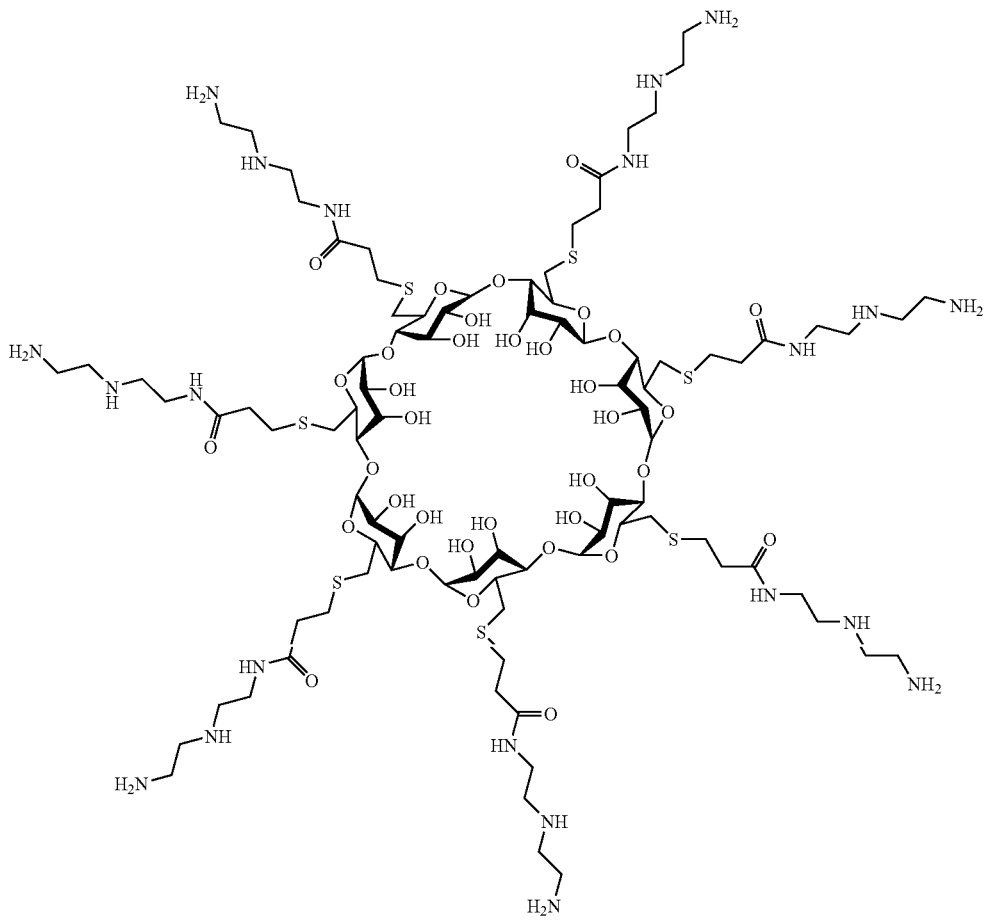 [SMILES: NCCNCCNC(=O)CCSCC1O[C@@H]2O[C@@H]3C(CSCCC(=O)NCCNCCN)O[C@H](O[C@@H]4C(CSCCC(=O)NCCNCCN)O[C@H](O[C@@H]5C(CSCCC(=O)NCCNCCN)O[C@@H](O[C@@H]6C(CSCCC(=O)NCCNCCN)O[C@@H](O[C@@H]7C(CSCCC(=O)NCCNCCN)O[C@@H](O[C@@H]8C(CSCCC(=O)NCCNCCN)O[C@H](O[C@H]1[C@H](O)C2O)C(O)[C@H]8O)C(O)[C@H]7O)C(O)[C@H]6O)C(O)[C@@H]5O)C(O)[C@H]4O)C(O)[C@H]3O]

40

Another example of a dendritic cyclodextrin is a cyclodextrin/triazole system (see structures 14 a and 14 b.1-14.b.4). Such dendrimers may be prepared by a copper-catalyzed 1,3-dipolar addition as shown below. The ability of such dendrimers to bind DNA at low N/P ratios suggests a use as a DNA delivery vehicle. Examples of dendrimers prepared by this process include, but are not limited to, the following examples.

One dendrimer is synthesized by 1,3 dipolar addition of acetylated per-azido beta-cyclodextrin and an alkyne dendron with a copper(I) catalyst. The dendron was synthesized by coupling t-butylcarbonate (BOC) protected ethylenediamine with propiolic acid. All of the products were purified using silica gel column chromatography. The characterization of the precursors and dendron was completed using $^1$H NMR, IR, and mass spectrometry. The final step in the synthesis of the triazole dendrimer required the 'click reaction'. The azide group present in core moiety undergoes 1,3 dipolar addition with the acetylene group present in the dendron using a copper(I) catalyst. The 1,4 isomer of the triazole is obtained exclusively with this reaction. Finally, through deprotection of the BOC and purification via column chromatography, pure dendrimer or linear polymer is obtained. The scheme for the synthesis of the triazole dendrimers 14 is shown in below:

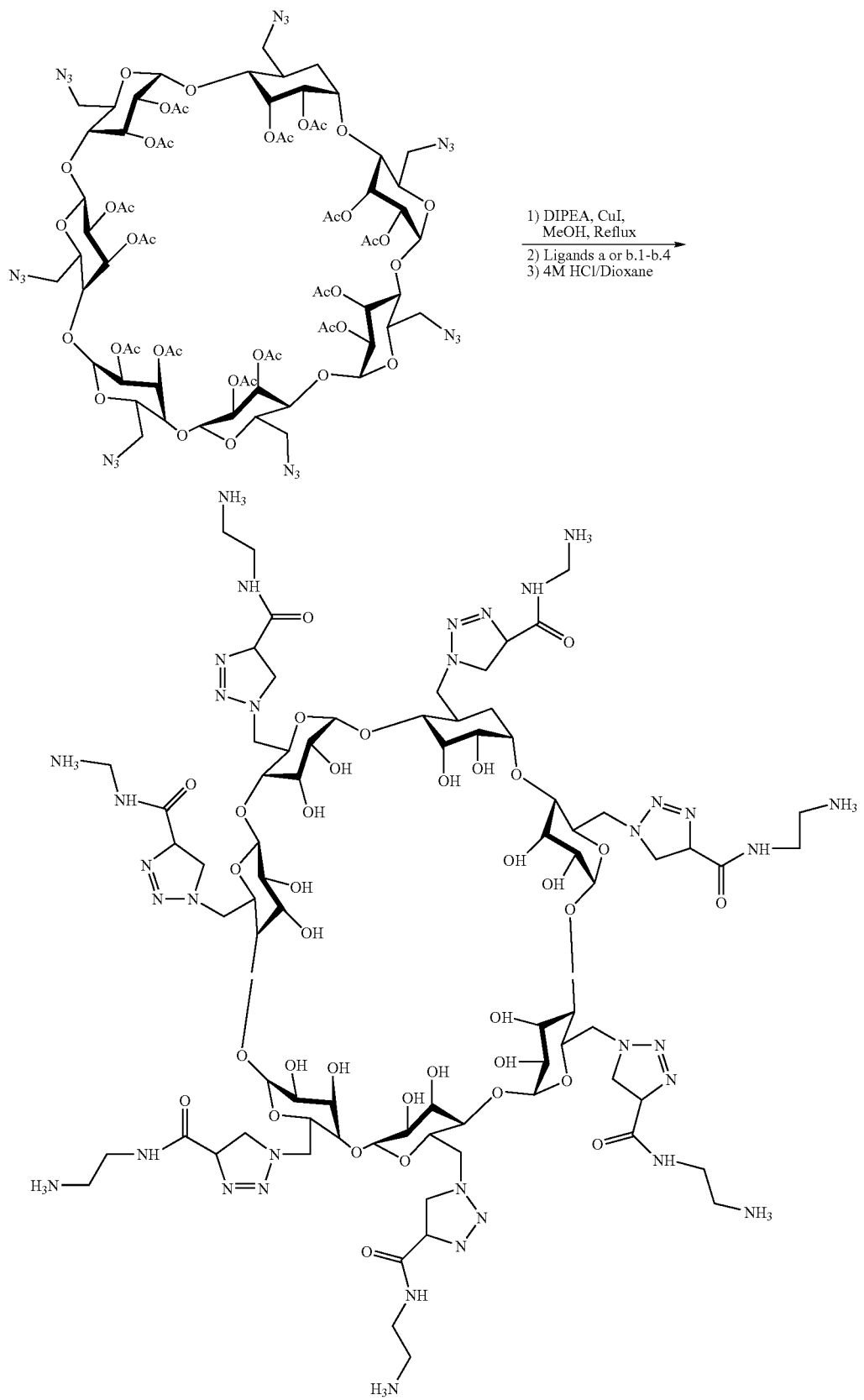

-continued
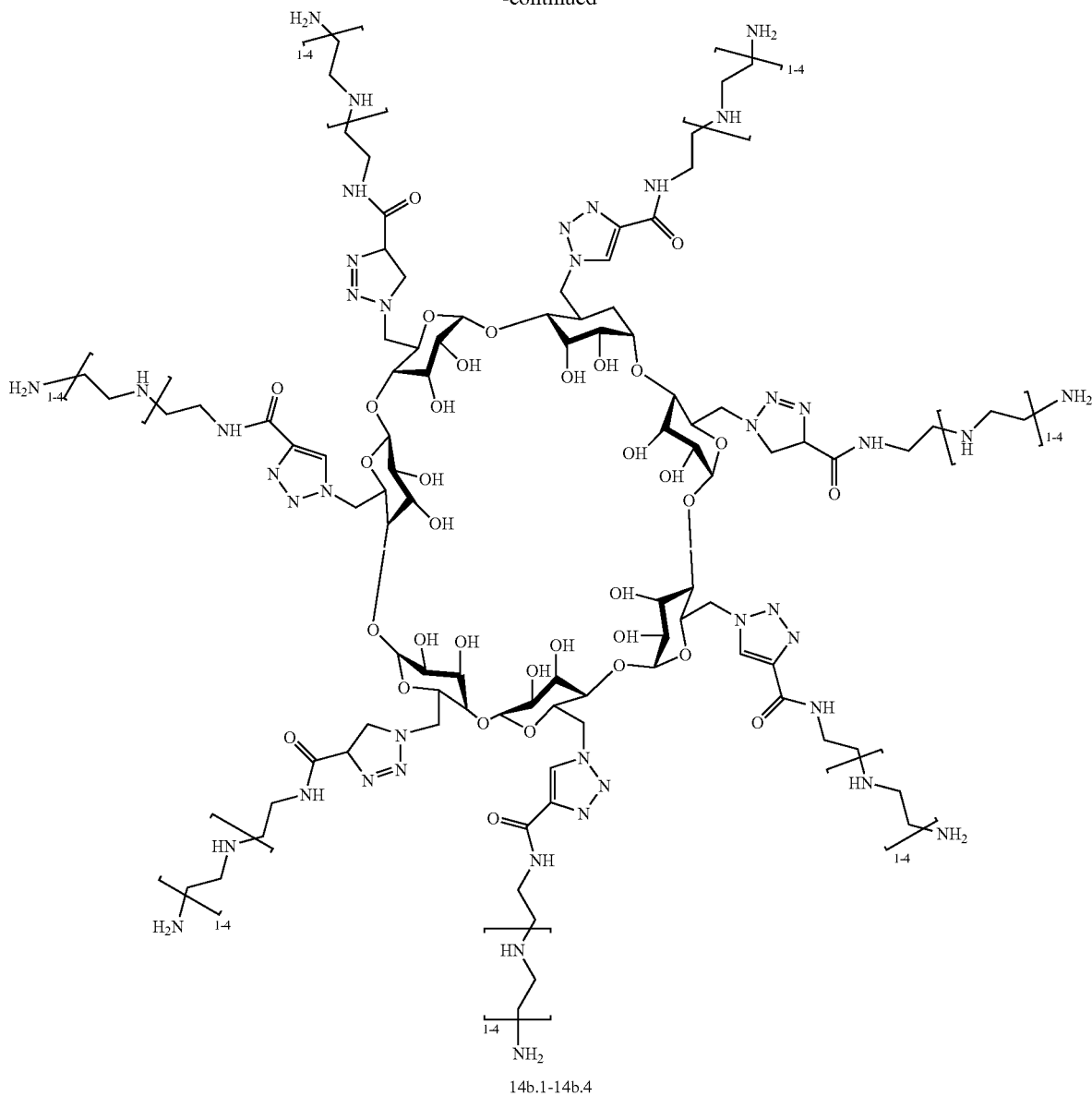
14b.1-14b.4
3) 1,3-Dipolar Addition Polymers
A third class of materials are prepared by combining a diazide monomer (usually a carbohydrate diazide) with an a dialkyne unit containing oligamines. This forms a series of polymers that contain triazole units between the combined monomers along the polymer chain (see below).

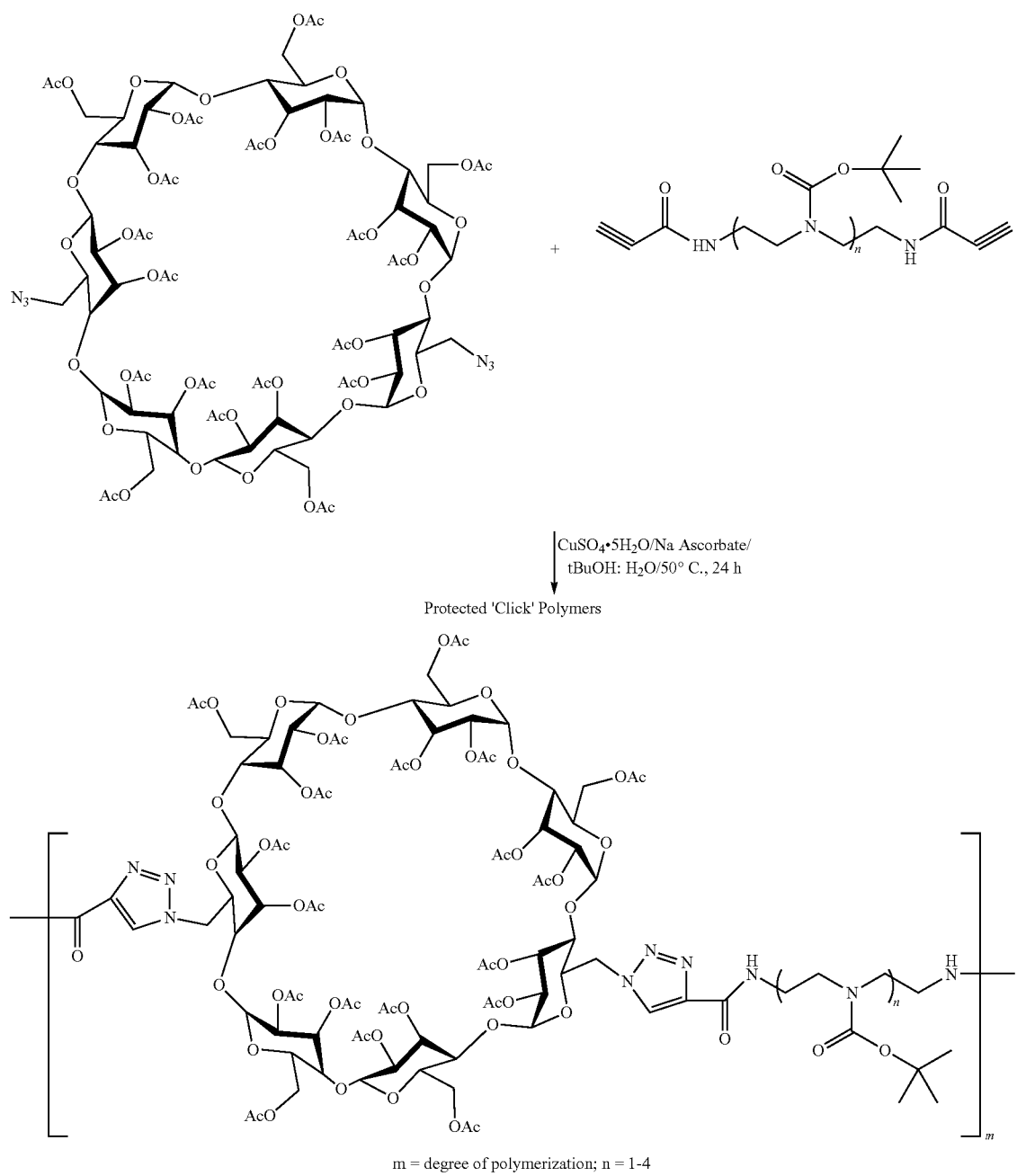
m = degree of polymerization; n = 1-4
4) Carbohydrate-Containing Biodegradable Polyesters:
-continued
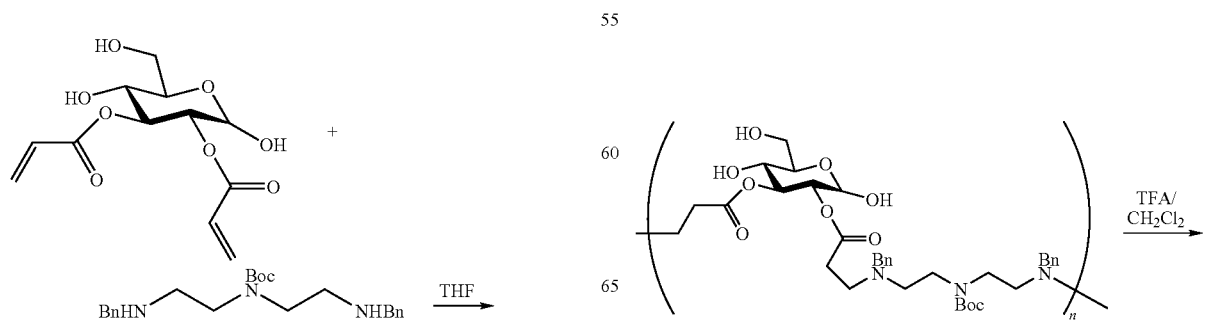

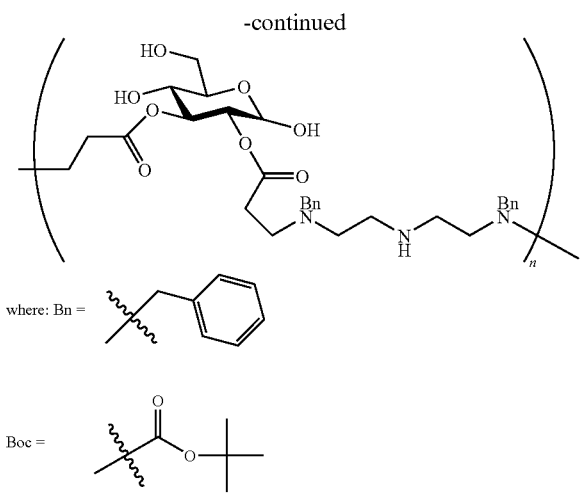

where: Bn = [benzyl group]

Boc = [t-butylcarbonate group]

The fourth class of polymers are biodegradable polyesters. These materials are formed by combining a carbohydrate alkene molecule with a series of oligoamines. Through protecting the oligoamines, linear polyesters can be formed. If the oligoamines are not protected, a series of hyperbranched polymers can be formed. In addition, most any carbohydrate molecule may be utilized as the starting material for this class of polymers, including monosaccharides and disaccharides and polysaccharides. With this property in mind, a biodegradable gene delivery system based on an oligoamine and a carbohydrate moiety is prepared, which incorporates an ester bond between repeated carbohydrates such as glucose molecules and oligoamine residues. For this reactoion, any type of carbohydrate, substituted carbohydrate, or oligoamine or substituted oligoamine residues can be used to form any molecular weight (degree of polymerization) of polymers.

As shown in the reaction scheme above, a diacrylate glucose monomer and BOC (t-butylcarbonate)-protected diethylenetriamine are polymerized in THF for 48. hours. The polymer is isolated via precipitation with hexane and dried under the vacuum. Finally, the BOC groups are removed under acidic conditions to yield the deprotected polymer structure The degradation time can vary significantly according to the degree of hydrophobicity of the polyester structure; hydrophobic polymers will decrease the rate of hydrolysis.

Polyplex Formation

Generally, the polyplexes are formed by mixing a biologically active molecule where preferably the biologically active molecule is an oligonucleotide or polypeptide, for instance, pDNA (plasmid DNA), with an appropriate volume of polymer dissolved in nuclease-free water to yield a final N/P ratio of about 20 to about 60, or from about 25 to about 35, or alternatively, an N/P ratio of about 30. The polyplex size for the majority of the polyplexes is between about 50 to about 650 nm. In general, as the number of amine units between each polymer increases, the binding affinity increases and the size of the polyplexes produced decreases.

The amine number and the hydroxyl stereochemistry mediate the compaction of pDNA into nanoparticles. In general, as the number of amine units between each polymer increases, the polymer-pDNA binding affinity increases and the size of the polyplexes produced decreases. In general, the galactarate polymers are the most efficient and the D-mannarate polymers are the least efficient to compact pDNA.

The optimum concentration of polyplex formulation to promote the smallest polyplex formation is at a final concentration of about 0.01 mg/mg of nucleic acid (after it is mixed with each polymer at a charge ratio of 10+/−), all of the polymers formed polyplexes in the proper range to be endocytosed. The polymers compact pDNA into polyplexes between about 75 to about 170 nm. The N/P ratios used for this are chosen based on a common N/P ratio in which all of the polymers inhibited DNA migration on the gel shift assay for each polymer. Each sample is analyzed by dynamic light scattering using a Brookhaven ZetaPals Instrument (Holtzville, N.Y.). The particle size of the polyplex is determined as a function of pDNA concentration. The polymers discussed above are able to compact DNA into polyplexes small enough to be endocytosed in the cell culture studies described below.

Polyamides for Nucleic Acid Delivery

In the description that follows, a number of terms used in molecular biology and medical/pharmaceutical sciences are utilized extensively. In order to provide a clear and consistent understanding of the specification and claims, including the scope to be given such terms, the following definitions are provided. Under these definitions, the following terms have the following meaning unless otherwise specified herein:

Association: the covalent or non-covalent joining of two or more molecules, which may occur permanently, temporary, or transiently. A molecular complex is formed by the stable or semi-stable association of two or more compounds.

Base Pair (bp): a partnership of adenine (A) with thymine (T), or of cytosine (C) with guanine (G) in a double stranded DNA molecule. In RNA, uracil (U) is substituted for thymine. Base pairs are the to be "complementary" when their component bases pair up normally when a DNA or RNA molecule adopts a double stranded configuration.

The term "biologically active molecule" as used herein, refers to compounds or molecules that are capable of eliciting or modifying a biological response in a system. Non-limiting examples of biologically active siNA molecules either alone or in combination with other molecules contemplated by the instant invention include therapeutically active molecules such as antibodies, cholesterol, hormones, antivirals, peptides, proteins, chemotherapeutics, small molecules, vitamins, co-factors, nucleosides, nucleotides, oligonucleotides, enzymatic nucleic acids, antisense nucleic acids, triplex forming oligonucleotides, 2,5-A chimeras, siNA, dsRNA, allozymes, aptamers, decoys and analogs thereof. Biologically active molecules of the invention also include molecules capable of modulating the pharmacokinetics and/or pharmacodynamics of other biologically active molecules, for example, lipids and polymers such as polyamines, polyamides, polyethylene glycol and other polyethers.

Cellular Delivery (also referred to herein interchangeably and equivalently as "delivery"): a process by which a desired compound is transferred to a target cell such that the desired compound is ultimately located inside the target cell, or in or on the target cell membrane. In certain uses delivery to a specific target cell type is preferable.

Cellular Delivery Molecule: a molecule that mediates the Cellular Delivery of itself, a molecular complex comprising the Cellular Delivery Molecule, and/or a molecule comprising the Cellular Delivery Molecule.

Cell delivery polymer: a polymer that functions as a Cellular Delivery Molecule, either by itself, as a part of a molecular complex. By way of non-limiting example, Cell delivery polymers include polyamides, dendritic macromolecules, and biodegradable polyesters.

Complementary Nucleotide Sequence: a sequence of nucleotides in a single-stranded molecule of DNA or RNA that is sufficiently complementary to another single strand to specifically (non-randomly) hybridize to it with consequent hydrogen bonding.

Construct: a vector sequence, or a portion thereof, that has been linked with one or more non-vector sequences.

Inducer: a molecule that triggers gene transcription by binding to a regulator protein such as a repressor. Induction: the switching on of transcription as a result of interaction of an inducer with a positive or negative regulator.

Negative Regulation of Transcription: a mechanism of control of gene expression where a gene is transcribed unless transcription is prevented by the action of a negative regulator, or repressor.

Nucleotide: a base-sugar-phosphate combination. Nucleotides are monomeric units of a nucleic acid sequence (DNA and RNA). Nucleotides may also include mono-, di- and triphosphate forms of such nucleotides. The term nucleotide includes ribonucleoside triphosphates ATP, UTP, ITP, CTG, GTP and deoxyribonucleoside triphosphates such as dATP, dCTP, dITP, dUTP, dGTP, dTTP, or derivatives thereof. Such derivatives include, for example, [aS]dATP, 7-deaza-dGTP and 7-deaza-dATP, and nucleotide derivatives that confer nuclease resistance on the nucleic acid molecule containing them. The term nucleotide as used herein also refers to dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP. According to the present invention, a "nucleotide" may be unlabeled or detectably labeled by well known techniques. Detectable labels include, for example, radioactive isotopes, fluorescent labels, chemiluminescent labels, bioluminescent labels and enzyme labels. Various labeling methods known in the art can be employed in the practice of this invention.

Nucleotide Analog: a purine or pyrimidine nucleotide that differs structurally from an A, T, G, C, or U base, but is sufficiently similar to substitute for the normal nucleotide in a nucleic acid molecule. Inosine (I) is a nucleotide analog that can hydrogen bond with any of the other nucleotides, A, T, G, C, or U. In addition, methylated bases are known that can participate in nucleic acid hybridization. Methods of preparing and using modified oligonucleotides are described in: Verma S, Eckstein F. Modified oligonucleotides: synthesis and strategy for users. Annu Rev Biochem. 1998; 67:99-134. By way of non-limiting example, nucleotide analogs include 2,6-diamino purine, 6-methyladenine, 8-azaguanine, 5-bromouracil, 5-hydroxymethyl uracil, 5-methylcytosine (SMC), 5-hydroxymethylcytosine (HMC), 8-chloroadenosine, glycosyl HMC, and gentobiosyl HMC. Fluorescent nucleotide analogs, such as those described by Jameson and Eccleston (Fluorescent nucleotide analogs: synthesis and applications. Methods Enzymol. 1997; 278:363-90), and cyclic nucleotide analogs, such as those described by Schwede et al. (Cyclic nucleotide analogs as biochemical tools and prospective drugs. Pharmacol Ther 2000 87(2-3):199-226) may also be used in the invention.

Nucleic Acid: As used herein "nucleic acid" and its grammatical equivalents will include the full range of polymers of single or double stranded nucleotides. A nucleic acid typically refers to a polynucleotide molecule comprised of a linear strand of two or more nucleotides (deoxyribonucleotides and/or ribonucleotides) or variants, derivatives and/or analogs thereof. The exact size will depend on many factors, which in turn depends on the ultimate conditions of use, as is well known in the art. The nucleic acids of the present invention include without limitation primers, probes, oligonucleotides, vectors, constructs, plasmids, genes, transgenes, genomic DNA, cDNA, PCR products, restriction fragments, and the like.

Promoter: As used herein, a promoter is an example of a transcriptional regulatory sequence, and specifically is a DNA sequence generally described as the 5'-region of a gene located proximal to the start codon. The transcription of an adjacent DNA segment is initiated at the promoter region. A repressible promoter's rate of transcription decreases in response to a repressing agent. An inducible promoter's rate of transcription increases in response to an inducing agent. A constitutive promoter's rate of transcription is not specifically regulated, though it can vary under the influence of general metabolic conditions.

Recognition sequence: As used herein, a recognition sequence is a particular sequence to which a protein, chemical compound, DNA, or RNA molecule (e.g., restriction endonuclease, a modification methylase, or a recombinase) recognizes and binds. In the present invention, a recognition sequence will typically, but need not, refer to a recombination site. For example, the recognition sequence for Cre recombinase is loxP which is a 34 base pair sequence comprised of two 13 base pair inverted repeats (serving as the recombinase binding sites) flanking an 8 base pair core sequence. See FIG. 1 of Sauer, B., Current Opinion in Biotechnology 5:521-527 (1994). Other examples of recognition sequences are the attB, attP, attL, and attR sequences which are recognized by the recombinase enzyme Integrase. The attB site is an approximately 25 base pair sequence containing two 9 base pair core-type Int binding sites and a 7 base pair overlap region. The attP site is an approximately 240 base pair sequence containing core-type Int binding sites and arm-type Int binding sites as well as sites for the auxiliary proteins integration host factor (IHF), FIS and excisionase (Xis). See Landy, Current Opinion in Biotechnology 3:699-707 (1993). Such sites may also be engineered according to the present invention to enhance production of products in the methods of the invention. When such engineered sites lack the P1 or H1 domains to make the recombination reactions irreversible (e.g. attR or attP), such sites may be designated attR' or attP' to indicate that the domains of these sites have been modified in some way.

Repressor a protein which prevents transcription by binding to a specific site on DNA.

Target Cell: any cell to which a desired compound is delivered. Cells to which the delivery methods of this invention can be applied include cells in vitro, cells ex vivo or cells in vivo. Target cells may be in cell culture, on tissue culture, in any form of immobilized state, or grown on liquid, semi-solid or solid medium. Target cells may be in the form of a monolayer. Target cells may be collected from an organism and/or cultured by any known method. Target cells include cells without cell walls and cells from which cell walls have been removed by any known treatment (e.g., formation of protoplasts) from which viable cells can be recovered.

Transcriptional regulatory sequence: As used herein, transcriptional regulatory sequence is a functional stretch of nucleotides contained on a nucleic acid molecule, in any configuration or geometry, that acts to regulate the transcription of one or more structural genes into messenger RNA. Examples of transcriptional regulatory sequences include, but are not limited to, promoters, enhancers, repressors, and the like. "Transcription regulatory sequence," "transcription sites" and "transcription signals" may be used interchangeably.

Transfection: the delivery of expressible nucleic acid to a target cell, such that the target cell is rendered capable of expressing the nucleic acid. It will be understood that the term "nucleic acid" includes both DNA and RNA without regard to molecular weight, and the term "expression" means any manifestation of the functional presence of the nucleic acid within the cell including, without limitation, both transient expression and stable expression.

Transfection Agent: any substance which provides significant enhancement of transfection (2-fold or more) over transfection compositions that do not comprise the transfection agent.

Vector: As used herein, a vector is a nucleic acid molecule that provides a useful biological or biochemical property to a nucleic acid sequence or molecule of interest, for example, an Insert, a coding region, etc. Examples include plasmids, phages, autonomously replicating sequences (ARS), centromeres, and other nucleic acid sequences that are able to replicate or be replicated in vitro or in a host cell, or to convey a desired nucleic acid segment to a desired location within a host cell. A vector may comprise various structural and/or functional sequences, for example, one or more restriction endonuclease recognition sites at which the vector sequences can be manipulated in a determinable fashion without loss of an essential biological function of the vector, and into which a nucleic acid fragment can be inserted, for example to bring about its replication and/or cloning. Vectors can further provide primer sites, e.g., for PCR, transcriptional and/or translational initiation and/or regulation sites, recombinational signals, replicons, selectable markers, and other sequences known to those skilled in the art. A vector comprising a nucleic acid insert is a Construct. Thus, a gene therapy construct is a gene therapy vector into which a therapeutic gene has been cloned. Similarly, a construct that expresses an antisense transcript is an "antisense construct."

Biologically Active: As used herein, the term "biologically active" (synonymous with "bioactive") indicates that a composition or compound itself has a biological effect, or that it modifies, causes, promotes, enhances, blocks, or reduces a biological effect, or which limits the production or activity of, reacts with and/or binds to a second molecule that has a biological effect. The second molecule can, but need not, be endogenous. A "biological effect" may be but is not limited to one that stimulates or causes an immunoreactive response; one that impacts a biological process in a cell, tissue or organism (e.g., in an animal); one that impacts a biological process in a pathogen or parasite; one that generates or causes to be generated a detectable signal; and the like. Biologically active compositions, complexes or compounds may be used in investigative, therapeutic, prophylactic and diagnostic methods and compositions. Biologically active compositions, complexes or compounds act to cause or stimulate a desired effect upon a cell, tissue, organ or organism (e.g., an animal). Non-limiting examples of desired effects include modulating, inhibiting or enhancing gene expression in a cell, tissue, organ, or organism; preventing, treating or curing a disease or condition in an animal suffering therefrom; limiting the growth of or killing a pathogen in an animal infected thereby; augmenting the phenotype or genotype of an animal; stimulating a prophylactic immunoreactive response in an animal; or diagnosing a disease or disorder in an animal.

In the context of investigative applications of the invention, including but not limited to forensic and scientific research applications, the term "biologically active" indicates that the composition, complex or compound has an activity that results, directly or indirectly, in a change in some form of measurable output in materials, biological samples, cells or organisms that have been contacted therewith. Investigative applications may be used to determine the quantity or concentration of a selected target compound in a test sample, to determine the effect of a bioactive compound upon cells or animals, or to screen for compounds having an activity that alters, blocks or augments a selected biological activity.

In the context of therapeutic applications of the invention, the term "biologically active" indicates that the composition, complex or compound has an activity that impacts an animal suffering from a disease or disorder in a positive sense and/or impacts a pathogen or parasite in a negative sense. Thus, a biologically active composition, complex or compound may cause or promote a biological or biochemical activity within an animal that is detrimental to the growth and/or maintenance of a pathogen or parasites; or of cells, tissues or organs of an animal that have abnormal growth or biochemical characteristics, such as cancer cells.

In the context of prophylactic applications of the invention, the term "biologically active" indicates that the composition or compound induces or stimulates an immunoreactive response. In some preferred embodiments, the immunoreactive response is designed to be prophylactic, i.e., to prevent infection by a pathogen. In other preferred embodiments, the immunoreactive response is designed to cause the immune system of an animal to react to the detriment of cells of an animal, such as cancer cells, that have abnormal growth or biochemical characteristics. In this application of the invention, compositions, complexes or compounds comprising antigens are formulated as a vaccine.

In the context of diagnostic applications on the invention, the term "biologically active" indicates that the composition, complex or compound can be used for in vivo or ex vivo diagnostic methods and in diagnostic compositions and kits. For diagnostic purposes, a preferred biologically active composition or compound is one that can be detected, typically (but not necessarily) by virtue of comprising a detectable polypeptide. Antibodies to an epitope found on composition or compound may also be used for its detection. It will be understood by those skilled in the art that a given composition, complex or compound may be biologically active in therapeutic, diagnostic and/or prophylactic applications. A composition, complex or compound that is described as being "biologically active in a cell" is one that has biological activity in vitro (i.e., in a cell or tissue culture) or in vivo (i.e., in the cells of an animal). A "biologically active component" of a composition or compound is a portion thereof that is biologically active once is liberated from the composition or compound. It should be noted that such a component may also be biologically active as a moiety or other portion of the composition or compound.

In the disclosure and the claims, "and/or" means additionally or alternatively. Moreover, any use of a term in the singular also encompasses plural forms.

Other terms used in the fields of recombinant DNA technology, molecular and cell biology, and the medical/pharmaceutical arts, as used herein, are intended to encompass the broadest scope term understood in the art for a given and will be generally understood by one of ordinary skill in the applicable arts.

In one embodiment, the invention encompasses a method of delivering a biologically active molecule to a cell, comprising contacting the cell with (a) a biologically active molecule and (b) a cellular delivery polymer.

In one embodiment, the present invention also provides for compositions and non-covalent complexes comprising one or more polymers of the present invention, e.g., polyamides, dendritic macromolecules (polymers comprising an oligoamine shell and a cyclodextrin core), and carbohydrate-containing degradable polyesters, and at least one nucleic acid molecule (e.g., one or more oligonucleotides) or at least one polypeptide or both. The invention also provides compositions comprising such complexes.

Complexes according to the invention or portions thereof, can comprise a cellular delivery molecule or agent that can facilitate the translocation of the complex or portion thereof into cells. In some embodiments, cellular delivery molecules for use in the present invention may comprise one or more one or more polymers of the present invention, e.g., polyamides, dendritic macromolecules (polymers comprising an oligoamine shell and a cyclodextrin core), and carbohydrate-containing degradable polyesters.

In some embodiments, a cell, tissue, organ or organism may be contacted with a complex of the invention. Preferably, the complex is taken up by the cell or by one or more cells of the tissue, organ or organism.

In another exemplary and non-limiting embodiment of the invention, compositions comprising complexes between cellular delivery polymers and oligonucleotides are formed and can be applied to cultured mammalian cells. The complex may also comprise a combination of labeled and nonlabeled nucleic acid and or peptide. These complexes allow mediation of an activity associated with the oligonucleotide, which, by way of non-limiting example, can be a gene-containing oligonucleotide, an antisense oligonucleotide, an aptamer, a short interfering RNA (siRNA), a short hairpin RNA (shRNA), a small temporally regulated RNA (stRNA), and the like. In some embodiments, oligonucleotides are preferred.

In other specific embodiments, the biologically active molecule and/or cell delivery agent is covalently labeled with a fluorophores (fluorescent moiety), for example with fluorescein or a derivative of fluorescein.

In another embodiment, the compositions may comprise one or more fluorescent molecules or moieties, which may be the same or different, and may be covalently attached to one or more polypeptides and/or nucleic acid molecules in the complexes of the invention. Alternatively, or in addition, complexes of the invention may comprise one or more "free" fluorescent molecule (i.e., one or more fluorescent molecules that are not covalently attached to either the polypeptide or the oligonucleotide but may still be associated with the complex). One or more of the compounds of the compositions or complexes can be a biologically active molecule.

Kits according to the invention may further comprise one or more transfection agents, one or more cells, one or more nucleic acids, one or more set of instructions, and one or more biologically active molecules.

Other additional kit components include without limitation: additional nucleic acids, such as oligonucleotides, iRNA molecules, plasmids, etc.; one or more recombinases, including without limitation site-specific recombinases; one or more recombination proteins; and/or one or more cells. In some embodiments, the cells are competent for transfection or transformation.

In other embodiments, the invention provides a complex comprising a cell delivery polymer and a biologically active agent that is desirably taken up by cells, wherein the cell delivery polymer or biologically active agent comprises a fluorescent moiety.

The nucleic acid of the complexes and other embodiments of the invention can comprise from 5 bases to about 200 kilobases. Any type of nucleic acid may be used, including by way of non-limiting example mRNA, tmRNA, tRNA, rRNA, siRNA, shRNA, PNA, ssRNA, dsRNA, ssDNA, dsDNA, DNA:RNA hybrid molecules, plasmids, artificial chromosomes, gene therapy constructs, cDNA, PCR products, restriction fragments, ribozymes, antisense constructs, and combinations thereof. Reviews of tmRNA include Muto A, Ushida C, Himeno H. A bacterial RNA that functions as both a tRNA and an mRNA. Trends Biochem Sci. 1998 January; 23(1):25-9; and Withey J H, Friedman D I. The biological roles of trans-translation. Curr Opin Microbiol. 2002 April; 5(2): 154-9). The nucleic acid may comprise one or more chemical modifications.

A complex according to the invention may further comprise one or more transfection agents, one or more recombinases and, additionally or alternatively, one or more recombination proteins.

A nucleic acid used in the invention includes, in some embodiments, a sequence that encodes a protein or a portion thereof. In some embodiments, a cellular nucleic acid encoding the protein, or a portion thereof, is desirably replaced by the sequence in one form of gene therapy. Additionally or alternatively, the protein is expressed in the cell. The protein may be exogenous or endogenous. In the latter case, the cells to be transfected may comprise a non-functional form of the protein.

A composition of the invention may be a pharmaceutical composition. In certain embodiments, the biologically active molecule is one or more of the nucleic acids that has a biological activity, including but not limited to therapeutic activity. By way of non-limiting example, biologically active nucleic acids are selected from the group consisting of mRNA, tmRNA, tRNA, rRNA, siRNA, shRNA, PNA, ssRNA, dsRNA, ssDNA, dsDNA, DNA:RNA hybrid molecules, plasmids, artificial chromosomes, gene therapy constructs, cDNA, PCR products, restriction fragments, ribozymes, antisense constructs, and combinations thereof.

Additionally or alternatively, polypeptide of the complex is biologically active. A biologically active polypeptide may be a therapeutic protein. By way of non-limiting example, bioactive proteins include antibodies or antibody fragments, hormones, enzymes, transcription factors, growth factors, and the like.

The invention further provides a method of providing gene therapy to an individual in need thereof, of treating an individual suffering from a disease or disorder, the method comprising contacting the individual, or cells therefrom, with one or more complexes, compositions and/or pharmaceutical compositions of the invention.

The invention further provides a method of testing a cellular response to a test compound, the method comprising: (a) contacting a first cell with, in any order or combination, a biologically active molecule and a cellular delivery polymer, (b) contacting a second cell with, in any order or combination, a second biologically active molecule and the cellular delivery polymer, (c) contacting the cells with the test compound, before (a); during (a) or (b); between (a) and (b); and, additionally or alternatively, after (b); (d) measuring and comparing at least one parameter of from the first cell with the signal from the second cell. In certain embodiments, one or more of the cells comprise one or more reporter genes that generate a detectable signal or interfere with the production of a detectable signal.

In one embodiment, the present invention provides for a new series of polyamides for use as gene delivery agents. These polymers bind products, e.g., oligonucliotides, and facilitate cellular uptake. In one embodiment, the invention provides for the in vitro delivery of plasmid DNA into cells. In one embodiment, the invention provides for the in vivo delivery of plasmid DNA into cells.

In one embodiment, the present invention relates to the use of polyamides for delivering nucleic acids into a cell. In one embodiment, the nucleic acid is an oligonucleotide. In another embodiment, the oligonucleotide contains from about 10 to about 1000 nucleotides. In another embodiment, the oligonucleotide is an antisense oligonucleotide or oligodeoxynucleotide. In another embodiment, the oligonucleotideis an oligonucleotide, an antisense oligonucleotide residue or oligodeoxynucleotide residue.

In another embodiment, the nucleic acid is selected from the group consisting of antisense constructs, antisense polynucleotide, artificial chromosomes, cDNA, concatemers, concatemeric decoy oligonucleotides, CpG oligomers, cyclic oligonucleotides, decoy oligonucleotides, DNA:RNA hybrid molecules, dsDNA, dsRNA, gene therapy constructs, LNA, morpholinos, mRNA, oligonucleotides and oligodeoxynucleotides with phosphorodiester backbones or phosphorothioate backbones, PCR products, plasmids, PNA, restriction fragments, ribozyme, RNA, RNAi, RNAi inducing polynucleotide, rRNA, shRNA, siRNA, spiegelmers, ssDNA, ssRNA, tmRNA, transgenes, tricyclo-DNA, triple helices, tRNA, and combinations thereof.

In one specific embodiment, the present invention provides polymer compositions, complexes and methods for delivering one or more nucleic acids (e.g., one or more nucleic acid molecules, oligonucleotides, polynucleotides, vectors, genes and the like) and/or one or more peptides (e.g., one or more peptides, oligopeptides, polypeptides, proteins or protein complexes) to cells, tissues, organs and whole organisms. The compositions and complexes of the invention typically comprise one or more nucleic acids and/or one or more proteins or polypeptides (which can be cellular delivery (suitably, translocating) peptides, polypeptides or proteins.

In certain such aspects of the invention, the complexes comprising one or more nucleic acids and/or one or more peptides are delivered to and taken up by the cells, tissues, organs or organisms, and cells, tissues, organs or organisms. The invention also provides compositions comprising the polymer complexes of the invention and one or more additional components. Suitable such compositions, for example, include pharmaceutical compositions comprising one or more of the complexes of the invention and one or more pharmaceutically acceptable carriers, excipients or diluents therefor. The invention also provides methods for producing such complexes and compositions, and methods of using such complexes and compositions to deliver one or more nucleic acid molecules and/or one or more peptides to cells, tissues, organs or organisms, for example for therapeutic or prophylactic purposes. The invention also provides kits comprising the complexes and compositions of the invention, and optionally further comprising one or more additional components suitable for use in or with the complexes and compositions, and/or for carrying out the methods, of the present invention.

In one embodiment, the present invention relates to the use of nucleic acids. In one embodiment, the nucleic acid is an oligonucleotide. In another embodiment, the oligonucleotide contains from about 10 to about 1000 nucleotides. In another embodiment, the oligonucleotide is an antisense oligonucleotide or oligodeoxynucleotide. In another embodiment, the oligonucleotideis an oligonucleotide, an antisense oligonucleotide residue or oligodeoxynucleotide residue.

In another embodiment, the nucleic acid is selected from the group consisting of antisense constructs, antisense polynucleotide, artificial chromosomes, cDNA, concatemers, concatemeric decoy oligonucleotides, CpG oligomers, cyclic oligonucleotides, decoy oligonucleotides, DNA:RNA hybrid molecules, dsDNA, dsRNA, gene therapy constructs, LNA, morpholinos, mRNA, oligonucleotides and oligodeoxynucleotides with phosphorodiester backbones or phosphorothioate backbones, PCR products, plasmids, PNA, restriction fragments, ribozyme, RNA, RNAi, RNAi inducing polynucleotide, rRNA, shRNA, siRNA, spiegelmers, ssDNA, ssRNA, tmRNA, transgenes, tricyclo-DNA, triple helices, tRNA, and combinations thereof.

The present invention provides a new class of non-viral transduction vectors that can be used for both in vivo and in vitro applications. In particular, these vectors can be used for gene transfer applications. These new gene transduction vectors can achieve transfer efficiencies far greater to commercially available polymeric and liposomal gene transfer vectors while maintaining little or no toxicity in vitro. Their low in vitro toxicity makes them ideal candidates for in vivo use. The present invention provides a gene transfer vector that has comparable efficiency to a viral vector without the potential for a life-threatening immune response.

Furthermore, the unique polycationic structure of these polymers associates with many suitable bioactive molecules, including proteins and other compounds that poses multiple cationic sites. The polymer can act as a delivery vehicle for the associated bioactive molecule, in vivo or in vitro, to the cells of interest for the bioactive molecule.

In one embodiment, the present invention provides for a new series of polyamides for use as gene delivery agents. These polymers bind products, e.g., oligonucliotides, and facilitate cellular uptake. In one embodiment, the invention provides for the in vitro delivery of plasmid DNA into cells.

Polypeptides

As noted above, the compositions and complexes of the present invention comprise one or more peptides, polypeptides or proteins. In certain aspects of the invention, the peptides, polypeptides or proteins used in these complexes and compositions are peptides, polypeptides or proteins that are to be delivered to cells, tissues, organs or organisms for any suitable biological, therapeutic and/or prophylactic purpose.

As used herein, the term "polypeptide" includes without limitation peptides (oligopeptides), proteins, and polypeptides. All of these are polymers of two or more amino acids joined by an amino bond. Generally, peptides comprise from 2 to about a amino acid residues, wherein "a" is any whole integer between 5 and 50, preferably between 10 and 30, and may be isolated from natural sources or more typically are synthesized in vitro. As used herein, the term "oligopeptide" may be used interchangeably and equivalently with the term "peptide" as defined above. As used herein, "polypeptides" generally comprise about b amino acids, wherein "b" is any whole integer between 25 and 50,000, preferably between 50 and 10,000, and more preferably between 50 and 1,000. The term "protein" encompasses polypeptides, as well as complexes of two or more covalently or non-covalently bonded polypeptides. Polypeptides and proteins are purified from their natural sources and/or are synthesized using recombinant DNA technology.

Peptides, polypeptides, proteins and protein complexes suitable for use in the complexes, compositions and methods of the present invention include any peptide, polypeptide, protein and protein complex, or portion thereof, that has a desired biological or physiological effect on the cells, tissues, organs and organisms to which the peptides, polypeptides, proteins and protein complexes are delivered. Non-limiting examples of such peptides, polypeptides, proteins and protein complexes include: enzymes, e.g., kinases; peptidases/proteinases; oxidoreductases; nucleases; recombinases (including Cre, Int, Flp, Tn5 resolvase, and the like); ligases (including DNA ligases and the like); lyases; isomerases (including topoisomerases and the like); polymerases (including DNA polymerases, RNA polymerases, reverse transcriptases, and the like); transferases (including terminal transferases, glutathione S-transferases, and the like); ATPases; GTPases; etc.; cytokines, e.g., growth factors (such as epidermal growth factor (EGF), fibroblast growth factors (FGFs), keratinocyte growth factors (KGFs), hepatocyte growth factors (HGFs), platelet-derived growth factor (PDGF), transforming growth factors alpha and beta (TGF-α and TGF-β), neurotrophic factor (NTF), ciliary neurotrophic factor (CNTF), brain-derived neurotrophic factor (BDNTF), glial-derived neurotrophic factor (GDNTF), bone morphogenic proteins (BMPs), and the like, and variants thereof); interleukins (such as IL-1 through IL-18, and the like, and variants thereof); interferons (such as IFN-α, IFN-β, IFN-γ, and the like, and variants thereof); colony-stimulating factors (such as granulocyte colony-stimulating factor (G-CSF), macrophage colony-stimulating factor (M-CSF), granulocyte-macrophase colony-stimulating factor (GM-CSF); erytiropoietin (Epo); thrombopoietin (Tpo); leukemia inhibitory factor (LIF/Steel Factor); tumor-necrosis factors (INFs); and the like, and variants thereof); peptide hormones (such as antidiuretic hormone, chorionic gonadotropin, leutenizing hormone, follicle-stimulating hormone, insulin, prolactin, somatomedins, growth hormone, thyroid-stimulating hormone, placental lactogen, and the like, and variants thereof); etc.; intraceullar signalling peptides; receptors (e.g., cytokine receptors, hormone receptors, antibody receptors, integrins and other extracellular matrix receptors, neurotransmitter receptors, viral receptors, and the like, and variants thereof); antibodies (e.g., polyclonal or monoclonal antibodies, fragments thereof (including Fab and Fc fragments and portions thereof), and multi-antibody complexes); vaccine components (including, but not limited to, proteins or peptides of etiologic agents such as viruses, bacteria, fungi (including yeasts), parasites and the like; proteins or peptides of tumor cells or other cancer-related proteins or peptides; and other proteins or peptides against which it is desirable to produce an immune response in an animal, suitably a mammal such as a human); structural and/or functional proteins or peptides (e.g., hemoglobin, albumins including serum albumins, cytoskeletal proteins, transmembrane channel proteins or peptides, and the like, and fragments or variants thereof); synthetic peptides (e.g., hexahistidine, polylysine, and other synthetic peptides of any length containing a desired sequence of two or more amino acids linked together by peptide bonds to form a peptide, oligopeptide, polypeptide or protein, any and all of which can be produced by art-known methods of synthetic peptide synthesis that will be familiar to the ordinarily skilled artisan, and that are described herein); and the like. Of course, other suitable peptides, oligopeptides, polypeptides and proteins suitable for use in accordance with the present invention (i.e., in the complexes, compositions and methods of the invention) will be familiar to one of ordinary skill and therefore are encompassed by the present invention.

Amino Acids

The term "amino acid" as used herein refers generally to a molecule having both a carboxyl (—COOH) and an amino (—NH$_2$) group attached to the same carbon atom, called the alpha-carbon atom. Amino acids can be represented by the general formula R—CH(NH$_2$)COOH, wherein R is a side chain or residue which may or may not occur naturally. Generally, the side chain (R) of an amino acid contains c carbon atoms, d nitrogen atoms, 0, 1 or 2 sulfur atoms, d oxygens, and/or d halogen atoms, wherein "c" is any whole integer from 0 to about 20, and "d" is any whole integer from 0 to about 5.

The terms "natural amino acid" and "naturally-occurring amino acid" refer to Ala, Asp, Cys, Glu, Phe, Gly, His, Ile, Lys, Leu, Met, Asn, Pro, Gln, Arg, Ser, Thr, Val, Trp, and Tyr. "Unnatural amino acids" (i.e., amino acids do not occur naturally) include, by way of non-limiting example, homoserine, homoarginine, citrulline, phenylglycine, taurine, iodotyrosine, seleno-cysteine, norleucine ("Nle"), norvaline ("Nva"), beta-Alanine, L- or D-naphthalanine, ornithine ("Orn"), and the like.

Amino acids also include the D-forms of natural and unnatural amino acids. "D-" designates an amino acid having the "D" (dextrorotary) configuration, as opposed to the configuration in the naturally occurring ("L-") amino acids. Where no specific configuration is indicated, one skilled in the art would understand the amino acid to be an L-amino acid. The amino acids can, however, also be in racemic mixtures of the D- and L-configuration. Natural and unnatural amino acids can be purchased commercially (Sigma Chemical Co.; Advanced Chemtech) or synthesized using methods known in the art. Amino acid substitutions may be made on the basis of similarity in polarity, charge, solubility, hydrophobicity, hydrophilicity, and/or the amphipathic nature of the residues as long as their biological activity is retained.

Peptide Synthesis

Peptides used in accordance with the present invention may be produced by a variety of methods that will be familiar to those of ordinary skill in the art. For reviews and enabling disclosures of peptide synthesis, see M. Bodanzsky, "Principles of Peptide Synthesis," 1st and 2nd revised ed., Springer-Verlag, New York, N.Y., 1984 and 1993; Stewart and Young, "Solid Phase Peptide Synthesis," 2nd ed., Pierce Chemical Co., Rockford, Ill., 1984; Fox J E. Multiple peptide synthesis. Mol. Biotechnol. 3:249-258, 1995; Kiso Y, Fujii N, Yajima H. New disulfide bond-forming reactions for peptide and protein synthesis. Braz J Med Biol Res. 27:2733-2744, 1994; Bongers J, Heimer E P. Recent applications of enzymatic peptide synthesis. Peptides. 15:183-193, 1994; Wade J D, Tregear G W. Solid phase peptide synthesis: recent advances and applications. Australas Biotechnol. 3:332-336, 1993; Fields G B, Noble R L. Solid phase peptide synthesis utilizing 9-fluorenylmethoxycarbonyl amino acids. Int J Pept Protein Res. 35:161-214, 1990; Newton R, Fox J E. Automation of peptide synthesis. Adv Biotechnol Processes. 10:1-24, 1988; Barany G, Kneib-Cordonier N, Mullen D G. Solid-phase peptide synthesis: a silver anniversary report. Int J Pept Protein Res. 30:705-739, 1987; Bodanszky M. In search of new methods in peptide synthesis. A review of the last three decades. Int J Pept Protein Res. 25:449-474, 1985; Chaiken I M. Semisynthetic peptides and proteins. CRC Crit. Rev Biochem. 11:255-301, 1981; Fridkin M, Patchomnik A. Peptide synthesis. Annu Rev Biochem. 43:419-443, 1974; Merrifield R B. Solid-phase peptide synthesis. Adv Enzymol Relat Areas Mol. Biol. 32:221-296, 1969; and U.S. Pat. No. 4,748,002 (Semi-automatic, solid-phase peptide multi-synthesizer and process for the production of synthetic peptides by the use of the multi-synthesizer) to Neimark et al.

Fusion Proteins

In certain embodiments, the peptides, polypeptides or proteins used in the present invention are in the form of fusion proteins. As used herein, the term "fusion protein" refers to a peptide, polypeptide or protein comprising a series of contiguous amino acids from one peptide, polypeptide or protein that are linked via peptide bonds to a series of contiguous amino acids from one or more additional peptides, polypeptides or proteins. For example, fusion of the glutathione S-transferase (GST) domain to a peptide, polypeptide or protein of interest allows the fusion protein to be purified by affinity chromatography on glutathione agarose (Pharmacia, Inc., 1995 catalog). The fusion protein may include one or more accessory sequences which function for detection, purification or cleavage of the fusion proteirL If the peptide, polypeptide or protein of interest is fused to a series of consecutive histidines (for example 6×His), the fusion protein can be purified by affinity chromatography on chelating resins containing metal ions (Qiagen, Inc.). Fusion proteins may include sequences which function as a protein tag, such as an antibody epitope (e.g., dervied from Myc), a thiorescent peptide or a poly Histag. Tags and other elements may function in the purification and/or detection of the fusion protein. In producing fusion proteins according to this aspect of the invention, it is often desirable to compare amino terminal and carboxy terminal fusions for activity, solubility, stability, and the like.

Targeting sequences are another type of accessory element that can be comprised in a fusion protein. Cellular targeting elements, which direct fusion proteins to specific cell types, include such things as antibody fragments directed to a cellular surface molecule, fragments of ligands for receptors present on a cell, cell-specific targeting sequences derived from pathogens, derivatives of cellular adhesion molecules, and the like. Intracellular targeting elements, which direct fusion proteins to subcellular locations including, without limitation, the nucleus, the cell membrane, the chloroplast, the mitochondrion, the endoplasmic reticulum, the cytoplasm, and membranes or intermembrane spaces of any of the preceding, are known and are commercially available (e.g., Invitrogen's line of pShooter vectors). Various targeting sequences are known in the art and can be readily incorporated into fusion proteins using methods known in the art. Polynucleotides encoding fusion proteins may be constructed by standard molecular biology techniques (J. Sambrook, E. F. Fritsch and T. Maniatis (1989). Molecular Cloning, A Laboratory Manual. Cold Spring Harbor Laboratory Press. Cold Spring Harbor, N.Y.).

DNA-Binding Peptides and Proteins

A variety of DNA-binding proteins, particularly those that are basic, more particularly DNA-binding proteins with a relatively high percentage of Lysine and Arginine residues ("Arg- and Lys-rich proteins"), can be used with the compositions of the invention. A DNA-binding protein can be sequence-specific, partially sequence specific, or non-specific.

See U.S. Pat. No. 5,354,844 (Protein-polycation conjugates) to Beug, et al.; U.S. Pat. No. 5,972,900 (Delivery of nucleic acid to cells) to Ferkol, Jr., et al.; U.S. Pat. No. 5,166,320 (Carrier system and method for the introduction of genes into mammalian cells); and U.S. Pat. Nos. 6,008,336, 5,844,107 and 5,877,302 (Compacted nucleic acids and their delivery to cells), U.S. Pat. No. 6,077,835 (Delivery of compacted nucleic acid to cells), all to Hanson, et al. U.S. Pat. No. 6,333,396 to Filpula, et al. (Method for targeted delivery of nucleic acids) describes a single-chain antigen-binding polypeptide comprising, at its C-terminus, N-terminus, or both, basic amino acid residues selected from the group consisting of oligo-Lys, oligo-Arg and combinations thereof. U.S. Pat. No. 6,281,005 (Automated nucleic acid compaction device) to Hanson, et al. describes a device that can be used to prepare compacted DNA complexes.

Non-Eukaryotic Histonelike Proteins

One class of DNA-binding, Arg- and Lys-rich proteins that can be used in the invention is any non-eukaryotic histonelike protein. By way of non-limiting example, these include HU protein and HU (integration host factor). HU and IHF proteins have been identified and cloned from a variety of eubacteria and archaea, including by way of non-limiting example *Aeromonas proteolytica, Bacillus caldolyticus, Bacillus caldotenax, Bacillus cereus, Bacillus globigii, Bacillus stearothermophilus, Bacillus subtilis, Bifidobacterium longum, Borrelia burgdorferi, Campylobacter jejuni, Escherichia coli, Mycoplasma gallisepticum, Neisseria gonorrhoeae, Pseudomonas aeruginosa, Pseudomonas putida, Rhodobacter capsulatus, Salmonella typhinurium, Serratia marcescens*, and *Thermotoga maritima*.

Histones

Another class of DNA-binding, Arg- and Lys-rich protein that can be used in the complexes and compositions of the present invention is a histone or mixture of a histones. Any histone protein, including without limitation H1, H2A, H$_2$B, H3 and H4, can be used. The use of histone proteins is described in the following references, all of which are incorporated herein by reference in their entireties: Balicki D, Beutler E. 1997. Histone H2A significantly enhances in vitro DNA transfection. Mol. Med. 3:782-787; Balicki et al. 2000. Histone H2A-mediated transient cytokine gene delivery induces efficient antitumor responses in murine neuroblastoma. Proc Natl Acad Sci USA 97:11500-11504; Balicki et al. 2002. Structure and function correlation in histone H2A peptide-mediated gene transfer. Proc Natl Acad Sci USA 99:7467-7471; Demirhan et al. 1998. Histone-mediated transfer and expression of the HIV-1 tat gene in Jurkat cells. J Hum Virol. 1:430-440; and Zaitsev et al. 2002. Histone HI-mediated transfection: role of calcium in the cellular uptake and intracellular fate of H1-DNA complexes. Acta Histochem 104:85-92. See also U.S. Pat. Nos. 6,180,784 and 5,744,335 (both entitled "Process of transfecting a cell with a polynucleotide mixed with an amphipathic compound and a DNA-binding protein"), both to Wolff, et al.; U.S. Pat. No. 6,458,382 ("Nucleic acid transfer complexes") to Herweijer, et al.; published PCT application WO 96/14424 ("DNA transfer method") to Hallybone; and published PCT application WO 99/19502, EP 0 967 288 A1, and EP 0 908 521 A1 (all entitled "Transfection System for the transfer of nucleic acids into cells"), all to Chandra, et al.

The human histone-like protein described in U.S. Pat. Nos. 5,851,799, 5,981,221 and 5,908,831 (all entitled "Histone-like protein), all to Bandman, et al., and the protein and peptide sequences described in U.S. Pat. Nos. 5,945,400 and 6,200,956, and Published PCT application WO 96/25508 (all entitled "Nucleic acid-containing composition, preparation and use thereof"), all to Scherman, et al., can also be used to practice the invention. Chemically modified histone proteins, including by way of non-limiting example galactosylated histones (Chen, et al., Hum Gene Ther 5:429-435, 1994), can be used in the invention.

Nucleic Acids

As noted above, the complexes of the present invention may comprise one or more nucleic acids or nucleic acid molecules, which often will comprise one or more genes of interest, that can be delivered to cells, tissues, organs or organisms using the compositions, complexes and methods of the present invention. As used herein, the term "nucleic acids" (which is used herein interchangeably and equivalently with the term "nucleic acid molecules") refers to nucleic acids (including DNA, RNA, and DNA-RNA hybrid molecules) that are isolated from a natural source; that are prepared in vitro, using techniques such as PCR amplification or chemical synthesis; that are prepared in vivo, e.g., via recombinant DNA technology; or that are prepared or obtained by any appropriate method. Nucleic acids used in accordance with the invention may be of any shape (linear, circular, etc.) or topology (single-stranded, double-stranded, linear, circular, supercoiled, torsional, nicked, etc.). The term "nucleic acids" also includes without limitation nucleic acid derivatives such as peptide nucleic acids (PNAS) and polypeptide-nucleic acid conjugates; nucleic acids having at least one chemically modified sugar residue, backbone, internucleotide linkage, base, nucleotide, nucleoside, or nucleotide analog or derivative; as well as nucleic acids having chemically modified 5' or 3' ends; and nucleic acids having two or more of such modifications. Not all linkages in a nucleic acid need to be identical.

Examples of nucleic acids include without limitation oligonucleotides (including but not limited to antisense oligonucleotides, ribozymes and oligonucleotides useful in RNA interference (RNAi)), aptamers, polynucleotides, artificial chromosomes, cloning vectors and constructs, expression vectors and constructs, gene therapy vectors and constructs, rRNA, tRNA, mRNA, mtRNA, and tmRNA, and the like. For reviews of the latter type of nucleic acid, see Muto A, Ushida C, Himeno H. A bacterial RNA that functions as both a tRNA and an mRNA. Trends Biochem Sci. 23:25-29, 1998; and Gillet R, Felden B. Emerging views on tmRNA-mediated protein tagging and ribosome rescue. Mol. Microbiol. 42:879-885, 2001.

Oligonucleotides

As used in the present invention, an oligonucleotide is a synthetic or biologically produced molecule comprising a covalently linked sequence of nucleotides which may be joined by a phosphodiester bond between the 3' position of the pentose of one nucleotide and the 5' position of the pentose of the adjacent nucleotide. As used herein, the term "oligonucleotide" includes natural nucleic acid molecules (i.e., DNA and RNA) as well as non-natural or derivative molecules such as peptide nucleic acids, phophothioate-containing nucleic acids, phosphonate-containing nucleic acids and the like. In addition, oligonucleotides of the present invention may contain modified or non-naturally occurring sugar residues (e.g., arabinose) and/or modified base residues. The term oligonucleotide encompasses derivative molecules such as nucleic acid molecules comprising various natural nucleotides, derivative nucleotides, modified nucleotides or combinations thereof. Oligonucleotides of the present invention may also comprise blocking groups which prevent the interaction of the molecule with particular proteins, enzymes or substrates.

Oligonucleotides include without limitation RNA, DNA and hybrid RNA-DNA molecules having sequences that have minimum lengths of e nucleotides, wherein "e" is any whole integer from about 2 to about 15, and maximum lengths of about f nucleotides, wherein 'f' is any whole integer from about 2 to about 200. In general, a minimum of about 6 nucleotides, preferably about 10, and more preferably about 12 to about 15 nucleotides, is desirable to effect specific binding to a complementary nucleic acid strand.

In general, oligonucleotides may be single-stranded (ss) or double-stranded (ds) DNA or RNA, or conjugates (e.g., RNA molecules having 5' and 3' DNA "clamps") or hybrids (e.g., RNA:DNA paired molecules), or derivatives (chemically modified forms thereof). Single-stranded DNA is often preferred, as DNA is less susceptible to nuclease degradation than RNA. Similarly, chemical modifications that enhance the specificity or stability of an oligonucleotide are preferred in some applications of the invention.

Certain types of oligonucleotides are of particular utility in the compositions and complexes of the present invention, including but not limited to antisense oligonucleotides, ribozymes, interfering RNAs and aptamers.

Antisense Oligonucleotides

Nucleic acid molecules suitable for use in the present invention include antisense oligonucleotides. In general, antisense oligonucleotides comprise nucleotide sequences sufficient in identity and number to effect specific hybridization with a preselected nucleic acid. Antisense oligonucleotides are generally designed to bind either directly to mRNA transcribed from, or to a selected DNA portion of, a targeted gene, thereby modulating the amount of protein translated from the mRNA or the amount of mRNA transcribed from the gene, respectively. Antisense oligonucleotides may be used as research tools, diagnostic aids, and therapeutic agents.

Antisense oligonucleotides used in accordance with the present invention typically have sequences that are selected to be sufficiently complementary to the target mRNA sequence so that the antisense oligonucleotide forms a stable hybrid with the mRNA and inhibits the translation of the mRNA sequence, preferably under physiological conditions. It is preferred but not necessary that the antisense oligonucleotide be 100% complementary to a portion of the target gene sequence. However, the present invention also encompasses the production and use of antisense oligonucleotides with a different level of complementarity to the target gene sequence, e.g., antisense oligonucleotides that are at least about 50% complementary, at least about 55% complementary, at least about 60% complementary, at least about 65% complementary, at least about 70% complementary, at least about 75% complementary, at least about 80% complementary, at least about 85% complementary, at least about 90% complementary, at least about 91% complementary, at least about 92% complementary, at least about 93% complementary, at least about 94% complementary, at least about 95% complementary, at least about 96% complementary, at least about 97% complementary, at least about 98% complementary, or at least about 99% complementary, to the target gene sequence. In certain embodiments, the antisense oligonucleotide hybridizes to an isolated target mRNA under the following conditions: blots are first incubated in prehybridization solution (5×SSC; 25 mM $NaPO_4$, pH 6.5; 1× Denhardt's solution; and 1% SDS) at 42° C. for at least 2 hours, and then hybridized with radiolabelled cDNA probes or oligonucleotide probes ($1\times10^6$ cpm/ml of hybridization solution) in hybridization buffer (5×SSC; 25 mM $NaPO_4$, pH 6.5; 1× Denhardt's solution; 250 ug/ml total RNA; 50% deionized formamide; 1% SDS; and 10% dextran sulfate). Hybridization for 18 hours at 30-42° C. is followed by washing of the filter in 0.1-6×SSC, 0.1% SDS three times at 25-55° C. The hybridization temperatures and stringency of the wash will be determined by the percentage of the GC content of the oligonucleotides in accord with the guidelines described by Sambrook et al. (Molecular Cloning: A Laboratory Manual, 2nd edition, 1989, Cold Spring Harbor Laboratory Press, Plainview, N.Y.).

Representative teachings regarding the synthesis, design, selection and use of antisense oligonucleotides include without limitation U.S. Pat. No. 5,789,573, Antisense Inhibition of ICAM-1, E-Selectin, and CMV IE1/IE2, to Baker et al.; U.S. Pat. No. 6,197,584, Antisense Modulation of CD40 Expression, to Bennett et al.; and Ellington, 1992, Current Protocols in Molecular Biology, 2nd Ed., Ausubel et al., eds., Wiley Interscience, New York, Units 2.11 and 2.12.

Ribozymes

Nucleic acid molecules suitable for use in the present invention also include ribozymes. In general, ribozymes are RNA molecules having enzymatic activities usually associated with cleavage, splicing or ligation of nucleic acid sequences. The typical substrates for ribozymes are RNA molecules, although ribozymes may catalyze reactions in which DNA molecules (or maybe even proteins) serve as substrates. Two distinct regions can be identified in a ribozyme: the binding region which gives the ribozyme its specificity through hybridization to a specific nucleic acid sequence (and possibly also to specific proteins), and a catalytic region which gives the ribozyme the activity of cleavage, ligation or splicing. Ribozymes which are active intracellularly work in cis, catalyzing only a single turnover, and are usually self-modified during the reaction. However, ribozymes can be engineered to act in trans, in a truly catalytic manner, with a turnover greater than one and without being self-modified. Owing to the catalytic nature of the ribozyme, a single ribozyme molecule cleaves many molecules of target RNA and therefore therapeutic activity is achieved in relatively lower concentrations than those required in an antisense treatment (WO 96/23569).

Representative teachings regarding the synthesis, design, selection and use of ribozymes include without limitation U.S. Pat. No. 4,987,071, RNA ribozyme polymerases, dephosphorylases, restriction endonbucleases and methods, to Cech et al.; and U.S. Pat. No. 5,877,021, B7-1 Targeted Ribozymes, to Stinchcomb et al.; the disclosures of all of which are incorporated herein by reference in their entireties.

Nucleic Acids for RNAi (RNAi Molecules)

Nucleic acid molecules suitable for use in the present invention also include nucleic acid molecules, particularly oligonucleotides, useful in RNA interference (RNAi). In general, RNAi is one method for analyzing gene function in a sequence-specific manner. For reviews, see Tuschl, T., Chembiochem. 2:239-245 (2001), and Cullen, B. R., Nat. Immunol. 3:597-599 (2002). RNA-mediated gene-specific silencing has been described in a variety of model organisms, including nematodes (Parrish, S., et al., Mol Cell 6:1077-1087 (2000); Tabara, H., et al., Cell 99:123-132 (1999); in plants, i.e., "co-suppression" (Napoli, C., et al., Plant Cell 2:279-289 (1990)) and post-transcriptional or homologous gene silencing (Hamilton, A. J. and D. C. Baulcombe, Science 286:950-952 (1999); Hamilton, et al., EMBO J. 21:4671-4679 (2002)) (PTGS or HGS, respectively) in plants; and in fungi, i.e., "quelling" (Romano, N. and G. Macino, Mol Microbiol 6:3343-3353 (1992)). Examples of suitable interfering RNAs include siRNAs, shRNAs and stRNAs. As one of ordinary skill will readily appreciate, however, other RNA molecules having analogous interfering effects are also suitable for use in accordance with this aspect of the present invention.

Small Interfering RNA (siRNA)

RNAi is mediated by double stranded RNA (dsRNA) molecules that have sequence-specific homology to their "target" mRNAs (Caplen, N. J., et al., Proc Natl Acad Sci USA 98:9742-9747 (2001)). Biochemical studies in *Drosophila* cell-free lysates indicates that the mediators of RNA-dependent gene silencing are 21-25 nucleotide "small interfering" RNA duplexes (siRNAs). Accordingly, siRNA molecules are advantageously used in the compositions, complexes and methods of the present invention. The siRNAs are derived from the processing of dsRNA by an RNase known as Dicer (Bernstein, E., et al., Nature 409:363-366 (2001)). It appears that siRNA duplex products are recruited into a multi-protein siRNA complex termed RISC (RNA Induced Silencing Complex). Without wishing to be bound by any particular theory, it is believed that a RISC is guided to a target mRNA, where the siRNA duplex interacts sequence-specifically to mediate cleavage in a catalytic fashion (Bernstein, E., et al., Nature 409:363-366 (2001); Boutla, A., et al., Curr Biol 11:1776-1780 (2001); Hammond et al., 2000).

RNAi has been used to analyze gene function and to identify essential genes in mammalian cells (Elbashir, et al., Methods 26:199-213 (2002); Harborth, et al., J Cell Sci 114: 4557-4565 (2001)), including by way of non-limiting example neurons (Krichevsky, A. M. and Kosik, K. S., Proc Natl Acad Sci USA 99:11926-11929 (2002)). RNAi is also being evaluated for therapeutic modalities, such as inhibiting or block the infection, replication and/or growth of viruses, including without limitation poliovirus (Gitlin, et al, Nature 418:379-380 (2002)) and HIV (Capodici, et al., J Immunol 169:5196-5201 (2002)), and reducing expression of oncogenes (e.g., the bcr-abl gene; Scherr, et al., Blood September 26 (epub ahead of print) (2002)). RNAi has been used to modulate gene expression in mammalian (mouse) and amphibian (Xenopus) embryos (Calegari, et al., Proc Natl Acad Sci USA 99:14236-14240 (2002), and Zhou, et al., Nucleic Acids Res 30:1664-1669 (2002), respectively), and in postnatal mice (Lewis, et al., Nat Genet. 32:107-108 (2002)), and to reduce transgene expression in adult transgenic mice (McCaffrey, et al., Nature 418:38-39 (2002)).

Molecules that mediate RNAi, including without limitation siRNA, can be produced in vitro by chemical synthesis (Hohjoh, H., FEBS Lett 521:195-199 (2002)), hydrolysis of dsRNA (Yang, et al., Proc Natl Acad Sci USA 99:9942-9947 (2002)), by in vitro transcription with T7 RNA polymerase (Donze, 0. and Picard, D., Nucleic Acids Res 30:e46. (2002); Yu, et al., Proc Natl Acad Sci USA 99:6047-6052 (2002)), and by hydrolysis of double-stranded RNA using a nuclease such as *E. coli* RNase III (Yang, et al., Proc Natl Acad Sci USA 99:9942-9947 (2002)). RNAi molecules can also be expressed inside cells by endogenous RNA polymerases, using for example RNA Pol III which acts on the U6 RNA promoter (Yu, et al., Proc Natl Acad Sci USA 99:6047-6052 (2002); Paul, et al., Nat Biotechnol 20:505-508 (2002)). For example, the commercially available GeneSuppressor System (IMGENEX, San Diego, Calif.) uses vectors comprising the U6 promoter to generate RNAi molecules in vivo. Viral vectors for siRNA (Xia, et al., Nat Biotechnol 20:1006-1010 (2002)) including, by way of non-limiting example, retroviruses (Devroe, E. and Silver, P. A., BMC Biotechnol 2:15 (2002)), have also been described. Methods have been described for determining the efficacy and specificity of siRNAs in cell culture and in vivo (Bertrand, et al., Biochem Biophys Res Commun 296:1000-1004 (2002); Lassus, et al., Sci STKE 2002(147):PL13 (2002); Leirdal, M. and Sioud, M., Biochem Biophys Res Commun 295:744-748 (2002)).

Because the Dicer RNase facilitates siRNA production, it is expected that cells that express Dicer will demonstrate a quicker and/or more robust response to dsRNA-mediated RNAi, and that cells that overexpress Dicer will respond even more quickly and/or more robustly. Overexpression of Dicer may be achieved by cloning a gene for a Dicer protein (e.g., the *Drosophila* DCR-1 gene), or orthologs or homologs thereof, into an expression vector or cassette that is placed into a cell of choice. Examples of cloned DCR genes include without limitation homologs and orthologs of DCR from mice (Nicholson, R. H. and Nicholson, A. W., Mamm. Genome 13:67-73 (2002)), accession No. NM148948; humans (Nagase, T., et al., DNA Res. 6:63-70 (1999)), accession No. NM 030621; as well as the *Drosophila* Dicer-2 (DCR-2) gene (Adams, et al, Science 287:2185-2195 (2000)), accession No. NM 079054.

In another embodiment, therapeutic nucleic acid molecules (e.g. siNA molecules) delivered exogenously optimally are stable within cells until reverse transcription of the RNA has been modulated long enough to reduce the levels of the RNA transcript The nucleic acid molecules are resistant to nucleases in order to function as effective intracellular therapeutic agents. Improvements in the chemical synthesis of nucleic acid molecules described in the instant invention and in the art have expanded the ability to modify nucleic acid molecules by introducing nucleotide modifications to enhance their nuclease stability as described above.

In yet another embodiment, siNA molecules having chemical modifications that maintain or enhance enzymatic activity of proteins involved in RNAi are used. Such nucleic acids are also generally more resistant to nucleases than unmodified nucleic acids. Thus, in vitro and/or in vivo the activity should not be significantly lowered.

In one embodiment, nucleic acid molecules of the invention that act as mediators of the RNA interference gene silencing response are double-stranded nucleic acid molecules. In another embodiment, the siNA molecules of the invention consist of duplexes containing about 19 base pairs between oligonucleotides comprising about 19 to about 25 (e.g. about 19, 20, 21, 22, 23, 24 or 25) nucleotides. In yet another embodiment, siNA molecules of the invention comprise duplexes with overhanging ends of about 1 to about 3 (e.g., about 1, 2, or 3) nucleotides, for example, about 21-nucleotide duplexes with about 19 base pairs and 3'-terminal mononucleotide, dinucleotide, or trinucleotide overhangs.

In one embodiment, a siNA molecule of the invention comprises modified nucleotides while maintaining the ability to mediate RNAi. The modified nucleotides can be used to improve in vitro or in vivo characteristics such as stability, activity, and/or bioavailability. For example, a siNA molecule of the invention can comprise modified nucleotides as a percentage of the total number of nucleotides present in the siNA molecule. As such, a siNA molecule of the invention can generally comprise about 5% to about 100% modified nucleotides (e.g., 5%, 10%, 15%, 20%, 25%, 30%, 35%, 40%, 45%, 50%, 55%, 60%, 65%, 70%, 75%, 80%, 85%, 90%, 95% or 100% modified nucleotides). The actual percentage of modified nucleotides present in a given siNA molecule will depend on the total number of nucleotides present in the siNA. If the siNA molecule is single stranded, the percent modification can be based upon the total number of nucleotides present in the single stranded siNA molecules. Likewise, if the siNA molecule is double stranded, the percent modification can be based upon the total number of nucleotides present in the sense strand, antisense strand, or both the sense and antisense strands.

Short Hairpin RNAs (shRNAs)

Paddison, P. J., et al., Genes & Dev. 16:948-958 (2002) have used small RNA molecules folded into hairpins as a means to effect RNAi. Accordingly, such short hairpin RNA (shRNA) molecules are also advantageously used in the compositions, complexes and methods of the present invention. The length of the stem and loop of functional shRNAs varies; stem lengths can range anywhere from about 25 to about 30 nt, and loop size can range between 4 to about 25 nt without affecting silencing activity. While not wishing to be bound by any particular theory, it is believed that these shRNAs resemble the dsRNA products of the Dicer RNase and, in any even, have the same capacity for inhibiting expression of a specific gene.

In order to express siRNA and shRNA long-term in vivo for, by way of non-limiting example, gene therapy and developmental studies, plasmids that express these RNAs have been generated. Expression vectors that continually express siRNAs in stably transfected mammalian cells have been developed. Other plasmids have been engineered to express small hairpin RNAs (shRNAs) lacking poly (A) tails. Transcription of shRNAs is initiated at a polymerase III (pol II) promoter and is believed to be terminated at position 2 of a 4-5-thymine transcription termination site. Upon expression, shRNAs are thought to fold into a stem-loop structure with 3' UU-overhangs. Subsequently, the ends of these shRNAs are processed, converting the shRNAs into .about.21 nt siRNA-like molecules. The siRNA-like molecules can, in turn, bring about gene-specific silencing in the transfected cells, which may be, by way of non-limiting example, mammalian or human cells.

Small Temporally Regulated RNAs (stRNAs)

Another group of small RNAs suitable for use in the compositions, complexes and methods of the present invention are the small temporally regulated RNAs (stRNAs). In general, stRNAs comprise from about 20 to about 30 nt (Banerjee and Slack, Control of development timing by small temporal RNAs: A paradigm for RNA-mediated regulation of gene expression, Bioessays 24:119-129, 2002). Unlike siRNAs, stRNAs downregulate expression of a target mRNA after the initiation of translation without degrading the mRNA.

Design and Synthesis of siRNA, shRNA, stRNA, Antisense and Other Oligonucleotides One or more of the following guidelines may be used in designing the sequence of siRNA and other nucleic acids designed to bind to a target mRNA, e.g., shRNA, stRNA, antisense oligonucleotides, ribozymes, and the like, that are advantageously used in accordance with the present invention.

Nucleic acids that mediate RNAi may be synthesized in vitro using methods to produce oligonucleotides and other nucleic acids, as is described elsewhere herein. In addition, dsRNA and other molecules that mediate iRNA are available from commercial vendors, such as Ribopharma AG (Kulmach, Germany), Eurogentec (Seraing, Belgium) and Sequitur (Natick, Mass.). Eurogentec offers siRNA that has been labeled with fluorophores (e.g., HEX/TET; 5' Fluorescein, 6-FAM; 3' Fluorescein, 6-FAM; Fluorescein dT internal; 5' TAMRA, Rhodamine; 3' TAMRA, Rhodamine), and these examples of fluorescent dsRNA that can be used in the invention.

Aptamers

Traditionally, techniques for detecting and purifying target molecules have used polypeptides, such as antibodies, that specifically bind such targets. Nucleic acids have long been known to specifically bind other nucleic acids (e.g., ones having complementary sequences). However, nucleic acids that bind non-nucleic target molecules have been described and are generally referred to as aptamers. See, e.g., Blackwell, T. K, et al., Science (1990) 250:1104-1110; Blackwell, T. K, et al., Science (1990) 250:1149-1152; Tuerk, C., and Gold, L., Science (1990) 249:505-510; Joyce, G. F., Gene (1989) 82:83-87. Accordingly, nucleic acid molecules (e.g., oligonucleotides) suitable for use in the present invention also include aptamers. As applied to aptamers, the term "binding" specifically excludes the "Watson-Crick"-type binding interactions (i.e., A:T and G:C base-pairing) traditionally associated with the DNA double helix.

The term "aptamer" thus refers to a nucleic acid or a nucleic acid derivative that specifically binds to a target molecule, wherein the target molecule is either (i) not a nucleic acid, or (ii) a nucleic acid or structural element thereof that is bound by the aptatmer through mechanisms other than duplex- or triplex-type base pairing.

In general, techniques for identifying aptamers involve incubating a preselected non-nucleic acid target molecule with mixtures (2 to 50 members), pools (50 to 5,000 members) or libraries (50 or more members) of different nucleic acids that are potential aptamers under conditions that allow complexes of target molecules and aptamers to form. By "different nucleic acids" it is meant that the nucleotide sequence of each potential aptamer may be different from that of any other member, that is, the sequences of the potential aptamers are random with respect to each other. Randomness can be introduced in a variety of manners such as, e.g., mutagenesis, which can be carried out in vivo by exposing cells harboring a nucleic acid with mutagenic agents, in vitro by chemical treatment of a nucleic acid, or in vitro by biochemical replication (e.g., PCR) that is deliberately allowed to proceed under conditions that reduce fidelity of replication process; randomized chemical synthesis, i.e., by synthesizing a plurality of nucleic acids having a preselected sequence that, with regards to at least one position in the sequence, is random. By "random at a position in a preselected sequence" it is meant that a position in a sequence that is normally synthesized as, e.g., as close to 100% A as possible (e.g., 5'-C-T-T-A-G-T-3') (SEQ ID NO:1), is allowed to be randomly synthesized at that position (C-T-T-N-G-T, wherein N indicates a randomized position) (SEQ ID NO:2). At a randomized position, for example, the synthesizing reaction contains 25% each of A,T,C and G; or x % A, w % T, y % C and z % G, wherein x+w+y+z=100. The randomization at the position may be complete (i.e., x=y=w=z=25%) or stoichastic (i.e., at least one of x, w, y and z is not 25%).

In later stages of the process, the sequences are increasingly less randomized and consensus sequences may appear; in any event, it is preferred to ultimately obtain an aptamer having a unique nucleotide sequence.

Aptamers and pools of aptamers are prepared, identified, characterized and/or purified by any appropriate technique, including those utilizing in vitro synthesis, recombinant DNA techniques, PCR amplification, and the like. After their formation, target:aptamer complexes are then separated from the uncomplexed members of the nucleic acid mixture, and the nucleic acids that can be prepared from the complexes are candidate aptamers (at early stages of the technique, the aptamers generally being a population of a multiplicity of nucleotide sequences having varying degrees of specificity for the target). The resulting aptamer (mixture or pool) is then substituted for the starting apatamer (library or pool) in repeated iterations of this series of steps. When a limited number (e.g., a pool or mixture, preferably a mixture with less than 10 members, most preferably 1) of nucleic acids having satisfactory specificity is obtained, the aptamer is sequenced and characterized. Pure preparations of a given aptamer are generated by any appropriate technique (e.g., PCR amplification, in vitro chemical synthesis, and the like).

For example, Tuerk and Gold (Science (1990) 249:505-510) describe the use of a procedure termed "systematic evolution of ligands by exponential enrichment" (SELEX). In this method, pools of nucleic acid molecules that are randomized at specific positions are subjected to selection for binding to a nucleic acid-binding protein (see, e.g., PCT International Publication No. WO 91/19813 and U.S. Pat. No. 5,270,163). The oligonucleotides so obtained are sequenced and otherwise characterization. Kinzler, K. W., et al. (Nucleic Acids Res. (1989) 17:3645-3653) used a similar technique to identify synthetic double-stranded DNA molecules that are specifically bound by DNA-binding polypeptides. Ellington, A. D., et al. (Nature (1990) 346: 818-822) describe the production of a large number of random sequence RNA molecules and the selection and identification of those that bind specifically to specific dyes such as Cibacron blue.

Another technique for identifying nucleic acids that bind non-nucleic target molecules is the oligonucleotide combinatorial technique described by Ecker, D. J. et al. (Nuc. Acids Res. 21, 1853 (1993)) known as "synthetic unrandomization of randomized fragments" (SURF), which is based on repetitive synthesis and screening of increasingly simplified sets of oligonucleotide analogue libraries, pools and mixtures (Tuerk, C. and Gold, L. (Science 249, 505 (1990)). The starting library consists of oligonucleotide analogues of defined length with one position in each pool containing a known analogue and the remaining positions containing equimolar mixtures of all other analogues. With each round of synthesis and selection, the identity of at least one position of the oligomer is determined until the sequences of optimized nucleic acid ligand aptamers are discovered.

Once a particular candidate aptamer has been identified through a SURF, SELEX or any other technique, its nucleotide sequence can be determined (as is known in the art), and its three-dimensional molecular structure can be examined by nuclear magnetic resonance (NMR). These techniques are explained in relation to the determination of the three-dimensional structure of a nucleic acid ligand that binds thrombin in Padmanabhan, K. et al., J. Biol. Chem. 24, 17651 (1993); Wang, K. Y. et al., Biochemistry 32, 1899 (1993); and Macaya, R. F. et al., Proc. Nat'l. Acad. Sci. USA 90, 3745 (1993). Selected aptamers may be resynthesized using one or more modified bases, sugars or backbone linkages. Aptamers consist essentially of the minimum sequence of nucleic acid needed to confer binding specificity, but may be extended on the 5' end, the 3' end, or both, or may be otherwise derivatized or conjugated.

Oligonucleotide Synthesis

The oligonucleotides used in accordance with the present invention can be conveniently and routinely made through the well-known technique of solid-phase synthesis. Equipment for such synthesis is sold by several vendors including, for example, Applied Biosystems (Foster City, Calif.). Other methods for such synthesis that are known in the art may additionally or alternatively be employed. It is well known to use similar techniques to prepare oligonucleotides such as the phosphorothioates and alkylated derivatives. By way of non-limiting example, see, e.g., U.S. Pat. No. 4,517,338 (Multiple reactor system and method for polynucleotide synthesis) to Urdea et al., and U.S. Pat. No. 4,458,066 (Process for preparing polynucleotides) to Caruthers et al.; Lyer R P, Roland A, Zhou W, Ghosh K. Modified oligonucleotides—synthesis—, properties and applications. Curr Opin Mol. Ther. 1:344-358, 1999; Verma S, Eckstein F. Modified oligonucleotides: synthesis and strategy for users. Annu Rev Biochem. 67:99-134, 1998; Pfleiderer W, Matysiak S, Bergmann F, Schnell R. Recent progress in oligonucleotide synthesis. Acta Biochim Pol. 43:37-44, 1996; Warren W J, Vella G. Principles and methods for the analysis and purification of synthetic deoxyribonucleotides by high-performance liquid chromatography. Mol. Biotechnol. 4:179-199, 1995; Sproat B S. Chemistry and applications of oligonucleotide analogues. J. Biotechnol. 41:221-238, 1995; De Mesmaeker A, Altmann K H, Waldner A, Wendebom S. Backbone modifications in oligonucleotides and peptide nucleic acid systems. Curr Opin Struct Biol. 5:343-355, 1995; Charubala R, Pfleiderer W. Chemical synthesis of 2',5'-oligoadenylate analogues. Prog Mol Subcell Biol. 14:114-138, 1994; Sonveaux E. Protecting groups in oligonucleotide synthesis. Methods Mol. Biol. 26:1-71, 1994; Goodchild J. Conjugates of oligonucleotides and modified oligonucleotides: a review of their synthesis and properties. Bioconjug Chem. 1:165-187, 1990; Thuong N T, Asseline U. Chemical synthesis of natural and modified oligodeoxynucleotides. Biochimie. 67:673-684, 1985; Itakura K, Rossi J J, Wallace R B. Synthesis and use of synthetic oligonucleotides. Annu Rev Biochem. 53:323-356, 1984; Caruthers M H, Beaucage S L, Becker C, Efcavitch J W, Fisher E F, Galluppi G, Goldman R, deHaseth P, Matteucci M, McBride L, et al. Deoxyoligonucleotide synthesis via the phosphoramidite method. Gene Amplif Anal. 3:1-26, 1983;

Ohtsuka E, Ikehara M, Soll D. Recent developments in the chemical synthesis of polynucleotides. Nucleic Acids Res. 10:6553-6560, 1982; and Kossel H. Recent advances in polynucleotide synthesis. Fortschr Chem Org. Naturst. 32:297-508, 1975.

Oligonucleotides and other nucleic acids having accessory elements can also be prepared for advantageous use in the compositions, complexes and methods of the present invention. Some such accessory elements can specifically bind or otherwise interact with another molecule for a variety of purposes, including without limitation:

Intracellular transport. For example, a nucleotide sequence that localizes nucleic acids to mitochondria is described in U.S. Pat. No. 5,569,754;

Cellular targeting. For example, the sequence of an aptamer that binds to a cell surface molecule (e.g., a receptor, cellular adhesion protein, membrane lipid, etc.) can be included in order to direct the oligonucleotide complex to a particular type of cell;

Delivery of DNA-binding proteins. For example, a nucleotide sequence that specifically binds a transcription factor can be included in order to effect the delivery of the transcription factor at the same time as the other components of the complex;

Delivery of recombination proteins. As an example, a site that specifically binds a recombination protein can be included. The recombination protein can be a recombinase per se (e.g., lambda integrase and related site-specific recombinases) or a protein that facilitates or enhances recombination (e.g. a histonelike protein, such as Integration Host Factor, IHF). In one embodiment, a histonelike protein (e.g., IHF) and a site-specific recombinase (e.g., lambda integrase or Xis) are incorporated into one or more complexes, and cells are transfected therewith. The presence of IHF in transfected cells increases the amount of site-specific recombination mediated by the integrase, thereby promoting recombination between specific sites (e.g. attB, attP, attL, attR, etc.) on nucleic acids within the cells (Christ et al., 2002. Site-specific recombination in eukaryotic cells mediated by mutant lambda integrases: implications for synaptic complex formation and the reactivity of episomal DNA segments. J Mol Biol 319:305-314). Such cells include, without limitation, embryonic cells, such as stem cells (Christ N, Droge P. 2002. Genetic manipulation of mouse embryonic stem cells by mutant lambda integrase. Genesis 32:203-208). In another embodiment, mutants of lambda integrase that have activity in the absence of IHF are used (Lorbach et al., 2000. Site-specific recombination in human cells catalyzed by phage lambda integrase mutants. J Mol Biol 296:1175-81).

Chemical Modifications of Nucleic Acids

In certain embodiments, oligonucleotides used in accordance with the present invention may comprise one or more chemical modifications including with neither limitation nor exclusivity base modifications, sugar modifications, and backbone modifications. In addition, a variety of molecules can be conjugated to the oligonucleotides; see, e.g., the descriptions of chemical conjunction of fluorophores to oligonucleotides that are present throughout the present disclosure. Other suitable modifications include but are not limited to base modifications, sugar modifications, backbone modifications, and the like.

Base Modifications

In certain embodiments, the oligonucleotides used in the present invention can comprise one or more base modifications. For example, the base residues in aptamers may be other than naturally occurring bases (e.g., A, G, C, T, U, and the like). Derivatives of purines and pyrimidines are known in the art; an exemplary but not exhaustive list includes aziridinylcytosine, 4-acetylcytosine, 5-fluorouracil, 5-bromouracil, 5-carboxymethylaminomethyl-2-thiouracil, 5-carboxymethylaminomethyluracil, inosine (and derivatives thereof), N6-isopentenyladenine, 1-methyladenine, 1-methylpseudouracil, 1-methylguanine, 1-methylinosine, 2,2-dimethylguanine, 2-methyladenine, 2-methylguanine, 7-methylguanine, 3-methylcytosine, 5-methylcytosine (5MC), N6-methyladenine, 5-methylaminomethyluracil, 5-methoxyaminomethyl-2-thiouracil, beta-D-mannosylqueosine, 5-methoxyuracil, 2-methylthio-N-6-isopentenyladenine, uracil-5-oxyacetic acid methylester, pseudouracil, queosine, 2-thiocytosine, 5-methyl-2-thiouracil, 2-thiouracil, 4-thiouracil, 5-methyluracil, uracil-5-oxyacetic acid, and 2,6-diaminopurine. In addition to nucleic acids that incorporate one or more of such base derivatives, nucleic acids having nucleotide residues that are devoid of a purine or a pyrimidine base may also be included in oligonucleotides and other nucleic acids.

Sugar Modifications

The oligonucleotides used in the present invention can also (or alternatively) comprise one or more sugar modifications. For example, the sugar residues in oligonucleotides and other nucleic acids may be other than conventional ribose and deoxyribose residues. By way of non-limiting example, substitution at the 2'-position of the furanose residue enhances nuclease stability. An exemplary, but not exhaustive list, of modified sugar residues includes 2' substituted sugars such as 2'-O-methyl-, 2'-O-alkyl, 2'-O-allyl, 2'-S-alkyl, 2'-S-allyl, 2'-fluoro-, 2'-halo, or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and abasic nucleoside analogs such as methyl riboside, ethyl riboside or propylriboside.

Backbone Modifications

The oligonucleotides used in the present invention can also (or alternatively) comprise one or more backbone modifications. For example, chemically modified backbones of oligonucleotides and other nucleic acids include, by way of non-limiting example, phosphorothioates, chiral phosphorothioates, phosphorodithioates, phosphotriesters, aminoalkylphos-photriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotri-esters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Chemically modified backbones that do not contain a phosphorus atom have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages, including without limitation morpholino linkages; siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; and amide backbones.

Vectors and Constructs

In certain embodiments, the nucleic acid molecules of the invention are provided as vectors, particularly cloning vectors, expression vectors or gene therapy vectors. Vectors according to this aspect of the invention can be double-stranded or single-stranded and which may be DNA, RNA, or DNA/RNA hybrid molecules, in any conformation including but not limited to linear, circular, coiled, supercoiled, torsional, nicked and the like. These vectors of the invention include but are not limited to plasmid vectors and viral vectors, such as a bacteriophage, baculovirus, retrovirus, lentivirus, adenovirus, vaccinia virus, semliki forest virus and adeno-associated virus vectors, all of which are well-known and can be purchased from commercial sources (Invitrogen; Carlsbad, Calif.; Promega, Madison Wis.; Stratagene, La Jolla Calif.).

In accordance with the invention, any vector may be used to construct the cloning vectors and expression vectors of the invention. In particular, vectors known in the art and those commercially available (and variants or derivatives thereof) may in accordance with the invention be engineered to include one or more recombination sites for use in the methods of the invention. Such vectors may be obtained from, for example, Vector Laboratories Inc., Invitrogen, Promega, Novagen, NEB, Clontech, Boehringer Mannheim, Pharmacia, EpiCenter, OriGenes Technologies Inc., Stratagene, Perkin Elmer, Pharmingen, Research Genetics. General classes of vectors of particular interest include prokaryotic and/or eukaryotic cloning vectors, expression vectors, fusion vectors, two-hybrid or reverse two-hybrid vectors, shuttle vectors for use in different hosts, mutagenesis vectors, transcription vectors, vectors for receiving large inserts and the like. Other vectors of interest include viral origin vectors (M13 vectors, bacterial phage λ vectors, adenovirus vectors, and retrovirus vectors), high, low and adjustable copy number vectors, vectors which have compatible replicons for use in combination in a single host (pACYC184 and pBR322) and eukaryotic episomal replication vectors (pCDM8).

Particular vectors of interest include prokaryotic expression vectors such as pProEx-HT, pcDNA II, pSL301, pSE280, pSE380, pSE420, pTrcHisA, B, and C, pRSET A, B, and C (Invitrogen Corporation), pGEMEX-1, and pGEMEX-2 (Promega, Inc.), the pET vectors (Novagen, Inc.), pTrc99A, pKK223-3, the pGEX vectors, pEZZ18, pRIT2T, and pMC1871 (Pharmacia, Inc.), pKK233-2 and pKK388-1 (Clontech, Inc.), and variants and derivatives thereof. Vectors can also be made from eukaryotic expression vectors such as pYES2, pAC360, pBlueBacHis A, B, and C, pVL1392, pBsueBacIII, pCDM8, pcDNA1, pZeoSV, pcDNA3 pREP4, pCEP4, pEBVHis, pFastBac, pFastBac HT, pFastBac DUAL, pSFV, and pTet-Splice (Invitrogen), pEUK-C1, pPUR, pMAM, pMAMneo, pBI101, pBI121, pDR2, pCMVEBNA, and pYACneo (Clontech), pSVK3, pSVL, pMSG, pCH110, and pKK232-8 (Pharmacia, Inc.), p3' SS, pXT1, pSG5, pPbac, pMbac, pMC1neo, and pOG44 (Stratagene, Inc.), and variants or derivatives thereof.

Other vectors of particular interest include pUC18, pUC19, pBlueScript, pSPORT, cosmids, phagemids, YACs (yeast artificial chromosomes), BACs (bacterial artificial chromosomes), MACs (mammalian artificial chromosomes), HACs (human artificial chromosomes), P1 (*E. coli* phage), pQE70, pQE60, pQE9 (Qiagen), pBS vectors, PhageScript vectors, BlueScript vectors, pNH8A, pNH16A, pNH18A, pNH46A (Stratagene), pcDNA3, pSPORT1, pSPORT2, pCMVSPORT2.0 and pSV-SPORT1 (Invitrogen), pGEX, pTrsfus, pTrc99A, pET-5, pET-9, pKK223-3, pKK233-3, pDR540, pRIT5 (Pharmacia), and variants or derivatives thereof.

Additional vectors of interest include pTrxFus, pThioHis, pLEX, pTrcHis, pTrcHis2, pRSET, pBlueBacHis2, pcDNA3.1/His, pcDNA3.1(-)/Myc-His, pSecTag, pEBVHis, pPIC9K, pPIC3.5K, pAO815, pPICZ, pPICZa, pGAPZ, pGAPZa, pBlueBac4.5, pBlueBacHis2, pMelBac, pSinRep5, pSinHis, pIND, pIND(SP1), pVgRXR, pcDNA2.1. pYES2, pZErO1.1, pZErO-2.1, pCR-Blunt, pSE280, pSE380, pSE420, pVL1392, pVL1393, pCDM8, pcDNA1.1, pcDNA1.1/Amp, pcDNA3.1, pcDNA3.1/Zeo, pSe, SV2, pRc/CMV2, pRc/RSV, pREP4, pREP7, pREP8, pREP9, pREP10, pCEP4, pEBVHis, pCR3.1, pCR2.1, pCR3.1-Uni, and pCRBac from Invitrogen; λExCell, λgt11, pTrc99A, pKK223-3, pGEX-1λT, pGEX-2T, pGEX-2TK, pGEX-4T-1, pGEX4T-2, pGEX-4T-3, pGEX-3X, pGEX-5X-1, pGEX-5X-2, pGEX-5X-3, pEZZ18, pRIT2T, pMC1871, pSVK3, pSVL, pMSG, pCH110, pKK232-8, pSL1180, pNEO, and pUC4K from Pharmacia; pSCREEN-1b(+), pT7Blue(R), pT7Blue-2, pCITE-4-abc(+), pOCUS-2, pTAg, pET-32 LIC, pET-30 LIC, pBAC-2 cp LIC, pBAC-gus-2 cp LIC, pT7Blue-2 LIC, pT7Blue-2, ASCREEN-1, λBlueSTAR, pET-3abcd, pET-7abc, pET9abcd, pET11abcd, pET12abc, pET-14b, pET-15b, pET-16b, pET-17b-pET-17xb, pET-19b, pET-20b(+), pET-21abcd(+), pET-22b(+), pET-23abcd(+), pET-24abcd(+), pET-25b(+), pET-26b(+), pET-27b(+), pET-28abc(+), pET-29abc(+), pET-30abc(+), pET-31b(+), pET-32abc(+), pET-33b(+), pBAC-1, pBAC-gus-1, pBAC4x-1, pBACgus4x-1, pBAC-3 cp, p13ACgus-2 cp, pBACsurf-1, plg, Signal p1g, pYX, Selecta Vecta-Neo, Selecta Vecta—Hyg, and Selecta Vecta—Gpt from Novagen; pLexA, pB42AD, pGBT9, pAS2-1, pGAD424, pACT2, pGAD GL, pGAD GH, pGAD10, pGilda, pEZM3, pEGFP, pEGFP-1, pEGFP-N, pEGFP-C, pEBFP, pGFPuv, pGFP, p6xHis-GFP, pSEAP2-Basic, pSEAP2-Contral, pSEAP2-Promoter, pSEAP2-Enhancer, pβgal-Basic, pβgal-Control, pβgal-Promoter, pβgal-Enhancer, pCMVβ, pTet-Off, pTet-On, pTK-Hyg, pRetro-Off, pRetro-On, pIRES1neo, pIRES1hyg, pLXSN, pLNCX, pLAPSN, pMAMneo, pMAMneo-CAT, pMAMneo-LUC, pPUR, pSV2neo, pYEX 4T-1/2/3, pYEX-S1, pBacPAK-His, pBacPAK8/9, pAcUW31, BacPAK6, pTrip1Ex, λgt10, λgt11, pWE15, and λTrip1Ex from Clontech; Lambda ZAP II, pBK-CMV, pBK-RSV, pBluescript II KS .+–., pBluescript II SK .+–., pAD-GAL4, pBD-GAL4 Cam, pSurfscript, Lambda FIX II, Lambda DASH, Lambda EMBL3, Lambda EMBL4, SuperCos, pCR-Scrigt Amp, pCR-Script Cam, pCR-Script Direct, pBS .+–., pBC KS .+–., pBC SK .+–., Phagescript, pCAL-n-EK, pCAL-n, pCAL-c, pCAL-kc, pET-3abcd, pET-11abcd, pSPUTK, pESP-1, pCMVLacI, pOPRSVI/MCS, pOPI3 CAT, pXT1, pSG5, pPbac, pMbac, pMC1neo, pMC1neo Poly A, pOG44, pOG45, PFRTβGAL, pNEOβGAL, pRS403, pRS404, pRS405, pRS406, pRS413, pRS414, pRS415, and pRS416 from Stratagene.

Two-hybrid and reverse two-hybrid vectors of particular interest include pPC86, pDBLeu, pDBTrp, pPC97, p2.5, pGAD1-3, pGAD10, pACt, pACT2, pGADGL, pGADGH, pAS2-1, pGAD424, pGBT8, pGBT9, pGAD-GAL4, pLexA, pBD-GAL4, pHISi, pHISi-1, placZi, pB42AD, pDG202, pJK202, pJG4-5, pNLexA, pYESTrp and variants or derivatives thereof. Other suitable vectors will be readily apparent to the skilled artisan.

Cloning Vectors

Cloning vectors according to the invention include plasmids, cosmids, viral or phage DNA molecules or other DNA molecules that are capable of autonomous replication in a host cell, via splicing of vector-borne nucleic acid into the genetic material (chromosomal or extrachromosomal) of the host cell without loss of an essential biological function of the vector, thereby facilitating the replication and cloning of the vector. The cloning vector may further contain a marker suitable for use in the identification of cells transformed with the cloning vector. Markers may be, for example, antibiotic resistance genes, e.g., tetracycline resistance or ampicillin resistance. Clearly, methods of inserting a desired nucleic acid fragment which do not require the use of homologous recombination, transpositions or restriction enzymes (such as, but not limited to, UDG cloning of PCR fragments (U.S. Pat. No. 5,334,575, entirely incorporated herein by reference), T:A cloning, and the like) can also be applied to clone a fragment into a cloning vector to be used according to the present invention. The cloning vector can further contain one or more selectable markers suitable for use in the identification of cells transformed with the cloning vector.

Expression Vectors

Expression vectors according to the invention include vectors that are capable of enhancing the expression of one or more genes that have been inserted or cloned into the vector, upon transformation of the vector into a host. The cloned gene is usually placed under the control of (i.e., operably linked to) certain transcriptional regulatory sequences such as promoter sequences. In certain preferred embodiments in this regard, the vectors provide for specific expression, which may be inducible and/or cell type-specific. Particularly preferred among such vectors are those inducible by environmental factors that are easy to manipulate, such as temperature and nutrient additives. Expression vectors useful in the present invention include chromosomal-, episomal- and virus-derived vectors, e.g., vectors derived from bacterial plasmids or bacteriophages, and vectors derived from combinations thereof, such as cosmids and phagemids.

To produce expression vectors according to this aspect of the invention, one or more gene-containing nucleic acid molecules or oligonucleotide inserts should be operatively linked to an appropriate promoter in the vector (which may be provided by the vector itself (i.e., a "homologous promoter") or may be exogenous to the vector (i.e., a "heterologous promoter), such as the phage lambda $P_L$ promoter, the *E. coli* lac, trp and tac promoters, and the like. Other suitable promoters will be known to the skilled artisan. The gene fusion constructs will further contain sites for transcription initiation, termination and, in the transcribed region, a ribosome binding site for translation. The coding portion of the mature transcripts expressed by the constructs will preferably include a translation initiation codon at the beginning, and a termination codon (UAA, UGA or UAG) appropriately positioned at the end, of the polynucleotide to be translated. The expression vectors also preferably include at least one selectable marker. Such markers include tetracycline or ampicillin resistance genes for culturing in *E. coli* and other bacteria.

Vectors, Compositions and Methods for Gene Therapy

In additional embodiments, the invention provides compositions comprising one or more genetic constructs, including vectors (such as the expression or cloning vectors described above), or one or more of the complexes of the invention, that may be useful in delivering nucleic acid molecules to cells, tissues, organs and organisms for therapeutic or prophylactic purposes. The invention further provides methods for preparing nucleic acid molecules having regions of viral nucleic acids, as well as nucleic acid molecules prepared by such methods and compositions comprising these nucleic acid molecules, useful for the nucleic acid delivery and therapeutic/prophylactic purposes described above and in more detail below.

In one embodiment, the present invention provides methods for treating or preventing a physical disorder in an animal that is suffering from or predisposed to the physical disorder, comprising introducing into the animal one or more of the nucleic acid molecules, complexes or compositions of the invention. According to the invention, an animal, particularly a mammal (preferably a human) that is suffering from, or that is predisposed or susceptible to, a physical disorder may be treated by administering to the animal an effective dose of one or more of the nucleic acid molecules, complexes or compositions of the invention, optionally in combination with a pharmaceutically acceptable carrier or excipient therefor. As used herein, an animal that is "suffering from" a particular physical disorder is defined as an animal that exhibits one or more overt physical symptoms of the disorder that are typically used in the diagnosis or identification of the disorder according to established medical and veterinary procedures and protocols that will be familiar to the ordinarily skilled artisan. Analogously, as used herein, an animal that is "predisposed to" or "susceptible to" a physical disorder is defined as an animal that does not exhibit a plurality of overt physical symptoms of the disorder but that is genetically, physiologically or otherwise at risk for developing the disorder under appropriate physiological and environmental conditions. Hence, whether or not a particular animal is "suffering from," "predisposed to" or "susceptible to" a particular physical disorder will be apparent to the ordinarily skilled artisan upon determination of the medical history of the animal using methods that are routine in the medical and veterinary arts.

Physical disorders treatable or preventable with the compositions and methods of the present invention include any physical disorder that may be delayed, prevented, cured or otherwise treated by modulating immune system function, particularly activation and/or apoptosis in antigen-presenting cells, in an animal suffering from, or predisposed or susceptible to, the physical disorder. Such physical disorders that may be treatable or preventable using the compositions, complexes and methods of the present invention include, but are not limited to, infectious diseases (particularly bacterial diseases (including without limitation meningitis, pneumonia, tetanus, cholera, typhoid fever, staphylococcal skin infections, streptococcal pharyngitis, scarlet fever, pertussis, diphtheria, tuberculosis, leprosy, rickettsial diseases, bacteremia, bacterial venereal diseases and the like), viral diseases (including without limitation meningitis, AIDS, influenza, rhinitis, hepatitis, polio, pneumonia, yellow fever, Lassa fever, Ebola fever and the like), and/or fungal diseases (including without limitation cryptococcosis, blastomycosis, mucormycosis, histoplasmosis, aspergillosis, and the like), parasitic diseases (including without limitation malaria, Leishmaniasis, filariasis, trypanasomiasis, schistosomiasis, and the like), cancers (such as carcinomas, melanomas, sarcomas, leukemias and the like), and other disorders treatable or preventable using the methods and compositions of the present invention. Analogously, physical disorders that may be treatable or preventable using the present compositions and methods include, but are not limited to, immune system disorders (such as rheumatoid arthritis, multiple sclerosis, systemic lupus erythematosis, Crohn's Disease), and other disorders of analogous etiology. The compositions and methods of the present invention may also be used in the prevention of disease progression, such as in chemoprevention of the progression of a premalignant lesion to a malignant lesion, and to treat an animal suffering from, or predisposed to, other physical disorders that respond to treatment with compositions that activate, or inhibit/delay/prevent or induce apoptosis in, antigen-presenting cells.

In a first such aspect of the invention, the animal suffering from or predisposed to a physical disorder may be treated by introducing into the animal one or more of the nucleic acid molecules of the invention, optionally in the form of a vector and further optionally in the form of a polypeptide-nucleic acid complex of the invention (or a composition of the invention comprising one or more such complexes). This approach, known generically as "gene therapy," is designed to increase the level of expression of a given gene, generally contained on the nucleic acid molecule and/or in the administered complex, in the cells and/or tissues of the animal, thereby inhibiting, delaying or preventing the progression and/or development of the physical disorder, or to induce the reversal, amelioration or remission of one or more overt symptoms or processes of the physical disorder. Analogous gene therapy approaches have proven effective or to have promise in the treatment of a variety of mammalian diseases such as cystic fibrosis (Drum M. L. et al., Cell 62:1227-1233 (1990); Gregory, R. J. et al., Nature 347:358-363 (1990); Rich, D. P. et al., Nature 347:358-363 (1990)), Gaucher disease (Sorge, J. et al., Proc. Natl. Acad. Sci. USA 84:906-909 (1987); Fink, J. K. et al., Proc. Natl. Acad. Sci. USA 87:2334-2338 (1990)), certain forms of hemophilia (Bontempo, F. A. et al., Blood 69:1721-1724 (1987); Palmer, T. D. et al., Blood 73:438-445 (1989); Axelrod, J. H. et al., Proc. Natl. Acad. Sci. USA 87:5173-5177 (1990); Armentano, D. et al., Proc. Natl. Acad. Sci. USA 87:6141-6145 (1990)) and muscular dystrophy (Partridge, T. A. et al., Nature 337:176-179 (1989); Law, P. K. et al., Lancet 336:114-115 (1990); Morgan, J. E. et al., J. Cell Biol. 111:2437-2449 (1990)), and certain cancers such as metastatic melanoma (Rosenberg, S. A. et al., Science 233: 1318-1321 (1986); Rosenberg, S. A. et al., N. Eng. J. Med. 319:1676-1680 (1988); Rosenberg, S. A. et al., N. Eng. J. Med. 323:570-578 (1990)).

In carrying out such gene therapy methods of the invention, a variety of vectors, particularly viral vectors, are useful in forming the complexes and compositions of the invention. For example, adenoviruses are especially attractive vehicles for delivering genes to or via respiratory epithelia and the use of such vectors are included within the scope of the invention. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993), present a review of adenovirus-based gene therapy. Bout et al., Human Gene Therapy 5:3-10 (1994), demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest 91:225-234 (1993); PCT Publication Nos. WO94/12649 and WO 96/17053; U.S. Pat. No. 5,998,205; and Wang et al., Gene Therapy 2:775-783 (1995), the disclosures of all of which are incorporated herein by reference in their entireties. Adeno-associated viruses (AAV) and Herpes viruses, as well as vectors prepared from these viruses have also been proposed for use in gene therapy (Walsh et al., 1993, Proc. Soc. Exp. Biol. Med. 204:289-300; U.S. Pat. No. 5,436, 146; Wagstaff et al., Gene Ther. 5:1566-70 (1998)). Herpes viral vectors are particularly useful for applications where gene expression is desired in nerve cells.

In a preferred such approach, one or more nucleic acid and/or one or more polypeptide of the present invention within the polymer complexes of the invention, is introduced into or administered to the animal that is suffering from or predisposed to the physical disorder. Such nucleic acid molecules may be incorporated into a vector or virion suitable for introducing the nucleic acid molecules into the cells or tissues of the animal to be treated, to form a transfection vector. Suitable vectors or virions for this purpose include those derived from retroviruses, adenoviruses, alphaviruses, herpes viruses and adeno-associated viruses. As one of ordinary skill will readily recognize, the complexes of the invention also optionally may be combined with one or more pharmaceutically acceptable excipients or diluents to form a pharmaceutical composition suitable for use in these methods of the invention.

In addition, general methods for construction of gene therapy vectors and the introduction thereof into affected animals for therapeutic purposes may be obtained in the above-referenced publications, the disclosures of which are specifically incorporated herein by reference in their entirety. In one such general method, vectors comprising the nucleic acid molecules of the present invention are directly introduced into the cells or tissues of the affected animal, preferably by injection, inhalation, ingestion or introduction into a mucous membrane via solution; such an approach is generally referred to as "in vivo" gene therapy. Alternatively, cells, tissues or organs, particularly those containing one or more defective or nonfunctioning genes, containing pathological agents (e.g., bacteria, viruses, parasites, yeasts, etc.), or containing cancer cells or tumors, may be removed from the affected animal and placed into culture according to methods that are well-known to one of ordinary skill in the art. The vectors comprising the nucleic acid molecules of the invention, typically comprising one or more therapeutic genes or nucleic acid sequences, may then be introduced into these cells or tissues by any of the methods described generally above for introducing oligonucleotides into a cell or tissue, and, after a sufficient amount of time to allow incorporation of the oligonucleotides, the cells or tissues may then be re-inserted into the affected animal. Since the introduction of the therapeutic genese or nucleic acid sequences is performed outside of the body of the affected animal, this approach is generally referred to as "ex vivo" gene therapy.

For both in vivo and ex vivo gene therapy, the nucleic acid molecules (e.g., oligonucleotides) of the invention may alternatively be operatively linked to a regulatory DNA sequence, which may be a promoter or an enhancer, or a heterologous regulatory DNA sequence such as a promoter or enhancer derived from a gene, cell or organism different from that used as the source of the nucleic acid molecule being used in gene therapy, to form a genetic construct as described above. This genetic construct may then be inserted into a vector, which is then directly introduced into the affected animal in an in vivo gene therapy approach, or into the cells or tissues of the affected animal in an ex vivo approach. In another embodiment, the genetic construct of the invention may be introduced into the cells or tissues of the animal, either in vivo or ex vivo, in a molecular conjugate with a virus (e.g., an adenovirus or an adeno-associated virus) or viral components (e.g., viral capsid proteins; see WO 93/07283). In yet another embodiment, the genetic construct of the invention may be introduced into the animal in the form of a polypeptide-nucleic acid complex of the invention. Alternatively, transfected host cells, which may be homologous or heterologous, may be encapsulated within a semi-permeable barrier device and implanted into the affected animal, allowing passage of one or more therapeutic polypeptides encoded by the nucleic acid molecules in the conjugate or complex of the invention into the tissues and circulation of the animal, but preventing contact between the animal's immune system and the transfected cells (see WO 93/09222). These approaches result in increased production of one or more therapeutic polypeptides by the treated animal via (a) random insertion of the therapeutic gene (contained on the nucleic acid molecule of the invention) into the host cell genome; or (b) incorporation of the therapeutic gene into the nucleus of the cells where it may exist as an extrachromosomal genetic element. General descriptions of such methods and approaches to gene therapy may be found, for example, in U.S. Pat. No. 5,578,461; WO 94/12650; and WO 93/09222; the disclosures of all of which are incorporated herein by reference in their entireties.

Release of Nucleic Acids Intracellularly

Once internatlized into a cell (typically via endocytosis), transfected nucleic acids are usually sequestered within lipid membrane-enclosed vesicles (including endosomes, as well as components of the endoplasmic reticulum (ER) and/or Golgi apparatus). The release of nucleic acids into the cytosol from endosomes, the ER or the Golgi enhances transfection. Endosomal disrupting agents can be used in the context of the invention and are defined herein as agents that cause or enhance the release of nucleic acids into the cytosol. Endosomal disrupting agents can act, by way of non-limiting example, by disrupting membranes of endosomes, the ER, the Golgi apparatus and/or other membranes; blocking or reducing endosome fusion to lysosomes; and/or altering, preferably raising, the pH of endosomes. The pH of an endosome is generally lower than that of the cytosol by one to two pH units. This pH gradient can be exploited for cellular delivery using agents that disrupt lipid bilayer membranes at pH 6.5 and below (Asokan A, Cho M J. 2002.

Exploitation of intracellular pH gradients in the cellular delivery of macromolecules. J Pharm Sci 91:903-913).

Membrane-disruptive pH-sensitive synthetic polymers have been described and include by way of non-limiting example poly(amidoamine)s (PAAs) (Pattrick et al., 2001. Poly(amidoamine)-mediated intracytoplasmic delivery of ricin A-chain and gelonin. J Control Release 77:225-32; U.S. Pat. No. 6,413,941); poly(propylacrylic acid) (PPAA) (Kyrialides et al., 2002. pH-sensitive polymers that enhance intracellular drug delivery in vivo. J Control Release 78:295-303); and poly(ethyl acrylic acid) (PEAAc) (Murthy et al., 1999. The design and synthesis of polymers for eukaryotic membrane disruption. J Control Release 61:137-43).

Some cationic lipid transfection reagents, such as vectamidine and DMRIE-C, may have inherent endosomal disrupting properties. See El Ouahabi et al., 1997. The role of endosome destabilizing activity in the gene transfer process mediated by cationic lipids. FEBS Lett 414:187-92. Moreover, cationic lipids that are acid-labile have been described (Boomer et al., 2002. Formation of plasmid-based transfection complexes with an acid-labile cationic lipid: characterization of in vitro and in vivo gene transfer. Pharm Res 19:1292-1301; Wetzer et al., 2001. Reducible cationic lipids for gene transfer. Biochem J 356:747-756).

Other endosome disrupting agents include viral fusogenic peptides, including without limitation influenza virus hemagglutinin fusogenic peptides (Bongartz et al., 1994. Improved biological activity of antisense oligonucleotides conjugated to a fusogenic peptide. Nucleic Acids Res 22:4681-4688) and synthetic derivatives thereof (Plank et al., 1994. The influence of endosome-disruptive peptides on gene transfer using synthetic virus-like gene transfer systems. J. Biol. Chem. 269: 12918-12924. These peptides are thought to change conformation at acidic pH and destabilize endosomal membranes.

The ricin A chain, which is capable of penetrating out of endosomes and into the cytosol, can be attached to a nucleic acid or protein to in order to effect the endosomal release thereof (Beaumell et al., 1993. ATP-dependent translocation of ricin across the membrane of purified endosomes J. Biol. Chem. 268:23661-23669).

Agents that alter the pH of endosomes can be used to practice the invention. Lysosomotropic amines are generally thought to effect of raising the pH of endosomes. Such agents include without limitation ammonium chloride, 4-aminoquinolines (e.g., chloroquine, amodiaquine), 8-aminoquinolines (e.g., primaquine and WR242511), pyrimethamine, quinacrine, quinine and quinidine (Tsiang H, Superti F. Ammonium chloride and chloroquine inhibit rabies virus infection in neuroblastoma cells. Brief report. Arch Virol 81:377-382; Deshpande et al., 1997. Efficacy of certain quinolines as pharmacological antagonists in botulinum neurotoxin poisoning. Toxicon 35:433-445).

Artificial Chromosomes

The nucleic acid molecules used in the compositions, complexes and methods of the present invention may alternatively be in the form of artificial chromosomes (ACs). An AC is a DNA molecule that comprises, at a minimum, at least one origin of DNA replication (ori), one or more telomeres and a centromere. Each ori is preferably derived from a genomic chromosome, so that replication of the AC is coordinated with cellular DNA replication. The telomeres are elements that preserve the terminal sequences of chromosomes for any number of rounds of replication and cell division. The centromere mediates proper segregation of the AC through each cell division (Willard H F. Centromeres: the missing link in the development of human artificial chromosomes. Curr Opin Genet Dev 8:219-225, 1998).

Ideally, ACs are stably maintained and are properly segregated during both mitosis and meiosis. Generally, an AC contains a segment of cloned DNA, and is usually more stable the larger the piece of cloned DNA. It is possible to engineer ACs to improve or add functions (Grimes B, Cooke H. Engineering mammalian chromosomes. Hum Mol Genet. 7:1635-1640, 1998; Saffery R, Choo K H. Strategies for engineering human chromosomes with therapeutic potential. J Gene Med 4:5-13, 2002).

Bacterial and yeast artificial chromosomes (BACs and YACs, respectively) have been described. BACs and YACs are reviewed in Shizuya H, Kouros-Mehr H. The development and applications of the bacterial artificial chromosome cloning system. Keio J Med 50:26-30, 2001; and Fabb S A, Ragoussis J. Yeast artificial chromosome vectors. Mol Cell Biol Hum Dis Ser 5:104-124, 1995; Anand R. Yeast artificial chromosomes (YACs) and the analysis of complex genomes, Trends Biotechnol 10:35-40, 1992.

Mammalian artificial chromosomes (MACs) have been prepared and may be used as vectors for somatic gene therapy. See Brown W R. Mammalian artificial chromosomes. Curr Opin Genet Dev 2:479-486, 1992; Huxley C. Mammalian artificial chromosomes and chromosome transgenics. Trends Genet 13:345-347, 1997; Ascenzioni F, Donini P, Lipps H J. Mammalian artificial chromosomes—vectors for somatic gene therapy. Cancer Lett 118:135-142, 1997; Vos J M. Mammalian artificial chromosomes as tools for gene therapy. Curr Opin Genet Dev 8:351-359, 1998; and Vos J M. Therapeutic mammalian artificial episomal chromosomes. Curr Opin Mol Ther 1:204-215, 1999.

Human artificial chromosomes (HACS) have been described (Henning K A, Novotny E A, Compton S T, Guan X Y, Liu P P, Ashlock M A. Human artificial chromosomes generated by modification of a yeast artificial chromosome containing both human alpha satellite and single-copy DNA sequences. Proc Natl Acad Sci USA. 96:592-597, 1999; Larin Z, Mejia J E. Advances inhuman artificial chromosome technology. Trends Genet 18:313-319, 2002). HACs include but are not limited to satellite DNA-based artificial chromosomes (SATACs). SATACs have been made by mixing human telomeric DNA, genomic DNA, and arrays of repetitive α-satellite DNA having centromeric activity (Hadlaczky G. Satellite DNA-based artificial chromosomes for use in gene therapy. Curr Opin Mol Ther. 3:125-132, 2001).

In addition to gene therapy, ACs have been used to stably clone large pieces of DNA in a variety of cell types (Schlessinger D, Nagaraja R. Impact and implications of yeast and human artificial chromosomes. Ann Med 30:186-191, 1998; Monaco A P, Larin Z. YACs, BACs, PACs and MACs: artificial chromosomes as research tools. Trends Biotechnol. 12:280-286, 1994). In addition, ACs can be also be used in transgenic animal technologies to introduce large transgenes in animals, especially human transgenes in mouse models of human genetic diseases. See Giraldo P, Montoliu L. Size matters: use of YACs, BACs and PACs in transgenic animals. Transgenic Res 10:83-103, 2001; Jakobovits A, Lamb B T, Peterson K R. Production of transgenic mice with yeast artificial chromosomes. Methods Mol Biol 136:435-453, 2000; Lamb B T, Gearhart J D. YAC transgenics and the study of genetics and human disease. Curr Opin Genet Dev 5:342-348, 1995; Jakobovits A. YAC vectors. Humanizing the mouse genome. Curr Biol 4:761-763, 1994; Huxley C. Transfer of YACs to mammalian cells and transgenic mice. Genet Eng (N Y) 16:65-91, 1994; Huxley C, Gnirke A. Transfer of yeast artificial chromosomes from yeast to mammalian cells. Bioessays 13:545-550, 1991; and Heintz N. BAC to the future: the use of bac transgenic mice for neuroscience research. Nat Rev Neurosci 2:861-870, 2001.

Peptide Nucleic Acids (PNAs)

The nucleic acid molecules used in the delivery compositions, complexes and methods of the present invention may alternatively be in the form of peptide nucleic acids (PNAs). PNAs are analogs of nucleic acid molecules in which the backbone is a pseudopeptide rather than a sugar. Like DNA and RNA, a PNA molecule binds single-stranded nucleic acid having a reverse complementary sequence; however, the neutral backbone of PNAs can result in stronger binding and greater specificity. For a review, see Corey D R. Peptide nucleic acids: expanding the scope of nucleic acid recognition. Trends Biotechnol 15:224-229, 1997. The synthesis of PNAs is reviewed by Hyrup et al. (Peptide nucleic acids (PNA): synthesis, properties and potential applications. Bioorg Med Chem. 4:5-23, 1996). For exemplary protocols for making and using PNAs, see Peptide Nucleic Acids: Protocols and Applications, Nielsen, P. E. and Egholm, M., eds. Horizon Scientific Press, Norfolk, U.K. 1999. PNAs can be prepared according to methods known in the art or purchased commercially from, e.g., Monomer Sciences Inc. (New Market, Ala., U.S.) and Dalton Chemical Laboratories Inc. (Toronto, ON, Canada). Methods for attaching fluorescent moieties to PNA have been described. See, e.g., Murakami et al., A novel method for detecting HIV-1 by non-radioactive in situ hybridization: application of a peptide nucleic acid probe and catalysed signal amplification. Pathol 194:130-135, 2001.

Fluorescent Molecules and Moieties

In certain embodiments, the compositions and polymer complexes of the invention will comprise one or more marker or activation molecules or moieties, such as one or more molecules or moieties that are linked to, complexed with, or comprise, one or more fluorophores. Contemplated by this aspect of the invention are compositions in which the one or more fluorophores is linked (e.g., bound covalently or ionically) to one or more components of the compositions of the invention (e.g., fluorescently tagged nucleic acid molecules, nucleotides, proteins, peptides, and the like). Also contemplated by this aspect of the invention are compositions in which the one or more fluorophores is contained separately within the composition, without necessarily being directly linked to one or more of the other components within the composition.

Fluorophores

For the purpose of the present invention, a fluorophore can be a substance which itself fluoresces, or a substance that fluoresces in particular situations (e.g., when in proximity to another fluorophore, as occurs in FRET). The term "fluorophore" or "fluor" is meant to encompass fluorescent moieties that are covalently linked to another molecule, fluorescent molecules that are non-covalently attached to another molecule, as well as free fluorescent molecules. Molecules that become fluorescent only after attachment to another molecule, such as a peptide or nucleic acid, are also within the scope of the invention.

In principal, any fluorophore now known, or later discovered, can be used in accordance with the methods, compositions and kits of the present invention. In certain embodiments, fluorophores suitable for use in the present invention include those that are excitable at, and/or emit fluorescence at, a wavelength falling within the range of wavelengths from about 200 nm to about 800 nm; from about 250 nm to about 800 nm; from about 250 nm to about 750 nm; from about 300 nm to about 700 nm; from about 350 nm to about 650 nm; from about 400 nm to about 600 nm; from about 450 nm to about 600 nm; from about 450 nm to about 580 nm; from about 450 nm to about 575 nm; from about 450 nm to about 570 nm; from about 500 nm to about 600 nm; from about 500 nm to about 590 nm; from about 500 nm to about 580 nm; from about 500 nm to about 575 nm; from about 500 nm to about 570 nm; and the like. As one of ordinary skill will readily appreciate, any fluorophore with an excitation maximum and an emission maximum within the recited ranges is suitable for use in accordance with the present invention, whether or not the actual, specific excitation and emission maxima for that given fluorophore are specifically set forth above.

In view of the availability of an array of appropriate compounds, it is well within the capabilities of one skilled in the art to choose a reactive fluorescent molecule or set of molecules that is appropriate to the practice of the present invention, given the above-noted guidelines for excitation and emission maxima. Many appropriate fluorophores are commercially available from sources such as Molecular Probes Inc. (Eugene, Oreg.).

Many of these methods are quite appropriate for use in preparing the various compounds required to practice the present invention. One skilled in the art will be able, without undue experimentation, to choose a suitable method for preparing a desired fluorescently labeled nucleic acid, oligonucleotide or the like. See, for example, Protocols for Oligonucleotide Conjugates, Vol. 26 of Methods in Molecular Biology, Agrawal, ed., Humana Press, Totowa, N.J. (1994). Additionally, as the art of organic synthesis, particularly in the area of nucleic acid chemistry, continues to expand in scope new methods will be developed which are equally as suitable as those now known. The following discussion is offered as representative of the array of compounds and techniques that can be used to modify nucleic acids. Methods useful in conjunction with the present invention are not to be construed as limited by this discussion.

Fluorescent moieties and molecules useful in practicing the present invention include but are not limited to derivatives of fluorescein, rhodamine, coumarin, dimethylaminonaphthalene sulfonic acid (dansyl), pyrene, anthracene, nitrobenzoxadiazole (NBD), acridine and dipyrrometheneboron difluoride. More specifically, non-limiting examples of fluorescent moieties and molecules useful in practicing the present invention include, but are not limited to: carbocyanine, dicarbocyanine, merocyanine and other cyanine dyes (e.g., CyDye fluorophores, such as Cy3, Cy3.5, Cy5, Cy5.5 and Cy7 from Pharmacia). These dyes have a maximum fluorescence at a variety of wavelengths: green (506 nm and 520 nm), green-yellow (540 nm), orange (570 nm), scarlet (596 nm), far-red (670 nm), and near infrared (694 nm and 767 nm); coumarin and its derivatives (e.g., 7-amino-4-methylcoumarin, aminocoumarin and hydroxycoumarin); BODIPY dyes (e.g., BODIPY FL, BODIPY 630/650, BODIPY 650/665, BODIPY); fluorescein and its derivatives (e.g., fluorescein isothiocyanate); rhodamine dyes (e.g. rhodamine green, rhodamine red, tetramethylrhodamine, rhodamine 6G and Lissamine rhodamine B); Alexa dyes (e.g., Alexa Fluor-350, -430, -488, -532, -546, -568, -594, -663 and -660, from Molecular Probes); fluorescent energy transfer dyes (e.g., thiazole orange-ethidium heterodimer, TOTAB, etc.); proteins with luminescent properties, e.g.: green fluorescent protein (GFP) and mutants and variants thereof, including by way of non-limiting example fluorescent proteins having altered wavelengths (e.g., YFP, RFP, etc.). See Chiesa et al. (2001). Recombinant aequorin and green fluorescent protein as valuable tools in the study of cell signalling. Biochem J. 355:1-12; Sacchetti et al. (2000). The molecular determinants of the efficiency of green fluorescent protein mutants. Histol Histopathol. 15:101-107; Larrick et al. (1995). Green fluorescent protein: untapped potential in immunotechnology. Immunotechnology 1:83-86); aequorin and mutants and variants thereof; DsRed protein (Baird et al., 2000. Biochemistry, mutagenesis, and oligomerization of DsRed, a red fluorescent protein from coral. Proc Natl Acad Sci USA 97:11984-9), and mutants and variants thereof (see Verkhusha et al., 2001. An enhanced mutant of red fluorescent protein DsRed for double labeling and developmental timer of neural fiber bundle formation. J Biol Chem 276:29621-4; Bevis B J, Glick B S., 2002. Rapidly maturing variants of the Discosoma red fluorescent protein (DsRed). Nat Biotechnol 20:83-87; Terskikh et al., 2002. Analysis of DsRed Mutants. Space around the fluorophore accelerates fluorescence development. J Biol Chem 277:7633-6; Campbell et al., 2002. A monomeric red fluorescent protein. Proc Natl Acad Sci USA 99:7877-82; and Knop et al., 2002. Improved version of the red fluorescent protein (drFP583/DsRed/RFP). Biotechniques 33:592, 594, 596-598); and other fluors, e.g., 6-FAM, HEX, TET, F12-dUTP, L5-dCTP, 8-anilino-1-napthalene sulfonate, pyrene, ethenoadenosine, ethidium bromide prollavine monosemicarbazide, p-terphenyl, 2,5-diphenyl-1,3,4-oxadiazole, 2,5-diphenyloxazole, p-bis[2-(5-phenyloxazolyl)]benzene, 1,4-bis-2-(4-methyl-5-phenyloxazolyl)-1-benzene, lanthanide chelates, Pacific blue, Cascade blue, Cascade Yellow, Oregon Green, Marina Blue, Texas Red, phycoerythrin, eosins and erythrosins; as well as derivatives of any of the preceding molecules and moieties. Fluorophores, and kits for attaching fluorophores to nucleic acids and peptides, are commercially available from, e.g., Molecular Probes (Eugene, Oreg.) and Sigma/Aldrich (St Louis, Mo.).

Fluorescent Oligonucleotides and Other Nucleic Acids

Fluorescent moieties useful in practicing the present invention can be attached to any location on a nucleic acid, including sites on the base segment and sites on the sugar segment. Thus, the fluorophore is covalently attached to a nucleic acid at a position selected from the group consisting of the 3'-terminus, the 5'-terminus, an internal position and combinations thereof. See, generally, Goodchild, Bioconjug. Chem. 1:165-187 (1990). Although any suitable fluorophore can be associated with an oligonucleotide, some of the more commonly used ones are fluorescein, tetramethylrhodamine, Texas Red and Lissamine rhodamine B.

A number of techniques have been developed for converting specific constituents of DNA and RNA strands into fluorescent adducts. For a review, see, Leonard and Tolman, in "Chemistry, Biology and Clinical Uses of Nucleoside Analogs," A. Bloch, ed., Ann. N.Y. Acad. Sci. 255:43-58 (1975).

Fluorescent G derivatives have also been prepared from the natural base upon its reaction with variously substituted malondialdehydes. See, Leonard and Tolman, in "Chemistry, Biology and Clinical Uses of Nucleoside Analogs," A. Bloch, ed., Ann. N.Y. Acad. Sci. 255:43-58 (1975).

In addition to the various methods for converting the bases of an intact oligonucleotide into their fluorescent analogs, there are a number of methods for introducing fluorescence into an oligonucleotide during its de novo synthesis.

Fluorescent Peptides, Polypeptides and Proteins

Fluorescent moieties useful in practicing the present invention can be attached to any location on a peptide or protein, including sites on the N-terminus, the C-terminus, a side group, an internal position and combinations thereof.

By way of non-limiting example, a highly fluorescent molecule can be chemically linked to a native amino acid group. The chemical modification occurs on the amino acid side-chain, leaving the carboxyl and amino functionalities free to participate in a polypeptide bond formation. Highly fluorescent dansyl chloride can be linked to the nucleophilic side chains of a variety of amino acids including lysine, arginine, tyrosine, cysteine, histidine, etc., mainly as a sulfonamide for amino groups or sulfate bonds to yield fluorescent derivatives. Such derivatization leaves the ability to form peptide bond intact, allowing for the incorporation of dansyllysine into a protein.

More specifically, non-limiting examples of fluorescent moieties and molecules useful in practicing the present invention include amine-reactive fluorophores, which can react with the N-terminus of a peptide or a side group of an amino acid residue. These include without limitation fluorophores associated with succinimidyl esters and carboxylic acids thereof; aldehydes; sulfonyl chlorides, e.g., dansyl, pyrene, Lissamine rhodamine B and Texas Red derivatives; and arylating reagents (e.g., NBD chloride, NBD fluoride and dichlorotriazines).

Fluorescamine is intrinsically nonfluorescent but reacts rapidly with primary aliphatic amines, including those in peptides and proteins, to yield a blue-green-fluorescent derivative. The aromatic dialdehydes o-phthaldialdehyde (OPA) and naphthalene-2,3-dicarboxaldehyde (NDA) are essentially nonfluorescent until reacted with a primary amine to yield a fluorescent isoindole. Sulfonyl chlorides, including dansyl chloride, 1-pyrenesulfonyl chloride and dapoxylsulfonyl chloride, react with amines to yield blue- or blue-green-fluorescent sulfonamides. FITC and benzofuran isothiocyanates can be used. A unique method for specific derivatization of the N-terminus of peptides by FITC has been described ("Attachment of a single fluorescent label to peptides for determination by capillary zone electrophoresis." Zhao J Y, Waldron K C, Miller J, Zhang J Z, Harke H, Dovichi N J. J Chromatogr 608, 239-242, 1992). N-methylisatoic anhydride and the succinimidyl ester of N-methylanthranilic acid can be used to prepare esters or amides of the small N-methylanthranilic acid fluorophore. The small size of this fluorophore should reduce the likelihood that the label will interfere with the function of the protein.

The type of fluorophore, the site of its attachment to the peptide, the type of linker used to attach the fluorophore and the site of attachment of the peptide to the fluorophore can affect the efficiency of cellular delivery and/or light-induced release of components from the complex. Specifically for fluorescein and fluorescein derivatives having the ring structure of fluorescein, attachment of the peptide at the 5 ring position of the fluorensein fluorophore is preferred.

Fluorophores can be linked to the peptide through linking groups which comprise a spacer portion and groups that form the covalent bonds to the peptide and the fluorophore. For fluorescein and fluorescein derivatives having the ring structure of fluorescein, carboxy amine linkers are preferred. Various reagents are commercially available for linking fluorophores to peptides and for generating spacers in the linker. Spacers may include, for example, hydrocarbon spacers ($-CH_2-$), ether or polyether spacers.

Non-Covalent Association of Fluorophores with Nucleic Acids and Proteins

In one embodiment, the fluorophore is non-covalently bound to the translocating peptides and/or nucleic acids of the complexes. Without wishing to be limited to any particular theory, the association of a translocating peptide and a nucleic acid is believed to be non-covalent. When the fluorophore is also non-covalently bound, to the peptide, nucleic acid, or both, the resulting complex is referred to as a fully non-covalent complex.

Nucleic acids that bind fluorophores, including by way of non-limiting example aptamers, can be prepared and used to prepare fully non-covalent complexes of nucleic acids, proteins and fluorophores. Similarly, proteins and peptides that bind fluorophores can be prepared, including without limitation antibodies and derivatives thereof (e.g., single-chain antibodies, camelid antibodies, CDRs, etc.).

A non-covalent specific binding pair can be used to prepare fully non-covalent complexes. In this embodiment, one member of the specific binding pair is associated with the nucleic acid or peptide, and the other member is associated with the fluorophore. The specific binding of members of the pair to each other results in a non-covalent linkage between the nucleic acid or peptide that comprises a member of the binding pair and the fluorophore. For example, biotin and streptavidin can be used to cause the non-covalent association of as fluorophore with a nucleic acid or protein. A strong non-covalent bond is formed between the biotin and avidin moieties (the dissociation constant is approximately $10^{15}$).

In one mode, a biotin moiety can be attached to the fluorophore, and the peptide or oligonucleotide may comprise a streptavidin or avidin moiety. See Sano T, Vajda S, Cantor C R. Genetic engineering of streptavidin, a versatile affinity tag. J Chromatogr B Biomed Sci Appl. 715:85-91, 1998. For example, a fusion protein comprising VP22 translocating protein and strepavidin may be generated and complexed with a biotinylated fluorophore.

Compositions and Methods of Use

Thus, the invention provides polymer complexes comprising one or more proteins or peptides, one or more nucleic acid molecules, and optionally one or more fluorophores, produced by the methods of this invention and other methods known to those in the art, including automated and semi-automated methods. For example, an automated device for forming complexes of nucleic acids and poly-Lys is described in U.S. Pat. No. 6,281,005 to Casal, et al. In related aspects, the invention also provides compositions comprising one or more such conjugates or complexes. Compositions according to this aspect of the invention will comprise one or more (e.g., one, two, three, four, five, ten, etc.) of the above-described conjugates or complexes of the invention. In certain such aspects, the compositions may comprise one or more additional components, such as one or more buffer salts, one or more chaotropic agents, one or more detergents, one or more proteins (e.g., one or more enzymes), one or more polymers and the like. The compositions of this aspect of the invention may be in any form, including solid (e.g., dry powder) or solution (particularly in the form of a physiologically compatible buffered salt solution comprising one or more of the conjugates of the invention).

Pharmaceutical Compositions

Certain compositions of the invention are particularly formulated for use as pharmaceutical compositions for use in prophylactic, diagnostic or therapeutic applications. Such compositions will typically comprise one or more of the conjugates, complexes or compositions of the invention and one or more pharmaceutically acceptable carriers or excipients. The term "pharmaceutically acceptable carrier or excipient," as used herein, refers to a non-toxic solid, semi-solid or liquid filler, diluent, encapsulating material or formulation auxiliary of any type that is capable of being tolerated by a recipient animal, including a human or other mammal, into which the pharmaceutical composition is introduced, without adverse effects resulting from its addition.

The pharmaceutical compositions of the invention may be administered to a recipient via any suitable mode of administration, such as orally, rectally, parenterally, intrasystenically, vaginally, intraperitoneally, topically (as by powders, ointments, drops or transdermal patch), buccally, as an oral or nasal spray or by inhalation. The term "parenteral" as used herein refers to modes of administration that include intravenous, intramuscular, intraperitoneal, intracisternal, subcutaneous and intra-articular injection and infusion.

Pharmaceutical compositions provided by the present invention for parenteral injection can comprise pharmaceutically acceptable sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, poly(ethylene glycol), and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

Such pharmaceutical compositions of the present invention may also contain adjuvants such as preservatives, wetting agents, emulsifying agents and dispersing agents. Prevention of the action of microorganisms may be ensured by the inclusion of various antibacterial and antifungal agents, for example, paraben, benzyl alcohol, chlorobutanol, phenol, sorbic acid, and the like. It may also be desirable to include osmotic agents such as sugars, sodium chloride and the like. Prolonged absorption of the injectable pharmaceutical form may be brought about by the inclusion of agents that delay absorption, such as aluminum monostearate, hydrogels and gelatin.

In some cases, in order to prolong the effect of the drugs, it is desirable to slow the absorption from subcutaneous or intramuscular injection. This may be accomplished by the use of a liquid suspension of crystalline or amorphous material with poor solubility in aqueous body fluids. The rate of absorption of the drug then depends upon its rate of dissolution, which, in turn, may depend upon its physical form.

Alternatively, delayed absorption of a parenterally administered drug form is accomplished by dissolving or suspending the drug in an oil vehicle.

Injectable depot forms are made by forming microencapsulated matrices of the drug in biodegradable polymers such as polylactide-polyglycolide. Depending upon the ratio of drug to carrier polymer and the nature of the particular carrier polymer employed, the rate of drug release can be controlled. Examples of other biodegradable polymers include biocompatible poly(orthoesters) and poly(anhydrides). Depot injectable formulations are also prepared by entrapping the drug in liposomes or microemulsions that are compatible with body tissues.

The injectable formulations can be sterilized, for example, by filtration through a bacteria-retaining filter, or by incorporating sterilizing agents in the form of sterile solid compositions that can be dissolved or dispersed in sterile water or other sterile injectable medium prior to use.

Solid dosage forms for oral administration include capsules, tablets, pills, powders and granules. In such solid dosage forms, the active compounds are mixed with at least one pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and gum acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) accelerators of absorption, such as quaternary ammonium compounds, g) wetting agents such as, for example, cetyl alcohol and glycerol monostearate, h) adsorbents such as kaolin and bentonite clay, and i) lubricants such as talc, calcium stearate, magnesium stearate, solid poly(ethylene glycols), sodium lauryl sulfate, and mixtures thereof. In the case of capsules, tablets and pills, the dosage form may also comprise buffering agents.

Solid compositions of a similar type may also be employed as fillers in soft- and hard-filled gelatin capsules using such excipients as lactose (milk sugar) as well as high molecular weight poly(ethylene glycols) and the like. The solid dosage forms of tablets, dragees, capsules, pills and granules can be prepared with coatings and shells such as enteric or chronomodulating coatings and other coatings well known in the pharmaceutical formulating art. They may optionally contain opacifying agents and can also be of such a composition that they release the active ingredient(s) only, or preferentially, in a certain part of the gastrointestinal tract, optionally, in a delayed manner. Examples of embedding compositions that can be used include polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, poly(ethylene glycols) and fatty acid esters of sorbitan, and mixtures thereof. In addition to inert diluents, the oral compositions can also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredients in finely divided form may be used in admixture with a larger-sized pharmaceutically acceptable inert carrier comprising particles having a size, for example, of up to 100 micrometers in diameter. Suitable inert carriers include sugars such as lactose and sucrose. Desirably, at least 95% by weight of the particles of the active ingredient have an effective particle size in the range of 0.01 to 10 micrometer.

Alternatively, the pharmaceutical composition may be pressurized and contain a compressed gas, such as nitrogen or a liquefied gas propellant. The liquefied propellant medium and indeed the total composition may be preferably such that the active ingredients do not dissolve therein to any substantial extent. The pressurized composition may also contain a surface-active agent. The surface-active agent may be a liquid or solid non-ionic surface-active agent or may be a solid anionic surface-active agent. It is preferable to use the solid anionic surface-active agent in the form of a sodium salt.

A further form of topical administration is to the eye. In this mode of administration, the conjugates or compositions of the invention are delivered in a pharmaceutically acceptable ophthalmic vehicle, such that the active compounds are maintained in contact with the ocular surface for a sufficient time period to allow the compounds to penetrate the conjunctiva or the corneal and internal regions of the eye, as for example the anterior chamber, posterior chamber, vitreous body, aqueous humor, vitreous humor, cornea, iris/ciliary, lens, choroid/retina and sclera. The pharmaceutically acceptable ophthalmic vehicle may, for example, be an ointment, vegetable oil or an encapsulating material.

Compositions for rectal or vaginal administration are preferably suppositories that can be prepared by mixing the conjugates or compositions of the invention with suitable non-irritating excipients or carriers such as cocoa butter, PEG or a suppository wax, which are solid at room temperature but liquid at body temperature and therefore melt in the rectum or vaginal cavity and release the drugs.

The pharmaceutical compositions used in the present therapeutic methods may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. In addition to one or more of the conjugates or compositions of the invention, the present pharmaceutical compositions in liposome form can also contain one or more stabilizers, preservatives, excipients, and the like. The preferred lipids are the phospholipids and the phosphatidyl cholines (lecithins), both natural and synthetic. Methods to form liposomes are known in the art (see, e.g., Zalipsky, S., et al., U.S. Pat. No. 5,395,619). Liposomes that comprise phospholipids that are conjugated to poly(ethylene glycol) ("PEG"), most commonly phosphatidyl ethanolamine coupled to monomethoxy-PEG, have advantageous properties, including prolonged lifetimes in the blood circulation of mammals (Fisher, D., U.S. Pat. No. 6,132,763).

Other Uses

As noted elsewhere herein, the polymer, complexes and compositions of the present invention are advantageously used in methods for delivering one or more components (e.g., one or more peptides and/or one or more nucleic acid molecules and/or one or more fluorophores) of the complexes and compositions to cells, tissues, organs or organisms. In particular, the invention provides controlled delivery of the one or more components of the complexes or compositions to cells, tissues, organs or organisms, thereby providing the user with the ability to regulate, temporally and spacially, the amount of a particular component that is released for activity on the cells, tissues, organs or organisms.

In general, such methods of the invention involve one or more activities. For example, one such method of the invention comprises: (a) preparing one or more complexes or compositions of the invention as detailed herein and (b) contacting one or more cells, tissues, organs or organisms with the one or more complexes or compositions, under conditions favoring the uptake of the one or more complexes or compositions of the invention by the cells, tissues, organs or organisms. In another embodiment, the invention further provides for the method comprising the added step (c), treating the cells, tissues, organs or organisms that contain the one or more complexes or compositions of the invention with a treatment that releases one or more of the bioactive components of the conjugates or compositions into the cells, tissues, organs or organisms.

Once the bioactive components of the complexes and/or compositions of the invention have entered the cells or been released into the cells, tissues, organs or organisms, the components proceed to carry out their intended biological functions. For example, peptide components released into the cells, tissues, organs or organisms may proceed to bind to receptors or other compounds or components within the cells, tissues, organs or organisms; to participate in metabolic reactions within the cells, tissues, organs or organisms; to carry out, upregulate or activate, or downregulate or inhibit, one or more enzymatic activities within the cells, tissues, organs or organisms; to provide a missing structural component to the cells, tissues; organs or organisms; to provide one or more nutritional needs to the cells, tissues, organs or organisms; to inhibit, treat, reverse or otherwise ameliorate one or more processes or symptoms of a disease or physical disorder; and the like. In other examples, nucleic acid components released into the cells, tissues, organs or organisms may proceed to bind to receptors or other compounds or components within the cells, tissues, organs or organisms; to become incorporated into the genetic material within the cells, tissues, organs or organisms, whether chromosomal or extrachromosomal, genomic or otherwise; to carry out, upregulate or activate, or downregulate or inhibit, one or more enzymatic activities within the cells, tissues, organs or organisms; to provide a missing genetic component to the cells, tissues, organs or organisms; to increase or decrease the copy number of one or more genes within the cells, tissues, organs or organisms; to inhibit, treat, reverse or otherwise ameliorate one or more processes or symptoms of a disease or physical disorder, and the like. In related aspects, the complexes and compositions of the invention can be used to produce transgenic cells, tissues, organs or organisms, including non-human transgenic animals such as mice, rats, dogs, cows, pigs, rabbits, dogs, monkeys and the like, using methods (such as nuclear transfer cloning) that are well-known in the art and that will be familiar to the ordinarily skilled artisan (see, e.g., U.S. Pat. Nos. 5,322,775, 5,366,894; 5,476,995, 5,650,503 and 5,861, 299; WIPO/PCT publication nos. WO 98/37183 and WO 00/42174; U.S. patent application publication no. 0012660-A1 (published on Jan. 31, 2002); Dai et al., Nature Biotechnology 20: 251-255 (2002); Betthauser et al., Nature Biotechnology 18: 1055-1059 (2000); Onishi et al., Science 289: 1188-1190 (2000); and Polejaeva et al., Nature 407:86-90 (2000). The disclosures of all of these documents are incorporated herein by reference in their entireties).

Dose Regimens

The conjugates, complexes or compositions of the invention can be administered in vitro, ex vivo or in vivo to cells, tissues, organs or organisms to deliver one or more bioactive components (i.e., one or more peptides or nucleic acid molecules) thereto. One of ordinary skill will appreciate that effective amounts of a given active compound, conjugate, complex or composition can be determined empirically and may be employed in pure form or, where such forms exist, in pharmaceutically acceptable formulation or prodrug form. The compounds, conjugates, complexes or compositions of the invention may be administered to an animal (including a mammal, such as a human) patient in need thereof as veterinary or pharmaceutical compositions in combination with one or more pharmaceutically acceptable excipients. It will be understood that, when administered to a human patient, the total daily, weekly or monthly usage of the compounds and compositions of the present invention will be decided by the attending physician within the scope of sound medical judgment. The therapeutically effective dose level for any particular patient will depend upon a variety of factors including the type and degree of the cellular response to be achieved; the identity and/or activity of the specific compound(s), conjugate(s), complex(es) or composition(s) employed; the age, body weight or surface area, general health, gender and diet of the patient; the time of administration, route of administration, and rate of excretion of the active compound(s); the duration of the treatment; other drugs used in combination or coincidental with the specific compound(s), conjugate(s), complex(es) or composition(s); and like factors that are well known to those of ordinary skill in the pharmaceutical and medical arts. For example, it is well within the skill of the art to start doses of a given compound, conjugate, complex or composition of the invention at levels lower than those required to achieve the desired therapeutic effect and to gradually increase the dosages until the desired effect is achieved.

Dose regimens may also be arranged in a patient-specific manner to provide a predetermined concentration of a given active compound in the blood, as determined by techniques accepted and routine in the art, e.g. size-exclusion, ion-exchange or reversed-phase HPLC. Thus, patient dose regimens may be adjusted to achieve relatively constant blood levels, as measured by HPLC, according to methods that are routine and familiar to those of ordinary skill in the medical, pharmaceutical and/or pharmacological arts.

Diagnostic and Therapeutic Uses

In one embodiment, the diagnostic use of a polymer complex of the present invention is for locating an antigenic moiety, e.g., a cancer, within the body of an animal, especially a human, by administration of a complex or composition of the invention, in which the complex or conjugate is labeled or comprises one or more detectable labels so as to enable detection, e.g., by optical, radiometric, fluorescent or resonant detection according to art-known methods. Hence, in another aspect of the invention, the conjugates and compositions of the invention may be used in diagnostic or therapeutic methods, for example in diagnosing, treating or preventing a variety of physical disorders in an animal, particularly a mammal such as a human, predisposed to or suffering from such a disorder. In such approaches, the goal of the therapy is to delay or prevent the development of the disorder, and/or to cure or induce a remission of the disorder, and/or to decrease or minimize the side effects of other therapeutic regimens. Hence, the complexes and compositions of the present invention may be used for protection, suppression or treatment of physical disorders, such as infections or diseases. The term "protection" from a physical disorder, as used herein, encompasses "prevention," "suppression" and "treatment." "Prevention" involves the administration of a complex or composition of the invention prior to the induction of the disease or physical disorder, while "suppression" involves the administration of the complex or composition prior to the clinical appearance of the disease; hence, "prevention" and "suppression" of a physical disorder typically are undertaken in an animal that is predisposed to or susceptible to the disorder, but that is not yet suffering therefrom. "Treatment" of a physical disorder, however, involves administration of the therapeutic complex or composition of the invention after the appearance of the disease. It will be understood that in human and veterinary medicine, it is not always possible to distinguish between "preventing" and "suppressing" a physical disorder. In many cases, the ultimate inductive event or events may be unknown or latent, and neither the patient nor the physician may be aware of the inductive event until well after its occurrence. Therefore, it is common to use the term "prophylaxis," as distinct from "treatment," to encompass both "preventing" and "suppressing" as defined herein. The term "protection," used in accordance with the methods of the present invention, therefore is meant to include "prophylaxis."

Methods according to this aspect of the invention may comprise one or more steps that allow the clinician to achieve the above-described therapeutic goals. One such method of the invention may comprise, for example: (a) identifying an animal (preferably a mammal, such as a human) suffering from or predisposed to a physical disorder, and (b) administering to the animal an effective amount of one or more of the polymer complexes or compositions of the present invention as described herein, particularly one or more complexes comprising one or more peptides and/or one or more nucleic acids, and/or one or more fluorophores (or one or more pharmaceutical compositions comprising such conjugates), such that the administration of the conjugate, complex or composition prevents, delays or diagnoses the development of, or cures or induces remission of, the physical disorder in the animal.

As used herein, an animal that is "predisposed to" a physical disorder is defined as an animal that does not exhibit a plurality of overt physical symptoms of the disorder but that is genetically, physiologically or otherwise at risk for developing the disorder. In the present methods, the identification of an animal (such as a mammal, including a human) that is predisposed to, at risk for, or suffering from a given physical disorder may be accomplished according to standard art-known methods that will be familiar to the ordinarily skilled clinician, including, for example, radiological assays, biochemical assays (e.g., assays of the relative levels of particular peptides, proteins, electrolytes, etc., in a sample obtained from an animal), surgical methods, genetic screening, family history, physical palpation, pathological or histological tests (e.g., microscopic evaluation of tissue or bodily fluid samples or smears, immunological assays, etc.), testing of bodily fluids (e.g., blood, serum, plasma, cerebrospinal fluid, urine, saliva, semen and the like), imaging, (e.g., radiologic, fluorescent, optical, resonant (e.g., using nuclear magnetic resonance (NMR) or electron spin resonance (ESR)), etc. Once an animal has been identified by one or more such methods, the animal may be aggressively and/or proactively treated to prevent, suppress, delay or cure the physical disorder.

Physical disorders that can be prevented, diagnosed or treated with the complexes, compositions and methods of the present invention include any physical disorders for which the peptide and/or nucleic acid component(s) of the complexes or compositions may be used in the prevention, diagnosis or treatment. Such disorders include, but are not limited to, a variety of cancers (e.g., breast cancers, uterine cancers, ovarian cancers, prostate cancers, testicular cancers, leukemias, lymphomas, lung cancers, neurological cancers, skin cancers, head and neck cancers, bone cancers, colon and other gastrointestinal cancers, pancreatic cancers, bladder cancers, kidney cancers and other carcinomas, sarcomas, adenomas and myelomas); infectious diseases (e.g., bacterial diseases, fungal diseases, viral diseases (including hepatitis and HIV/AIDS), parasitic diseases, and the like); genetic disorders (e.g., cystic fibrosis, amyotrophic lateral sclerosis, muscular dystrophy, Gaucher's disease, Pompe's disease, severe combined immunodeficiency disorder and the like), anemia, neutropenia, hemophilia and other blood disorders; neurological disorders (e.g., multiple sclerosis and Alzheimer's disease); enzymatic disorders (e.g., gout, uremia, hypercholesterolemia, and the like); disorders of uncertain or multifocal etiology (e.g., cardiovascular disease, hypertension, and the like); and other disorders of medical importance that will be readily familiar to the ordinarily skilled artisan. The complexes, compositions and methods of the present invention may also be used in the prevention of disease progression, such as in chemoprevention of the progression of a premalignant lesion to a malignant lesion.

The therapeutic methods of the invention thus use one or more conjugates, complexes or compositions of the invention, or one or more of the pharmaceutical compositions of the invention, that may be administered to an animal in need thereof by a variety of routes of administration, including orally, rectally, parenterally (including intravenously, intramuscularly, intraperitoneally, intracisternally, subcutaneously and intra-articular injection and infusion), intrasystemically, vaginally, intraperitoneally, topically (as by powders, ointments, drops or transdermal patch), buccally, as an oral or nasal spray or by inhalation. By the invention, an effective amount of the conjugates, complexes or compositions can be administered in vitro, ex vivo or in vivo to cells or to animals suffering from or predisposed to a particular disorder, thereby preventing, delaying, diagnosing or treating the disorder in the animal. As used herein, "an effective amount of a conjugate (or complex or composition)" refers to an amount such that the conjugate (or complex or composition) carries out the biological activity of the bioactive component (i.e., the peptide and/or nucleic acid component) of the conjugate/complex/composition, thereby preventing, delaying, diagnosing, treating or curing the physical disorder in the animal to which the conjugate, complex or composition of the invention has been administered. One of ordinary skill will appreciate that effective amounts of the conjugates, complexes or compositions of the invention can be determined empirically, according to standard methods well-known to those of ordinary skill in the pharmaceutical and medical arts; see, e.g., Beers, M. H., et al., eds. (1999) Merck Manual of Diagnosis & Therapy, 17th edition, Merck and Co., Rahway, N J; Hardman, J. G., et al., eds. (2001) Goodman and Gilman's The Pharmacological Basis of Therapeutics, 10th edition, McGraw-Hill Professional Publishing, Elmsford, N.Y.;

Speight, T. M., et al., eds. (1997) Avery's Drug Treatment Principles and Practice of Clinical Pharmacology and Therapeutics, 4th edition, Blackwell Science, Inc., Boston; Katzung, B. G. (2000) Basic and Clinical Pharmacology, 8th edition, Appleton and Lange, Norwalk, Conn.; which references and references cited therein are incorporated entirely herein by reference.

It will be understood that, when administered to a human patient, the total daily, weekly or monthly dosage of the conjugates, complexes and compositions of the present invention will be decided by the attending physician within the scope of sound medical judgment. For example, satisfactory results are obtained by administration of certain of the conjugates, complexes or compositions of the invention at appropriate dosages depending on the specific bioactive compound used, which dosages will be readily familiar to the ordinarily skilled artisan or which may be readily determined empirically using only routine experimentation. According to this aspect of the invention, the conjugates, complexes or compositions can be administered once or, in divided doses, e.g., twice per day or per week or per month. Appropriate dose regimens for various modes of administration (e.g., parenteral, subcutaneous, intramuscular, intraocular, intranasal, etc.) can also be readily determined empirically, using only routine experimentation, or will be readily apparent to the ordinarily skilled artisan, depending on the identity of the bioactive component (i.e., the peptide and/or nucleic acid component) of the conjugate, complex or composition.

In additional applications, the conjugates, complexes and compositions of the invention may be used to specifically target a diagnostic or therapeutic agent to a cell, tissue, organ or organism that expresses a receptor for, binds, incorporates or otherwise can take up, the bioactive component (i.e., the peptide and/or nucleic acid component) of the conjugate, complex or composition. Methods according to this aspect of the invention may comprise, for example, contacting the cell, tissue, organ or organism with one or more conjugates, complexes or compositions of the invention, which additionally comprise one or more diagnostic or therapeutic agents, such that the conjugate, complex or composition is taken up by the cell, tissue, organ or organism by any mechanism (e.g., by receptor-mediated endocytosis, pinocytosis, phagocytosis, diffusion, etc.), thereby delivering the diagnostic or therapeutic agent to the cell, tissue, organ or organism. The diagnostic or therapeutic agent used in accordance with this aspect of the invention may be, but is not limited to, at least one agent selected from a nucleic acid, an organic compound, a protein or peptide, an antibody, an enzyme, a glycoprotein, a lipoprotein, an element, a lipid, a saccharide, an isotope, a carbohydrate, an imaging agent, a detectable probe, or any combination thereof, which may be detectably labeled as described herein. A therapeutic agent used in this aspect of the present invention may have a therapeutic effect on the target cell (or tissue, organ or organism), the effect being selected from, but not limited to, correcting a defective gene or protein, a drug action, a toxic effect, a growth stimulating effect, a growth inhibiting effect, a metabolic effect, a catabolic affect, an anabolic effect, an antiviral effect, an antifungal effect, an antibacterial effect, a hormonal effect, a neurohumoral effect, a cell differentiation stimulatory effect, a cell differentiation inhibitory effect, a neuromodulatory effect, an anti-neoplastic effect, an anti-tumor effect, an insulin stimulating or inhibiting effect, a bone marrow stimulating effect, a pluripotent stem cell stimulating effect, an immune system stimulating effect, and any other known therapeutic effect that may be provided by a therapeutic agent delivered to a cell (or tissue, organ or organism) via a delivery system according to this aspect of the present invention.

Such additional therapeutic agents may be selected from, but are not limited to, known and new compounds and compositions including antibiotics, steroids, cytotoxic agents, vasoactive drugs, antibodies and other therapeutic agents. Non-limiting examples of such agents include antibiotics and other drugs used in the treatment of bacterial shock, such as gentamycin, tobramycin, nafcillin, parenteral cephalosporins, etc.; adrenal corticosteroids and analogs thereof, such as dexamethasone, mitigate the cellular injury caused by endotoxins; vasoactive drugs, such as an alpha adrenergic receptor blocking agent (e.g., phenoxybenzamine), a beta adrenergic receptor agonist (e.g., isoproterenol), and dopamine.

The conjugates, complexes and compositions of the invention may also be used for diagnosis of disease and to monitor therapeutic response. In certain such methods, the conjugates, complexes or compositions of the invention may comprise one or more detectable labels (such as those described elsewhere herein). In specific such methods, these detectably labeled conjugates, complexes or compositions of the invention may be used to detect cells, tissues, organs or organisms expressing receptors for, or otherwise taking up, the bioactive component (i.e., the peptide and/or nucleic acid component) of the conjugates, complexes or compositions. In one example of such a method, the cell, tissue, organ or organism is contacted with one or more of the conjugates, complexes or compositions of the invention under conditions that favor the uptake of the conjugate by the cell, tissue or organism (e.g., by binding of the conjugate to a cell-surface receptor or by pinocytosis or diffusion of the conjugate into the cell), and then detecting the conjugate bound to or incorporated into the cell using detection means specific to the label used (e.g., fluorescence detection for fluorescently labeled conjugates; magnetic resonance imaging for magnetically labeled conjugates; radioimaging for radiolabeled conjugates; etc.). Other uses of such detectably labeled conjugates may include, for example, imaging a cell, tissue, organ or organism, or the internal structure of an animal (including a human), by administering an effective amount of a labeled form of one or more of the conjugates of the invention and measuring detectable radiation associated with the cell, tissue, organ or organism (or animal). Methods of detecting various types of labels and their uses in diagnostic and therapeutic imaging are well known to the ordinarily skilled artisan, and are described elsewhere herein.

In another aspect, the conjugates and compositions of the invention may be used in methods to modulate the concentration or activity of a specific receptor for the bioactive component of the conjugate on the surface of a cell that expresses such a receptor. By "modulating" the activity of a given receptor is meant that the conjugate, upon binding to the receptor, either activates or inhibits the physiological activity (e.g., the intracellular signaling cascade) mediated through that receptor. While not intending to be bound by any particular mechanistic explanation for the regulatory activity of the conjugates of the present invention, such conjugates can antagonize the physiological activity of a cellular receptor by binding to the receptor via the bioactive component of the conjugate, thereby blocking the binding of the natural agonist (e.g., the unconjugated bioactive component) and preventing activation of the receptor by the natural agonist, while not inducing a substantial activation of the physiological activity of the receptor itself. Methods according to this aspect of the invention may comprise one or more steps, for example contacting the cell (which may be done in vitro or in vivo) with one or more of the conjugates of the invention, under conditions such that the conjugate (i.e., the bioactive component portion of the conjugate) binds to a receptor for the bioactive component on the cell surface but does not substantially activate the receptor. Such methods will be useful in a variety of diagnostic, and therapeutic applications, as the ordinarily skilled artisan will readily appreciate.

Kits

The invention also provides kits comprising the polymers, conjugates and/or compositions of the invention. Such kits typically comprise a carrier, such as a box, carton, tube or the like, having in close confinement therein one or more containers, such as vials, tubes, ampules, bottles and the like, wherein a first container contains one or more of the conjugates and/or compositions of the present invention. The kits encompassed by this aspect of the present invention may further comprise one or more additional components (e.g., reagents and compounds) necessary for carrying out one or more particular applications of the conjugates and compositions of the present invention, such as one or more components useful for the diagnosis, treatment or prevention of a particular disease or physical disorder (e.g., one or more additional therapeutic compounds or compositions, one or more diagnostic reagents, one or more carriers or excipients, and the like), one or more additional conjugates or compositions of the invention, one or more sets of instructions, and the like.

Cells that may be transfected by a transfection polymer complex incorporating a nucleic acid of the invention include, for example, endothelial or epithelial cells, for example, cells of the any part of the airway epithelium, including bronchial and lung epithelium, and the corneal endothelium. The airway epithelium is an important target for gene therapy for cystic fibrosis and asthma.

A transfection polymer complex as described above may be produced by admixing the polymers and nucleic acid components. The individual components of a transfection mixture of the invention are each as described above in relation to the transfection polymer complex. The preferred components, preferred combinations of components, preferred ratios of components and preferred order of mixing, both with regard to the mixture and to the production of a polymer complex, are as described above in relation to the transfection polymer complex.

The present invention also provides a process for expressing a nucleic acid in host cells, which comprises contacting the host cells in vitro or in vivo with a receptor-targeted polymer complex of the invention comprising the nucleic acid and then culturing the host cells under conditions that enable the cells to express the nucleic acid.

The present invention further provides a process for the production of a protein in host cells, which comprises contacting the host cells in vitro or in vivo with a receptor-targeted polymer complex of the invention that comprises a nucleic acid that encodes the protein, allowing the cells to express the protein, and obtaining the protein. The protein may be obtained either from the host cell or from the culture medium.

The present invention further provides a method of transfecting cells comprising subjecting the cells to a polymer complex according to the invention. The invention further provides cells, transfected with a nucleic acid by a method according to the invention, and also the progeny of such cells.

The present invention further provides a disease model for use in testing candidate pharmaceutical agent, which comprises cells transfected by a method according to the invention with a nucleic acid suitable for creating the disease model.

The present invention also provides a pharmaceutical composition which comprises a receptor-targeted polymer complex of the invention comprising a nucleic acid in admixture or conjunction with a pharmaceutically suitable carrier. The composition may be a vaccine.

The present invention also provides a method for the treatment or prophylaxis of a condition caused in a human or in a non-human animal by a defect and/or a deficiency in a gene, which comprises administering to the human or to the non-human animal a receptor-targeted polymer complex of the invention comprising a nucleic acid suitable for correcting the defect or deficiency.

The present invention also provides a method for therapeutic or prophylactic immunization of a human or of a non-human animal, which comprises administering to the human or to the non-human animal a receptor-targeted polymer complex of the invention comprising an appropriate nucleic acid.

The present invention also provides a method of anti-sense therapy of a human or of a non-human animal, comprising anti-sense DNA administering to the human or to the non-human animal a receptor-targeted polymer complex of the invention comprising the anti-sense nucleic acid.

The present invention also provides the use of a receptor-targeted polymer complex of the invention comprising a nucleic acid for the manufacture of a medicament for the prophylaxis of a condition caused in a human or in a non-human animal by a defect and/or a deficiency in a gene, for therapeutic or prophylactic immunixation of a human or of a non-human animal, or for anti-sense therapy of a human or of a non-human animal.

A non-human animal is, for example, a mammal, bird or fish, and is particularly a commercially reared animal.

The treatments and uses described above may be carried out by administering the respective delivery complex, agent or medicament in an appropriate manner, for example, administration may be topical, for example, in the case of airway epithelia.

In a further embodiment, the present invention provides a kit comprising a polymer complex of the invention comprising a nucleic acid. The present invention also provides a kit that comprises the following items: (a) a polamide polymer; and (b) a nucleic acid. Such a nucleic acid may be single-stranded or double stranded and may be a plasmid or an artificial chromosome. The nucleic acid component may be provided by a vector complex suitable for the expression of the nucleic acid, the vector complex being either empty or comprising the nucleic acid. For in vitro purposes, the nucleic acid may be a reporter gene. For in vivo treatment purposes, the nucleic acid may comprise DNA appropriate for the correction or supplementation being carried out. Such DNA may be a gene, including any suitable control elements, or it may be a nucleic acid with homologous recombination sequences. The components may be provided individually or as complexes in salt free buffer (for example in water, or 5% dextrose).

A kit generally comprises instructions, which preferably indicate the preferred ratios of the components and the preferred order of use or admixing of the components, for example, as described above. A kit may be used for gene therapy, gene vaccination or anti-sense therapy. Alternatively, it may be used for transfecting a host cell with a nucleic acid encoding a commercially useful protein i.e. to produce a so-called "cell factory".

In a kit of the invention the components including the preferred components are, for example, as described above in relation to a delivery complex of the present invention. The polycationic nucleic acid binding component is preferably a polymer, as described above. The rations between the components are preferably as described above, as is the order of mixing of the components.

Targets for gene therapy are well known and include monogenic disorders, for example, cystic fibrosis, various cancers, and infections, for example, viral infections, for example, with HIV. For example, transfection with the p53 gene offers great potential for cancer treatment. Targets for gene vaccination are also well known, and include vaccination against pathogens for which vaccines derived from natural sources are too dangerous for human use and recombinant vaccines are not always effective, for example, hepatitis B virus, HIV, HCV and herpes simplex virus. Targets for anti-sense therapy are also known. Further targets for gene therapy and anti-sense therapy are being proposed as knowledge of the genetic basis of disease increases, as are further targets for gene vaccination. The present invention enhances the transfection efficiency and hence the effectiveness of the treatment.

Delivery complexes of the invention may be effective for intracellular transport of very large DNA molecules, for example, DNA larger than 125 kb, which is particularly difficult using conventional vectors. This enables the introduction of artificial chromosomes into cells.

Transfection of the airways, for example, the bronchial epithelium demonstrates utility for gene therapy of, for example, respiratory diseases, such as cystic fibrosis, emphysema, asthma, pulmonary fibrosis, pulmonary hypertension and lung cancer.

Cystic fibrosis (CF) is the most common monogenic disorder in the Caucasian population. Morbidity is mainly associated with lung disease. CF is caused by mutations in the gene encoding the cystic fibrosis transmembrane conductance regulator protein (CFTR), a cell membrane channel that mediates secretion of chloride ions.

The enhanced levels of transfection make the method of the invention particularly suitable for the production of host cells capable of producing a desired protein, so-called "cell factories". For long-term production, it is desirable that the introduced nucleic acid is incorporated in the genome of the host cell, or otherwise stably maintained. That can be readily ascertained. As indicated above, the range of proteins produced in this way is large, including enzymes for scientific and industrial use, proteins for use in therapy and prophylaxis, immunogens for use in vaccines and antigens for use in diagnosis.

Accordingly, the present invention provides a method of testing drugs in a tissue model for a disease, wherein the tissue model comprises transgenic cells obtained by transfecting cells with a nucleic acid by contacting the cell with a receptor-targeted vector complex of the invention comprising a nucleic acid.

In another embodiment, the present invention provides for the use for polymers to deliver a concatemer to a cell. In another embodiment, the present invention provides for the use for polyamides to deliver a concatemerized double-stranded oligonucleotide molecules (CODN) for transcription factor decoys. In one embodiment, the concatemers consist of a variable number of end-to-end repeated copies of a short dsDNA containing a sequence or sequences that act as transcription factor decoys.

In another embodiment, the present invention provides for the use of the polymers for covalent addition of targeting peptides, receptor binding peptides/protein domains and antibody fragments that may be used to target the CODN/polymer complexes to a specific cell type; thus the agent can be made organ, tissue and/or cell-type specific.

In another embodiment, the present invention provides for using polyamides for targeting peptides and/or antibodies for specific stress and/or drug induced cellular receptors. In one embodiment, the polyamides target the CODN/polymer complexes to ischemic, inflamed or cancerous tissues.

In another embodiment, the present invention provides for using linker peptides containing the sequence recognized by the TNF-alpha converting enzyme (TACE) or another exopeptidase or endopeptidase in order to allow the agent to deliver the CODN/polymer complex to the cell and then cleave off the targeting peptide.

In another embodiment, the present invention provides for using the polyamides to deliver intact genes (transgenes), plasmids, RNAi, siRNA, morpholinos or other kinds of RNA, proteins and polynucleotides. In one embodiment, the genes incorporate tissue-specific promoters, controllable promoters, promoters that may be silenced by specific CODN/polymer combinations and may constitute two- and three-unit systems for gene expression, control and DNA transposition (i.e. insertion, excision and targeting of transgenes and other DNA molecules).

In another embodiment, the present invention provides for use of the polyamides in vitro or in vivo, in isolated cells or intact animals in which specific blockade of transcription factors or delivery of DNA or other biological effector is desirable. In one embodiment, this includes use as a research tool, including studies of specific genes and studies to identify specific genes regulated by the transcription factors targeted (relates to development of specific CODN/polymer complex and related gene marker mouse lines described below). For clinical use, this would include, but is not limited to delivery of transcription factor decoys (e.g. CODNs) that block transcription factors implicated in disease, response to surgery and/or trauma, developmental defects, aging, toxic exposure, etc.

In another embodiment, the present invention provides for transgenic mice expressing marker genes (lacZ and/or GFP variants) under the control of promoter elements that are primarily controlled by specific transcription factors. In one embodiment, the mice are provided separately or as a kit including specific CODN/polymer complexes and the matching mouse, which serves to identify the cells in which the marker activation (experimentally activated) is blocked by the CODN. In another embodiment, there are transgenic mice with marker genes that are transcriptionally turned on, which can be specifically turned off using CODN/polymer complexes.

In another embodiment, the present invention provides for bi-transgenic (or multiple transgenic) systems designed to utilize the CODN/polymer complexes to regulate gene expression (up, down, on or off) or to mediate gene transposition (insertion, excision or moving in the genome).

In another embodiment, the present invention provides for polymers designed for variable release/biodegradation; some may be designed, selected for quick degradation/release of CODN, others for long half-life (the CODN may be active whether or not it is released by the polymers, so we should safeguard the concept that long-lasting binding of the DNA by polymers may be a way to prolong activity).

In another embodiment, the present invention provides for the delivery of one or more imaging agents for real-time and still imaging within a cell or tissue.

In another embodiment, the present invention provides for using polyamides for delivery of transcription factor decoys to block signaling and gene expression associated with pathogenesis.

In another embodiment, the present invention provides for using polyamides for delivery of linear duplications or chains of these decoys (i.e., concatemers), such that each strand contains a number of decoy transcription factor binding sites including more than 1, 2, 3, 4, 5, 6, 7, 8, 9, 10, 15, 20, 25, or more. A concatemer is a segment composed of repeated sequences linked end to end. In one embodiment, the concatemer may form a circular nucleotide.

In another embodiment, the present invention provides for using polyamides for delivery of decoys having for multiple transcription factors into one of these strands, such that it can affect blockade of 2, 3, 4, 5, 6, or more transcription factors simultaneously in a cell. In another embodiment, the present invention provides for using polyamides for delivery of these strands, or the strands contained in a plasmid or other DNA vector (can include phage, viral or other DNA) to bind to the polymers to deliver the strands to the cytoplasm of the cell, to effect transcription factor blockade.

Oligonucleotide Decoys

In one embodiment, the present invention relates to the use of oligonucleotide decoys and/or concatemers for the production of a medicament for the therapy of NF-κB-dependent diseases. The present invention also relates to the prevention and treatment of various diseases associated with NF-κB which is known to be a regulatory factor in the transcription of cytokines and adhesion factors. More particularly, the invention relates to a novel form of NF-κB decoy, a composition comprising the decoy for the therapy and prophylaxis of NF-κB-associated diseases, and a method for the therapy and prophylaxis.

In another embodiment, the present invention provides for using delivery agent for NF-kB-specific CODN delivery in the treatment of myocardial ischemia/reperfusion and myocardial infarction, heart failure and hypertrophy, cardioprotection, stroke, neuroprotection, sepsis, arthritis, asthma, heritable inflammatory disorders, cancer, heritable immune dysfunctions, inflammatory processes, whether caused by disease or injury or infection, oxidative stress to any organ whether caused by disease, surgery or injury. In another embodiment, the present invention provides for using delivery agents for delivery of CODN's to delineate in animal models, specific situations in which NF-kB or other transcription factors contribute to injury, dysfunction, morbidity or mortality, determine whether blockade is beneficial in animals and then translating this to the clinic.

An important step in many inflammatory processes is the translocation of the protein "nuclear factor kappa B" to the nuclear compartment of the cell; in brief, translocation of NF-κB, into the cell nucleus and the stimulation of the expression of the genes caused thereby, whose products are responsible for inflammatory reactions. For example, in asthma the nonbeneficial, excessive (non self-limiting) production of these proteins is responsible for the intensification and maintenance of the inflammatory process and the unpleasant to life-threatening symptoms of this disease associated therewith. Because the long-term treatment with glucocorticoids corresponding to the present state of the art is affected by some severe and often debilitating disadvantages, NF-κB is seen as a compelling target for the development of new anti-inflammatory active compounds against asthma.

The oligonucleotide decoy substances utilizable according to the invention are inhibitors which selectively inhibit nuclear factor kappa B (NF-κB)-mediated pathophysiological processes. NF-κB-mediated processes occur in inflammatory diseases, immunological disorders, septic shock, transplant rejection, radiation damage, reperfusion injuries after ischemia, hypoxia, asthma, cardiomyopathy, cardiac hypertrophy, heart failure, muscle wasting, thromboses or in complex, chronic inflammatory disorders such as arteriosclerosis.

Nuclear factor kappa B (NF-κB) is a dimeric protein complex occurring in many tissue cells and in particular in blood cells. NF-κB takes on a particular role in the control of the expression of genes which have an NF-KB binding sequence (5'-GGGPuNNPyPyCC-3') (SEQ ID NO: 3) in their promoter sequence. To this extent, NF-κB is a transcription factor. The physiological activity of NF-κB in the control of gene expression, however, is subject to a regulation principle, in which NF-κB is released from a complex with proteins of the IκB class in order to be translocated as a transcription factor to the cell nucleus resulting in gene activation. The regulation principle for the release of active NF-κB from a complex with the protein IκB is still not known in detail.

Likewise, it is not known how the formation of homodimeric and heterodimeric NF-κB protein complexes takes place. NF-κB acts on gene activation as a dimeric transcription factor. The dimerization can take place under the structurally related transcription factors Rel A, Rel B, c-Rel, p50 or p52, which form a family of transcription factor proteins.

The formation of different transcription factor dimmers provides some degree of selectivity for different NF-kB DNA binding sites in vivo in different promoters. For instance, p65/p50 and p50/p50 as well as p65/p65 dimers are known to bind different specific NF-kB binding sites, that vary by only a few bases, with different affinities. These different NF-kB dimmers may have distinct effects, such as different levels of gene activation (P65/p50 vs. p65/p65) and gene repression (p50/p450). This is thought to provide a basis for variation of NF-kB regulatory effects upon different genes, but is not yet understood in detail.

This selectivity of NF-kB dimmers could be taken advantage of in one embodiment of the invention by varying the specific decoy sequence in the CODN or by using specific combinations of variant decoys to specifically blockade specific NF-kB dimmers. Furthermore, this NF-kB variant dimmers may be precisely and selectively blocked relative to one another by controlling the relative number of the specific variant decoy sites in a CODN sequence. Future investigations may reveal utility of this capability in specific diseases.

A crucial feature of NF-κB compared to other transcription factors is that NF-κB is a primary transcription factor. Primary transcription factors are already present in the cell in inactive (usually complex-bound) form and are released after an appropriate stimulus in order to be able to display their action very rapidly. Primary transcription factors are not first formed by the activation of the associated gene and subsequent transcription and translation.

This property of NF-κB, the formation of homodimeric or heterodimeric Rel proteins and the formation of an inactive protein complex with an IκB protein, offer very different points of attack for pharmacologically active substances than the points of attack of the de novo biosynthesis of transcription factors. For the sake of completeness, it may be mentioned that the genes for the formation of NF-κB (genes of the Rel family) and the genes for the formation of the IκB proteins (gene family comprising the genes for IκB-α, IκB-beta, p105/IκB-gamma, p100/IκB-delta, IκB-epsilon and others) for their part are of course also subject to regulation, by NF-κB itself, among other factors, which can be points of attack for pharmaceutically active substances. Thus it is known that the expression of the constitutively formed IκB proteins p105 and p100 is increased by stimuli which also activate NF-κB, such as tumour necrosis factor-α (TNF-α) or phorbol myristate acetate (PMA). However, blocking expression of NF-kB constituent and regulatory factors will not acutely affect NF-kB activation since previously synthesized NF-kB remains for some time. Thus, the novel aspect of the invention comes into play, allowing for immediate blockade of NF-kB activation by titration (binding) of existing NF-kB molecules.

A regulation mechanism is described in the literature in which it is shown that the overexpression of IκB binds active NF-κB and thus inactivates it. This also applies if the NF-κB has already entered into a complex with the DNA (P. A. Baeuerle, T. Henkel, Annu. Rev. Immunol. 12, 141-179, 1994). From this it can be concluded that there are a number of specific points of attack in the biochemical function of NF-κB and IκB proteins which should make it possible to inhibit an undesirable, pathophysiological, NF-κB-dependent gene activation selectively.

A chemical compound which selectively inhibits the function of NF-κB or the function of IκB proteins or IκB genes to an increased extent should be able to be used as a pharmaceutical for the suppression of NF-κB-mediated disease processes.

Primarily, NF-κB can promote all pathophysiological processes in which genes are involved which have the NF-κB binding sequence in their promoter. Mainly, these are genes which play a crucial causal role in immunological complications, in inflammatory diseases, autoimmune disorders, septic shock, transplant rejection, cell death, cancer, asthma, thromboses or else alternatively in chronic inflammatory diseases such as arteriosclerosis, arthritis, rheumatism and psoriasis.

NF-κB binding sequences are contained, for example, in the promoters of receptors of lymphoid cells (T-cell receptors), of MHCI and MHCII genes, of cell adhesion molecules (ELAM-1, VCAM-1, ICAM-1), of cytolines and growth factors (see also the following table). Furthermore, NF-κB binding sequences are found in the promoters of acute phase proteins (angiotensinogen, complement factors and others).

A chronically increased or acutely overshooting activation of the genes mentioned leads to various pathophysiological processes and syndromes.

The rapid and overshooting production of cytokines and chronic maintenance of pathological expression of the inflammatory reaction (TNFα, interleukin-2, interleukin-6, interleukin-8 and others) and of the adhesion molecules (ELAM-1, ICAM-1, VCAM-1) in leukocytes, in particular in macrophages and also in endothelial cells and cardiomyocytes, is a causal feature of processes which often run a fatal course in the case of septic shock; or in the case of radiation damage and in the case of transplant rejection often leads to considerable complications. Inhibitors which prevent the NF-κB-mediated gene expression intervene very early in some diseases in the expression of pathophysiological changes and can therefore be a very effective therapeutic principle. An example is also NF-κB inhibitors for diseases which are to be attributed to an overexpression of acute-phase proteins. An undesirable overexpression of acute-phase proteins can cause a complex general reaction in which tissue damage of very different types, fever and local symptoms such as inflammation and necroses can occur.

Levels of specific serum proteins and circulating cell types are usually changed as is regulation of both the adaptive and innate immune system function; all of these are known to be affected by NF-kB. NF-κB strongly induces, for example, the serum amyloid A precursor protein in the liver in the course of induction of acute-phase proteins.

For example, the NF-κB-mediated gene expression of the interleukin-2-(Il-2) gene can be inhibited.

Interleukin-2 is a cytokine, which plays a central role in various inflammatory processes, inter alia, as a hematopoietic growth factor (Annu. Rev. Immunol. 1994, 12: 141-79). The promoter of the interleukin-2 gene is NF-κB dependent. An inhibitor of NF-κB stimulation thus opens up the possibility of preventing overshooting of Il-2 production and thus of treating inflammatory processes.

In the case of other syndromes such as tissue damage after reperfusion or cirrhosis of the liver, inhibitors of NF-κB-mediated gene expression can likewise represent an important therapeutic advance. There is evidence that NF-κB-controlled genes are induced as a result of oxidation reactions which lead to oxidative stress after reperfusion of ischemic tissue. In this way, an overexpression of cytokines and cell adhesion molecules in the ischemic tissue causes excessive recruitment of infiltrating alymphocytes. The recruited lymphocytes contribute causally to the tissue damage.

The involvement of NF-κB-controlled gene expression is evident in a number of neurodegenerative disorders. In particular in the case of nervous diseases in which the redox state of cells of the neuronal tissue is disturbed, a therapeutic benefit is ascribed to the selective inhibition of genes having an NF-κB binding sequence. A disturbed redox state of neuronal cells is assumed in the case of amyotropic lateral sclerosis and in Down's syndrome.

It is therefore the general object of this invention to provides a method of inhibiting or preventing cell death or apoptosis in ischemic-reperfused myocardium using novel oligonucleotide decoys or CODNS.

The present invention provides a method for inhibiting cell death and apoptosis in ischemic-reperfused myocardium by administering to a mammal an effective amount of oligonucleotide and/or concatameric decoy, to reduce or prevent myocardial cell death in myocardial infarction. Furthermore, oligonucleotide decoys, either alone or conjugated to a polymeric vector or polyplex group, can be used to block apoptosis in situations of acute trauma, such as generalized trauma, global ischemia-reperfusion injury occurring as a consequence of hemorrhagic shock, or spinal cord injury, thereby preventing cell death in organs such as the spinal cord.

In another embodiment, the present invention provides for the use for polymers to deliver a concatemer to a cell. In another embodiment, the present invention provides for the use for polymers to deliver a concatemerized double-stranded oligonucleotide molecules (CODN) for transcription factor decoys. In one embodiment, the concatemers consist of a variable number of end-to-end repeated copies of a short (20-30 bp) dsDNA containing a sequence or sequences that act as transcription factor decoys.

In another embodiment, the present invention provides for the use of delivery agents for covalent addition of targeting peptides, receptor binding peptides/protein domains and antibody fragments that may be used to target the CODN's to a specific cell type; thus the agent can be made organ, tissue and/or cell-type specific.

In another embodiment, the present invention provides for using polymers for targeting peptides and/or antibodies for specific stress and/or drug induced cellular receptors. In one embodiment, the polymers target the CODN's to ischemic, inflamed or cancerous tissues.

In another embodiment, the present invention provides for using linker peptides containing the sequence recognized by the TNF-alpha converting enzyme (TACE) or another exopeptidase or endopeptidase in order to allow the agent to deliver the CODN's to the cell and then cleave off the targeting peptide.

In another embodiment, the present invention provides for using the polymers to deliver intact genes (transgenes), plasmids, RNAi, siRNA, morpholinos or other kinds of RNA, proteins and polynucleotides. In one embodiment, the genes incorporate tissue-specific promoters, controllable promoters, promoters that may be silenced by specific CODN's and may constitute two- and three-unit systems for gene expression, control and DNA transposition (i.e. insertion, excision and targeting of transgenes and other DNA molecules).

In another embodiment, the present invention provides for use of the polymers in vitro or in vivo, in isolated cells or intact animals in which specific blockade of transcription factors or delivery of DNA or other biological effector is desirable. In one embodiment, this includes use as a research tool, including studies of specific genes and studies to identify specific genes regulated by the transcription factors targeted (relates to development of specific CODN and related gene marker mouse lines described below). For clinical use, this would include, but is not limited to delivery of transcription factor decoys (e.g. CODNs) that block transcription factors implicated in disease, response to surgery and/or trauma, developmental defects, aging, toxic exposure, etc.

In another embodiment, the present invention provides for transgenic mice expressing marker genes (lacZ and/or GFP variants) under the control of promoter elements that are primarily controlled by specific transcription factors. In one embodiment, the mice are provided separately or as a kit including specific CODN/polymer complexes and the matching mouse, which serves to identify the cells in which the marker activation (experimentally activated) is blocked by the CODN. In another embodiment, there are transgenic mice with marker genes that are transcriptionally turned on, which can be specifically turned off using CODN/polymer complexes.

In another embodiment, the present invention provides for bi-transgenic (or multiple transgenic) systems designed to utilize the CODN/polymer complexes to regulate gene expression (up, down, on or off) or to mediate gene transposition (insertion, excision or moving in the genome). In one embodiment, transgene A may express a gene of interest under control of a promoter that is inducible by NF-kB or by a yeast or bacterial transcription factor (think tetR or Gal4). In one embodiment, the gene would be on after an NF-kB-inducing stimulus, or constitutively on in a tissue expressing the specific transcription factor (we are making mice for NF-kB activation; mice for gal4 and tetR already exist) and the gene could be turned off by simply providing the CODN/polymer complexes for the specific transcription factor (CODN-OFF). In another embodiment, the animals are continuously delivered CODN/polymer complex and then the CODN/polymer complex is withdrawn to turn the gene on. Other versions could have the gene off, due to expression in the same cells of a transcriptional repressor (has been described for tet), and the repression reversed by adding CODN/polymer complex, allowing expression to turn on (CODN-N).

Another embodiment provides for the delivery of transgenes that may be incorporated into the genome via retroviruses, transposons or retrotransposons. In one embodiment, the delivery is for long-term gene expression or genetic engineering in vitro, in vivo, in isolated cells or in whole animals or in the clinic. In another embodiment, germ cells are targeted using compositions of the present invention to achieve heritable transgenic lines of animals without having to do microinjection (optionally using a bi-transgenic system).

In another embodiment, the present invention provides for using delivery agents for delivery of transcription factor decoys (including, but not limited to NF-kB), to block signaling and gene expression associated with pathogenesis.

In another embodiment, the present invention provides for using polymers for delivery of linear duplications or chains of these decoys (i.e., concatemers), such that each strand contains a number of decoy transcription factor binding sites including more than 1, 2, 3, 4, 5, 6, 7, 8, 9, 10, 15, 20, 25, 30 or more. In another embodiment, the present invention provides for using polymers for delivery of decoys having for multiple transcription factors into one of these strands, such that it can affect blockade of 2, 3, 4, 5, 6, or more transcription factors simultaneously in a cell. In another embodiment, the present invention provides for using polymers for delivery of these strands, or the strands contained in a plasmid or other DNA vector (can include phage, viral or other DNA) to bind to the polymers to deliver the strands to the cytoplasm of the cell, to effect transcription factor blockade.

In an alternate embodiment, the decoy transcription factor binding sites on each strand may be separated via a spacer. A spacer element is generally a nucleic acid, that is to say, it comprises nucleic acid residues. The nucleic acids may be naturally occurring or non-naturally occurring. A spacer may comprise two or more nucleic acids. It may, for example, comprise three or more nucleic acids, for example, four or more, for example, five or more, for example, up to ten nucleic acids or more. The nucleic acids may be the same or different.

The decoys may be any transcription factors, including, but not limited to, NF-kB, AP-1, ATF2, ATF3, SP1 and others. This is all based on the novel concept, supported by data in our lab, that blocking key signaling molecules simultaneously can have additive or even synergistic therapeutic effects, particularly when the molecules chosen are key signaling hubs. In signaling, transcription factors participate by activating or turning down gene expression. In another embodiment, the present invention provides for using CODN's for treatment of MI by blocking NF-kB using decoys to iNOS and Cox2. In another embodiment, the present invention provides for using delivery agents for delivery of decoys to metallothionein and heat shock protein 70.

We are using transcription factor decoys (including, but not limited to the one for NF-kB, disclosed), to block signaling and gene expression associated with pathogenesis. The data that we have pertains to blocking NF-kB in the heart, which we have shown is efficacious in reducing myocardial infarction. However, the concept that we wish to disclose takes this several steps further. First, we are and will use linear duplications or chains of these decoys, such that each strand contains a number of decoy transcription factor binding sites with more than 1, 2, 3, 4, 5, 6, 7, 8, 9, 10, 15, 20, 25, 30, 35, 40 or more copies linked to stabilize the decoy and increases efficacy.

In another embodiment, we incorporate decoys for multiple transcription factors into one of these strands, such that the decoy can affect blockade of 2 or more transcription factors simultaneously in a cell. In another embodiment, we incorporate decoys for multiple transcription factors into one of these strands, such that the decoy can affect blockade of 3 or more transcription factors simultaneously in a cell. Furthermore, the number of sites specific for different factors can be precisely determined so as to precisely control the extent of blockade (there can be simultaneous differential titration of blockade for multiple factors). This is important, since in many diseases and biological processes, the relative amount of activation of multiple signaling pathways controls biological output and disease progression.

Third, we use these strands, or the strands contained in a plasmid or other DNA vector (including, without limitation, phage, viral or other DNA, and these can be concatemers engineered by recombinant DNA techniques) to bind to the polyplexes to deliver the strands to the cytoplasm of the cell, to effect transcription factor blockade.

Preferably, the oligonucleotide decoy inhibits one or more transcription factor. More preferably, the oligonucleotide decoy inhibits NF-kB in addition to one or more transcription factor selected from the group consisting of AP-1, ATF2, ATF3, SP1 and related factors. By blocking key signaling molecules simultaneously has an additive or even synergistic therapeutic effect, particularly when the molecules chosen are key signaling hubs.

In another embodiment, the domains can include decoys to specific promoters, including but not limited to one or more of NF-kB, iNOS, Cox2, metallothionein and heat shock protein 70.

The use of long chains (concatemers) of the binding sites to NF-kB and related genes, the decoy is able to bind much more NF-kB or related molecules per molecule and to effect binding to the polymers. Furthermore, one can deliver much more of the decoy with relatively less of the polymer, which may have specific advantages, including reduced side effects of the polymer.

Generally, the term "oligonucleotide," refers to a short length of single-stranded polynucleotide chain. Oligonucleotides are typically less than 100 residues long (e.g., between 15 and 50), however, as used herein, the term is also intended to encompass longer polynucleotide chains. Oligonucleotides are often referred to by their length. For example a 22 residue oligonucleotide is referred to as a "22-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the term "transcription factor" refers to proteins that interact with one another and RNA polymerase enzyme to modulate transcription. Transcription factors target genes by recognizing specific DNA regulatory sequences (e.g., promoters and enhancers) or other transcription factors. Transcription factors are often referred to as "trans-factors" that interact with "cis-elements" (e.g., enhancers) because they are typically produced from genes located distantly (trans) from their sites of regulation (cis). Some transcription factors are biologically active only when bound to another copy of itself (i.e., homodimers linked through "homodimerization domains") or to other transcription factors (i.e., heterodimers linked through "heterodimerization domains"). For most transcription factors, specific and distinct regions of the protein mediate DNA binding (i.e., "tDNA binding domains") and transcriptional activation (i.e., "activation domains").

A "biologically active compound" is a compound having the potential to react with biological components. More particularly, biologically active compounds utilized in this specification are designed to change the natural processes associated with a living cell. For purposes of this specification, a cellular natural process is a process that is associated with a cell before delivery of a biologically active compound. Biologically active compounds may be selected from the group comprising: pharmaceuticals, proteins, peptides, polypeptides, hormones, cytokines, antigens, viruses, oligonucleotides, nucleic acids, and synthetic polymers such as polypyroles could also be delivered.

As used herein, the term "transfection" means the process of delivering a polynucleotide to a cell has been commonly termed transfection or the process of transfecting and also it has been termed transformation. The term transfecting as used herein refers to the introduction of a polynucleotide or other biologically active compound into cells. The polynucleotide may be used for research purposes or to produce a change in a cell that can be therapeutic. The delivery of a polynucleotide for therapeutic purposes is commonly called gene therapy. The delivery of a polynucleotide can lead to modification of the genetic material present in the target cell. The term stable transfection or stably transfected generally refers to the introduction and integration of an exogenous polynucleotide into the genome of the transfected cell. The term stable transfectant refers to a cell which has stably integrated the polynucleotide into the genomic DNA. Stable transfection can also be obtained by using episomal vectors that are replicated during the eukaryotic cell division (e.g., plasmid DNA vectors containing a papilloma virus origin of replication, artificial chromosomes). The term transient transfection or transiently transfected refers to the introduction of a polynucleotide into a cell where the polynucleotide does not integrate into the genome of the transfected cell. If the polynucleotide contains an expressible gene, then the expression cassette is subject to the regulatory controls that govern the expression of endogenous genes in the chromosomes. The term transient transfectant refers to a cell which has taken up a polynucleotide but has not integrated the polynucleotide into its genomic DNA.

The term "transfection agent" or "transfection reagent" or "delivery vehicle", is a compound or compounds that bind(s) to or complex(es) with oligonucleotides and polynucleotides, and enhances their entry into cells. Examples of transfection reagents include, but are not limited to, cationic liposomes and lipids, polyamines, calcium phosphate precipitates, histone proteins, polyethylenimine, polylysine, and polyampholyte complexes. Other reagents include cationic proteins like histones and protamines, or synthetic polymers like polylysine, polyarginine, polyornithine, DEAE dextran, polybrene, and polyethylenimine may be effective intracellular in vitro delivery agents. Typically, the transfection reagent has a component with a net positive charge that binds to the oligonucleotide's or polynucleotide's negative charge. For delivery in vivo, complexes made with sub-neutralizing amounts of cationic transfection agent may be preferred. Non-viral vectors is include protein and polymer complexes (polyplexes), lipids and liposomes (lipoplexes), combinations of polymers and lipids (lipopolyplexes), and multilayered and recharged particles. Transfection agents may also condense nucleic acids.

The term "polynucleotide", or "nucleic acid" or "polynucleic acid", is a term of art that refers to a polymer containing at least two nucleotides. Nucleotides are the monomeric units of polynucleotide polymers. Polynucleotides with less than 120 monomeric units are often called oligonucleotides. Natural nucleic acids have a deoxyribose- or ribose-phosphate backbone. An artificial or synthetic polynucleotide is any polynucleotide that is polymerized in vitro or in a cell free system and contains the same or similar bases but may contain a backbone of a type other than the natural ribose-phosphate backbone. These backbones include: PNAs (peptide nucleic acids), phosphorothioates, phosphorodiamidates, morpholinos, and other variants of the phosphate backbone of native nucleic acids. Bases include purines and pyrimidines, which further include the natural compounds adenine, thymine, guanine, cytosine, uracil, inosine, and natural analogs. Synthetic derivatives of purines and pyrimidines include, but are not limited to, modifications which place new reactive groups such as, but not limited to, amines, alcohols, thiols, carboxylates, and alkylhalides. The term base encompasses any of the known base analogs of DNA and RNA. The term polynucleotide includes deoxyribonucleic acid (DNA) and ribonucleic acid (RNA) and combinations of DNA, RNA and other natural and synthetic nucleotides.

As used herein, the terms "decoy" and "transcription factor decoy" refer to molecules that bind to or interact with transcription factors and prevent their binding to native enhancer and promoter sequences. Decoys include nucleic acid sequences, including, but not limited to, oligonucleotides that correspond to (i.e., are identical to or essentially identical to) the native promoter or enhancer. Such oligonucleotides include, but are not limited to, single stranded palindromic oligonucleotides comprising one or more repeats of the promoter or enhancer sequence, sense and antisense oligonucleotides comprising one or more repeats of the promoter or enhancer sequence, oligonucleotides or other artificial gene products (e.g., mRNAs) that form hairpin structures such that a duplex binding site for the transcription factor is generated, and one or more oligonucleotides that form a cruciform structure such that one or more binding sites for the transcription factor are generated.

As used herein, the term "duplex," in reference to oligonucleotides, refers to regions that are double stranded through hybridization of complementary base pairs. The term "hairpin" refers to double-stranded nucleic acid structures formed by base-pairing between regions of the same strand of a nucleic acid molecule. The regions are arranged inversely and can be adjacent or separated by noncomplementary sequence (i.e., thus forming a loop structure or "stem-loop"). The term "cruciform" refers to structures formed in double-stranded nucleic acids by inverted repeats separated by a short sequence. Cruciform structures can be generated through the hybridization of two or more hairpin structures where the hairpin duplex and loop comprise the short sequence separating the inverted repeats. Cruciform structures can comprise one or more nucleic acid molecules.

In an alternate embodiment, the polynucleotide decoys of the invention comprise an internal oligonucleotide (I) having a length of X bases, where X is a number from about 10 to about 40, preferably 12 to 25, most preferably 14 to 20. The size of the I segments is bounded on the lower end by their ability to maintain the relative binding affinity of the larger segments to, for example, transcription factors. The size of the I segments is bounded on the upper end by their ability to remain relatively insensitive to endonucleases. Thus, the length limits of the I segment of a decoy can be determined empirically by one of skill in the art.

In an alternate embodiment, the polynucleotide decoys of the invention further comprise cap or spacer oligonucleotides, having a length of from about 3 to about 24 bases, preferably 4 to 18 base most preferably 6 to 12 bases. Each of the cap or spacer oligonucleotides is comprised of bases that are unable to bind to any other base within the same cap oligonucleotide. Preferably each of the cap or spacer oligonucleotides consists of a single variety of nucleotide comprising a base selected from the group consisting of adenine, cytosine, thymidine, and modified nucleotides thereof.

In an alternate embodiment, the polynucleotide decoys of the invention comprise a formula comprising: (a) an internal oligonucleotide (I) having a length of X bases, where X is a number from about 14 to about 40; (b) a second complementary oligonucleotide ($C_2$) having a length of Z bases, where Z is a number greater than Preferably, the domains (I) are covalently linked to the 5' end of the P1, the 3' end of the P1 is covalently linked to the 5' end of next I, the 3' end of the I is covalently linked to the 5' end of the P2, and the 3' end of the P2 is covalently linked to the 5' end of the next (I). In a specific embodiment, the polynucleotide comprises at least 10, 20, 30, 40, 50, 60, 70, 80, 90, 100, or more domains (I) linked together with spacers. In one embodiment, the polynucleotide comprises at least two different domains (I) throughout the molecule.

The invention also provides for a purified decoy probe comprising a first nucleotide base recognition sequence region, wherein the first region binds to a transcription factor, and an optionally present second nucleotide base recognition sequence region, provided that if the first region is nucleic acid and the second region is present, then the second region is either directly joined to the 5' end of the first region is joined to the 3' end or 5' end of the first region by a non-nucleotide linker, wherein the optionally present second region is present if the first region can be used to produce a functional double-stranded promoter sequence using a complementary oligonucleotide, further provided that if the first region is nucleic acid which can be used to produce the functional double-stranded promoter sequence using the complementary oligonucleotide, then the decoy probe does not have a nucleic acid sequence greater than about 10 nucleotides in length joined directly to the 3' end of the first region and the decoy probe does not have a terminal 3' OH group available to accept a nucleoside triphosphate in a polymerization reaction.

The diseases in which the therapeutic/prophylactic composition of the invention is indicated are NF-κB-associated diseases, that is to say diseases caused by the unwanted activation of genes under control of the transcriptional regulatory factor NF-κB, and among such diseases can be reckoned ischemic diseases, hypoxic conditions, ischemic and pharmacologic preconditioning, surgical trauma, cardiac hypertrophy, cardiomyopathy, heart failure, inflammatory diseases, autoimmune diseases, cancer metastasis and invasion, and cachexia. The ischemic disease includes ischemic diseases of organs (e.g. ischemic heart diseases such as myocardial infarction, acute heart failure, chronic heart failure, etc., ischemic brain diseases such as cerebral infarction, and ischemic lung diseases such as pulmonary infarction), aggravation of the prognosis of organ transplantation or organ surgery (e.g. aggravation of the prognosis of heart transplantation, cardiac surgery, kidney transplantation, renal surgery, liver transplantation, hepatic surgery, bone marrow transplantation, skin grafting, corneal transplantation, and lung transplantation), reperfusion disorders, and post-PTCA restenosis. The inflammatory disease mentioned above includes various inflammatory diseases such as nephritis, hepatitis, arthritis, etc., acute renal failure, chronic renal failure, and arteriosclerosis, among other diseases. The autoimmune disease mentioned above includes but is not limited to rheumatism, multiple sclerosis, and Hashimoto's thyroiditis. Particularly the pharmaceutical composition containing the NF-κB decoy according to the present invention as an active ingredient is very suited for the therapy and prophylaxis of reperfusion disorders in ischemic diseases, aggravation of the prognosis of organ transplantation or organ surgery, post-PTCA restenosis, cancer metastasis and invasion, and cachexia such as weight loss following the onset of a cancer.

The NF-κB decoy that can be used in the present invention may be any compound that specifically antagonizes the NF-κB binding site of the chromosomes and includes but is not limited to nucleic acids and their analogs. As preferred examples of the NF-κB decoy, the present invention may utilize NF-kB decoy comprising one or more copies of oligonucleotides CCTTGAAGGGATTTCCCTCC (SEQ ID NO: 4) and GGAACTTCCCTAAAGGGAGG (SEQ ID NO: 5), preferably, the NF-kB decoy are described as oligonucleotides containing the nucleotide sequence of GGGATTTCCC (SEQ ID NO: 6). Preferably, the NF-kB decoy oligonucleotide is a double-stranded 22 by oligonucleotide (5'-AGTTGAGGGGACTTTCCCAGGC-3') (SEQ ID NO: 7) (Promega).

The oligonucleotides may be DNAs or RNAs, and may contain modified nucleotides and/or pseudonucleotides. Furthermore, those oligonucleotides, variants thereof, or compounds containing any of them may be single-stranded or double-stranded and linear or cyclic. The variants are those involving mutations such as substitution, addition and/or deletion of any part of the above-mentioned sequence, and mean nucleic acids specifically antagonizing the binding site of chromosome to which NF-κB is conjugated. The more preferred NF-κB decoy includes double-stranded oligonucleotides each containing one or a plurality of the above nucleotide sequence and variants thereof. The oligonucleotide which can be used in the present invention includes oligonucleotides modified so as to be less susceptible to biodegradation, such as those oligonucleotides containing the thiophosphoric diester bond available upon substitution of sulfur for the oxygen of the phosphoric diester moiety (S-oligo) and those oligonucleotides available upon substitution of a methyl phosphate group carrying no electric charge for the phosphoric diester moiety.

Regarding to a technology for producing the NF-κB decoy for use in the present invention, the conventional chemical, biochemical, or biological (including recombinant DNA) methods for synthesis can be utilized. When a nucleic acid, for instance, is to be used as the NF-κB decoy, the methods for nucleic acid synthesis which are commonly used in genetic engineering can be employed. For example, the objective decoy oligonucleotide can be directly synthesized on a DNA synthesizer. Or a nucleic acid or its fragments, each synthesized beforehand, can be amplified by PCR or using a cloning vector or the like. Furthermore, the desired nucleic acid can be obtained by such procedures as cleavage with restriction enzymes or the like and/or ligation by means of DNA ligase or the like. In order to obtain a decoy nucleotide which is more stable within cells, the base, sugar or/and phosphoric acid moieties of the nucleic acid may be alkylated, acylated, or otherwise chemically modified, or designed to have a closed circular looped end (i.e. like a dumbbell decoy).

The pharmaceutical composition containing the NF-κB decoy as an active ingredient according to the present invention is not limited in form only if the active ingredient may be taken up by the cells in the affected site or the cells of the target tissue. Thus, the NF-κB decoy, either alone or in admixture with the common pharmaceutical carrier, can be administered orally, parenterally, topically or externally. The pharmaceutical composition may be provided in liquid dosage forms such as solutions, suspensions, syrups, liposomes, lotions, etc. or in solid dosage forms such as tablets, granules, powders, and capsules. Where necessary, those pharmaceutical compositions may be supplemented with various vehicles, excipients, stabilizers, lubricants, and/or other conventional pharmaceutical additives, such as lactose, citric acid, tartaric acid, stearic acid, magnesium stearate, terra alba, sucrose, corn starch, talc, gelatin, agar, pectin, peanut oil, olive oil, caccao butter, ethylene glycol, and so on.

Particularly when a nucleic acid or a modification product thereof is used as the NF-κB decoy, the preferred dosage form includes those which are generally used in gene therapy, such as liposomes inclusive of membrane fusion liposomes utilizing Sendai virus and the like and liposomes utilizing endocytosis, preparations containing cationic lipids such as Lipofectamine (Life Tech Oriental) or virosomes utilizing a retrovirus vector, adenovirus vector, or the like. Particularly preferred are membrane fusion liposomes.

The structure of such a liposomal preparation may be any of a large unilamellar vesicle (LUV), a multi-lamellar vesicle (MLV), and a small unilamellar vesicle (SUV). The approximate size of vesicles may range from 200 to 1000 nm for LUV, from 400 to 3500 nm for MLV, and from 20 to 50 nm for SUV but in the case of a membrane fusion liposomal preparation using Sendai virus, for instance, MLV with a vesicular system of 200-1000 nm in diameter is preferably employed.

There is no limitation on the technology for liposome production only if the decoy can be successfully entrapped in vesicles. Thus, such liposomes can be manufactured by the conventional techniques such as the reversed phase evaporation method (Szoka, F., et al: Biochim. Biophys. Acta, Vol. 601 559 (1980)), ether injection method (Deamer, D. W.: Ann. N.Y. Acad. Sci., Vol. 308 250 (1978)), and surfactant method (Brunner, J., et al: Biochim. Biophys. Acta, Vol. 455 322 (1976)), to name but a few examples.

The lipid that can be used for constructing a liposomal structure includes phospholipids, cholesterol and its derivatives, and nitrogen-containing lipids but phospholipids are generally preferred. The phospholipid that can be used includes naturally-occurring phospholipids such as phosphatidylcholine, phosphatidylserine, phosphatidylglycerol, phosphatidylinositol, phosphatidylethanolamine, phosphatidic acid, cardiolipin, sphingomyelin, egg yolk lecithin, soybean lecithin, lysolecithin, etc., the corresponding phospholipids hydrogenated by the conventional method, and synthetic phospholipids such as dicetyl phosphate, distearoylphosphatidylcholine, dipalmitoylphosphatidylcholine, dipalmitoylphosphatidylethanolamine, dipalmitoylphosphatidylserine, eleostearoylphosphatidylcholine, eleostearoylphosphatidylethanolamine, eleostearoylphosphatidylserine, and so on.

The lipids inclusive of phospholipids can be used each alone or in a suitable combination. By using a lipid containing a positively-charged atomic group such as ethanolamine or choline within the molecule, the binding rate of an electrically negative decoy nucleotide can be enhanced. In addition to the principal phospholipid, various compounds such as cholesterol and its derivatives, stearylamine, -tocopherol, etc., which are known as liposome additives, can be added in the manufacture of liposomes.

To the resulting liposomes can be added a membrane fusion promoter such as Sendai virus, inactivated Sendai virus, a membrane fusion promoting protein purified from Sendai virus, polyethylene glycol, or the like can be added for assisting in the intracellular uptake by the cells at the affected site or of the target tissue.

There is no limitation on the decoy content of the pharmaceutical composition containing the decoy as an active ingredient only if the decoy is contained in amounts effective to control NF-κB-associated diseases. Thus, the decoy content can be liberally selected according to the disease to be controlled, the target site, dosage form, and dosage schedule.

The pharmaceutical composition containing the decoy as an active ingredient as provided in the above manner can be administered by various methods according to the type of disease and the kind of decoy contained. Taking ischemic diseases, inflammatory diseases, autoimmune diseases, cancer metastasis or invasion, and cachexia as examples, the composition can be infused intravascularly, applied directly to the affected area, injected into the lesion, or administered into the regional blood vessel, tissue, or organ in the affected region. As a further specific example, when PTCA is performed for infarction of an organ, the pharmaceutical composition can be administered into the local blood vessel concurrently with the operation or pre- and postoperatively. For organ transplantation, the graft material can be previously treated with the composition of the invention. Furthermore, in the treatment of osteoarthritis or rheumatism, the composition can be directly injected into the joint.

The dosage of the decoy is selected with reference to the patient's age and other factors, type of disease, the kind of decoy used, etc. but for intravascular, intramuscular, or intraarticular administration, for instance, a unit dose of 10-10,000 nmoles can generally be administered once to a few times daily.

As used herein, the term "procedural vascular trauma" includes the effects of surgical/mechanical interventions into mammalian vasculature, but does not include vascular trauma due to the organic vascular pathologies listed hereinabove.

Thus, procedural vascular traumas within the scope of the present treatment method include (1) organ transplantation, such as heart, kidney, liver and the like, e.g., involving vessel anastomosis; (2) vascular surgery, such as coronary bypass surgery, biopsy, heart valve replacement, atheroectomy, thrombectomy, and the like; (3) transcatheter vascular therapies (TVT) including angioplasty, e.g., laser angioplasty and PTCA procedures discussed hereinbelow, employing balloon catheters, and indwelling catheters; (4) vascular grafting using natural or synthetic materials, such as in saphenous vein coronary bypass grafts, dacron and venous grafts used for peripheral arterial reconstruction, etc.; (5) placement of a mechanical shunt, such as a PIFE hemodialysis shunt used for arteriovenous communications; and (6) placement of an intravascular stent, which may be metallic, plastic or a biodegradable polymer. See U.S. patent application Ser. No. 08/389,712, filed Feb. 15, 1995, which is incorporated by reference herein. For a general discussion of implantable devices and biomaterials from which they can be formed, see H. Kambic et al., "Biomatedals in Artificial Organs", Chem. Eng. News. 30 (Apr. 14, 1986), the disclosure of which is incorporated by reference herein.

The present invention generally relates to coronary heart attacks and cardiovascular surgery, and other surgeries with cardiovascular complications. More particularly, the invention is related to the use of oligonucleotide decoy as a protective agent during cardiac and neuronal/brain surgery and during the ischemia/reperfusion phases of acute myocardial infarction (coronary heart attack) or stroke. Also includes instances of peripheral ischemia and hypoxia that occurs as a result of disease, trauma or as a complication of other procedures.

The present invention may be understood more readily by reference to the following detailed description of the preferred embodiments of the invention and the Examples included herein. The NFkB associated polynucleotides and polypeptides are sometimes referred to herein as "NFkB modulatory" polynucleotides and polypeptides. Likewise, all references to "NFkB associated polynucleotides and polypeptides" shall be construed to apply to "NFkB modulatory polynucleotides and polypeptides".

The invention provides the polynucleotide and polypeptide sequences of genes that are believed to be associated with the NF-kB pathway. As referenced herein, members of the NFkB family are transcription factors that are critical regulators of inflammatory and stress responses. Thus, the polynucleotide and polypeptides of the present invention may also be represent critical regulators of inflammatory and stress responses.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide/sequences of the present invention.

In specific embodiments, the polynucleotides of the invention are at least 15, at least 30, at least 50, at least 100, at least 125, at least 500, or at least 1000 continuous nucleotides but are less than or equal to 300 kb, 200 kb, 100 kb, 50 kb, 15 kb, 10 kb, 7.5 kb, 5 kb, 2.5 kb, 2.0 kb, or 1 kb, in length.

In a alternate embodiment, polynucleotides of the invention comprise a portion of the coding sequences, as disclosed herein, but do not comprise all or a portion of any intron. In another embodiment, the polynucleotides further comprise coding sequences coding sequences of a genomic flanking gene (i.e., 5' or 3' to the gene of interest in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

Unless otherwise indicated, all nucleotide sequences determined by sequencing a DNA molecule herein were determined using an automated DNA sequencer (such as the Model 373, preferably a Model 3700, from Applied Biosystems, Inc.), and all amino acid sequences of polypeptides encoded by DNA molecules determined herein were predicted by translation of a DNA sequence determined above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded the sequenced DNA molecule, beginning at the point of such an insertion or deletion. Such point mutations can also change the DNA binding affinity of transcription factors and thus are worthy of consideration in the current invention.

Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37 degree C. in a solution comprising 6.times.SSPE (20.times.SSPE=3M NaCl; 0.2M NaH2PO4; 0.02M EDTA, pH 7.4), 0.5% SDS, 30% formamide, 100 ug/ml salmon sperm blocking DNA; followed by washes at 50 degree C. with 1.times.SSPE, 0.1% SDS. In addition, to achieve even lower stringency, washes performed following stringent hybridization can be done at higher salt concentrations (e.g., 5.times.SSC).

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone generated using oligo dT as a primer).

The polynucleotide of the present invention can be composed of any polyribonucleotide or polydeoxyribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

Methods for introducing the compositions, complexes, nucleic acid molecules and/or vectors of the invention into cells, tissues, organs or organisms as described herein will be familiar to those of ordinary skill in the art. For instance, the compositions, nucleic acid molecules and/or vectors of the invention may be introduced into cells, tissues, organs or organisms using well known techniques of infection, transduction, transfection, and transformation. The compositions, nucleic acid molecules and/or vectors of the invention may be introduced alone or in conjunction with other compositions, nucleic acid molecules and/or vectors. Alternatively, the compositions, nucleic acid molecules and/or vectors of the invention may be introduced into cells, tissues, organs or organisms as a precipitate, such as a calcium phosphate precipitate, or in a complex with a lipid. Electroporation also may be used to introduce the nucleic acid molecules and/or vectors of the invention into a host. Likewise, such molecules may be introduced into chemically competent cells such as E. coli.

The polypeptide of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as post-translational processing, or by chemical modification techniques which are well known in the art. Such modifications are well-described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from post-translation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination.

By "subject" is meant an organism, which is a donor or recipient of explanted cells or the cells themselves. "Subject" also refers to an organism to which the nucleic acid molecules of the invention can be administered. A subject can be a mammal or mammalian cells, including a human or human cells. The term "organism" as referred to herein is meant to encompass any organism referenced herein, though preferably to eukaryotic organisms, more preferably to mammals, including rats and mice, and most preferably to humans.

As used herein the terms "modulate" or "modulates" refer to an increase or decrease in the amount, quality or effect of a particular activity, DNA, RNA, or protein. The definition of "modulate" or "modulates" as used herein is meant to encompass agonists and/or antagonists of a particular activity, DNA, RNA, or protein.

Specifically, the invention provides methods for using the polynucleotides and polypeptides of the invention to identify orthologs, homologs, paralogs, variants, and/or allelic variants of the invention. Also provided are methods of using the polynucleotides and polypeptides of the invention to identify the entire coding region of the invention, non-coding regions of the invention, regulatory sequences of the invention, and secreted, mature, pro-, prepro-, forms of the invention (as applicable).

In preferred embodiments, the invention provides methods for identifying the glycosylation and phosphorylation sites inherent in the polynucleotides and polypeptides of the invention, and the subsequent alteration, deletion, and/or addition of the sites for a number of desirable characteristics which include, but are not limited to, augmentation of protein folding, inhibition of protein aggregation, regulation of intracellular trafficking to organelles, increasing resistance to proteolysis, modulation of protein antigenicity, and mediation of intercellular adhesion.

In further preferred embodiments, methods are provided for evolving the polynucleotides and polypeptides of the present invention using molecular evolution techniques in an effort to create and identify novel variants with desired structural, functional, and/or physical characteristics.

While the NFkB-associated sequences are likely to comprise representatives from a number of protein families and classes (such as GPCRs, transcription factors, ion channels, proteases, nucleases, secreted proteins, nuclear hormone receptors, etc.), their biological activity will likely not be exactly the same as NFkB (e.g., a transcription factor). Rather the NFkB associated polynucleotides and polypeptides of the present invention are believed to represent either direct, or indirect, participating members of the NFkB pathway. Therefore, it is expected that the NFkB associated polynucleotides and polypeptides of the present invention, including agonists, antagonists, or fragments thereof, will be capable of providing at least some of the therapeutic benefits afforded by modulators of NFkB, and potentially NFkB itself, upon administration to a patient in need of treatment. The present invention also encompasses antagonists or agonists of the polynucleotides and polypeptides, including fragments thereof, and their potential utility in modulating NFkB modulators, NF-kB-dependent genes and signaling pathways, and potentially NFkB itself.

Modulating the activity of the NFkB associated genes of the present invention may result in fewer toxicities than the drugs, therapies, or regimens presently known to regulate NF-kappaB itself (due to the specificity inherent in specific embodiments, e.g., concatemers). Such NF-kappaB inhibitors include the following, non-limiting examples: NFkB decoy oligonucleotide-HVJ liposomes complex (Dainippon); gene therapy-based implantation of the I kappa B gene into donor organs ex vivo (Novartis; EP699977); drugs designed to block IkappaBalpha-directed ubiquitination enzymes resulting in more specific suppression of NF-kB activation (Aventis); declopramide (OXIGENE; CAS Registry Number: 891-60-1); IPL-550260 (Inflazyme); IPL-512602 (Inflazyme); KP-392 (Kinetek); R-flurbiprofen (Encore Pharmaceuticals; E-7869, MPC-7869; (1,1'-Biphenyl)-4-acetic acid, 2-fluoro-alpha-methyl; CAS Registry Number: 510449-4); drugs disclosed in U.S. Pat. Nos. 5,561, 161 and 5,340,565 (OXIGENE); dexlipotam (Asta Medica); RIP-3 Rigel (Rigel; Pharmaprojects No. 6135); tyloxapol Discovery (Discovery Laboratories; SuperVent; 4-(1,1,3,3-Tetramethylbutyl)phenol polymer with formaldehyde and oxirane; CAS Registry Number: 25301-02-4); IZP-97001 (Inflazyme); IZP-96005 (Inflazyme); IZP-96002 (Inflazyme); sortac (Inflazyme; IPL-400); BXT-51072 (OXIS; 2H-1,2-Benzoselenazine, 3,4-dihydro-4,4-dimethyl-; CAS Registry Number: 173026-17-0); SP-100030 (Celgene; 2-chloro-N-(3,5-di(trifluoromethyl)phenyl)-4-(trifluoromethyl)pyrimidine-5-carboxamide); IPL-576092 (Inflazyme; Stigmastan-15-one, 22,29-epoxy-3,4,6,7,29-pentahydroxy-, (3alpha,4beta,5alpha, 6alpha,7beta, 14beta,22S); CAS Registry Number: 137571-30-3; U.S. Pat. No. 6,046,185); P54 (Phytopharm); Interleukin-10 (Schering-Plough; SCH 52000; Tenovil; rI-10; rhIL-10; CAS Registry Number: 149824-15-7); and antisense oligonucleotides PLGA/PEG microparticles.

The NFkB associated polynucleotides and polypeptides of the present invention, including agonists, and/or fragments thereof, have uses that include detecting, prognosing, treating, preventing, and/or ameliorating the following diseases and/or disorders, including, but limited to: immune disorders, inflammatory disorders, aberrant apoptosis, hepatic disorders, Hodgkins lymphomas, hematopoietic tumors, hyper-IgM syndromes, hypohydrotic ectodermal dysplasia, X-linked anhidrotic ectodermal dysplasia, Immunodeficiency, al incontinentia pigmenti, viral infections, HIV-1, HTLV-1, hepatitis B, hepatitis C, EBV, influenza, viral replication, host cell survival, and evasion of immune responses, rheumatoid arthritis inflammatory bowel disease, colitis, asthma, atherosclerosis, cachexia, euthyroid sick syndrome, stroke, and EAE.

Alternatively, antagonists and/or fragments of the NFkB associated polynucleotides and polypeptides of the present invention have uses that include detecting, prognosing, treating, preventing, and/or ameliorating the following diseases and/or disorders: immune disorders, inflammatory disorders, aberrant apoptosis, hepatic disorders, Hodgkins lymphomas, hematopoietic tumors, hyper-IgM syndromes, hypohydrotic ectodermal dysplasia, X-linked anhidrotic ectodermal dysplasia, immunodeficiency, al incontinentia pigmenti, viral infections, HIV-1, HTLV-1, hepatitis B, hepatitis C, EBV, influenza, viral replication, host cell survival, and evasion of immune responses, rheumatoid arthritis, inflammatory bowel disease, colitis, asthma, atherosclerosis, cachexia, euthyroid sick syndrome, stroke, ischemia, ischemia/reperfusion, hypoxia, heart disease, ischemic diseases of other organs, including, but not limited to muscle, liver, kidney, the GI tract, cardiac hypertrophy, cardiomyopathy, heart failure, developmental defects of skeletal muscle, cancers of all types and EAE.

In another embodiment, the present invention provides for the use for polymers to deliver a concatemer to a cell as a complex. In another embodiment, the present invention provides for the use for polymers of the present invention to deliver a concatemerized double-stranded oligonucleotide molecules (COPN) for transcription factor decoys. In one embodiment, the concatemers consist of a variable number of end-to-end repeated copies of a short (having at least 5, 10, 15, 20, 25, 30, 40, 45, 50, 75, 100 or more bp) dsDNA containing a sequence or sequences that act as transcription factor decoys.

In another embodiment, the present invention provides for the use of the polymers for covalent addition of targeting peptides, receptor binding peptides/protein domains and antibody fragments that may be used to target the CODN/polymer complexes to a specific cell type; thus the agent can be made organ, tissue and/or cell-type specific.

In another embodiment, the present invention provides for using polyamides for targeting peptides and/or antibodies for specific stress and/or drug induced cellular receptors. In one embodiment, the polyamides target the CODN/polymer complexes to ischemic, inflamed or cancerous tissues.

In another embodiment, the present invention provides for using linker peptides containing the sequence recognized by the TNF-alpha converting enzyme (TACE) or another exopeptidase or endopeptidase in order to allow the agent to deliver the CODN/polymer complexes to the cell and then cleave off the targeting peptide.

In another embodiment, the present invention provides for using the polyamides to deliver intact genes (transgenes), plasmids, RNAi, siRNA, morpholinos or other kinds of RNA, proteins and polynucleotides. In one embodiment, the genes incorporate tissue-specific promoters, controllable promoters, promoters that may be silenced by specific CODN/polymer combinations and may constitute two- and three-unit systems for gene expression, control and DNA transposition (i.e. insertion, excision and targeting of transgenes and other DNA molecules).

In another embodiment, the present invention provides for use of the polyamides in vitro or in vivo, in isolated cells or intact animals in which specific blockade of transcription factors or delivery of DNA or other biological effector is desirable. In one embodiment, this includes use as a research tool, including studies of specific genes and studies to identify specific genes regulated by the transcription factors targeted (relates to development of specific CODN/polymer complexes and related gene marker mouse lines described below). For clinical use, this would include, but is not limited to delivery of transcription factor decoys (e.g. CODNs) that block transcription factors implicated in disease, response to surgery and/or trauma, developmental defects, aging, toxic exposure, etc.

In another embodiment, the present invention provides for transgenic mice expressing marker genes (lacZ and/or GFP variants) under the control of promoter elements that are primarily controlled by specific transcription factors. In one embodiment, the mice are provided separately or as a kit including specific CODN/polymer complexes and the matching mouse, which serves to identify the cells in which the marker activation (experimentally activated) is blocked by the CODN. In another embodiment, there are transgenic mice with marker genes that are transcriptionally turned on, which can be specifically turned off using CODN/polymer complexes.

In another embodiment, the present invention provides for bi-transgenic (or multiple transgenic) systems designed to utilize the CODN/polymer complexes to regulate gene expression (up, down, on or off) or to mediate gene transposition (insertion, excision or moving in the genome). In one embodiment, transgene A may express a gene of interest under control of a promoter that is inducible by NF-kB or by a yeast or bacterial transcription factor (tetR or Gal4). In one embodiment, the gene would be on after an NF-kB-inducing stimulus, or constitutively on in a tissue expressing the specific transcription factor and the gene could be turned off by simply providing the CODN/polymer complex for the specific transcription factor (CODN-OFF). In another embodiment, the animals are continuously delivered CODN/polymer complex and then the CODN/polymer complex is withdrawn to turn the gene on. Other versions could have the gene off, due to expression in the same cells of a transcriptional repressor (has been described for tet), and the repression reversed by adding CODN/polymer complex, allowing expression to turn on (CODN-ON).

In another embodiment, the present invention provides for polymers designed for variable release/biodegradation; which may be selected for quick degradation/release of CODN, others for long half-life (the CODN may be active whether or not it is released by the polymers).

SEQUENCE LISTING

```
<160> NUMBER OF SEQ ID NOS: 7

<210> SEQ ID NO 1
<211> LENGTH: 6
<212> TYPE: DNA
<213> ORGANISM: Unknown
<220> FEATURE:
<223> OTHER INFORMATION: Source is not specified in the application.
      The sequence is given as part of an example in the definition of
      the phrase "random at a position in a preselected sequence."

<400> SEQUENCE: 1 cttagt                                                                   6

<210> SEQ ID NO 2
<211> LENGTH: 6
<212> TYPE: DNA
<213> ORGANISM: Unknown
<220> FEATURE:
<223> OTHER INFORMATION: Source is not specified in the application.
      The sequence is given as part of an example in the definition of
      the phrase "random at a position in a preselected sequence."
<220> FEATURE:
<221> NAME/KEY: misc_feature
<222> LOCATION: (4)..(4)
<223> OTHER INFORMATION: n is randomly selected and can be a, t, c or g.

<400> SEQUENCE: 2 cttngt                                                                   6

<210> SEQ ID NO 3
<211> LENGTH: 10
<212> TYPE: DNA
<213> ORGANISM: Unknown
<220> FEATURE:
<223> OTHER INFORMATION: Known NF-kB binding sequence.
<220> FEATURE:
<221> NAME/KEY: misc_feature
<222> LOCATION: (4)..(4)
<223> OTHER INFORMATION: n is a purine residue
<220> FEATURE:
<221> NAME/KEY: misc_feature
<222> LOCATION: (5)..(6)
<223> OTHER INFORMATION: n is any base
<220> FEATURE:
<221> NAME/KEY: misc_feature
<222> LOCATION: (7)..(8)
<223> OTHER INFORMATION: n is a pyrimidine residue

<400> SEQUENCE: 3 gggnnnnncc                                                              10
```

-continued

```
<210> SEQ ID NO 4
<211> LENGTH: 20
<212> TYPE: DNA
<213> ORGANISM: Unknown
<220> FEATURE:
<223> OTHER INFORMATION: Sequence is given as an example of a suitable
      NF-kB decoy sequence.

<400> SEQUENCE: 4
ccttgaaggg atttccctcc                                                   20

<210> SEQ ID NO 5
<211> LENGTH: 20
<212> TYPE: DNA
<213> ORGANISM: Unknown
<220> FEATURE:
<223> OTHER INFORMATION: Sequence is given as an example of a suitable
      NF-kB decoy sequence.

<400> SEQUENCE: 5
ggaacttccc taaagggagg                                                   20

<210> SEQ ID NO 6
<211> LENGTH: 10
<212> TYPE: DNA
<213> ORGANISM: Unknown
<220> FEATURE:
<223> OTHER INFORMATION: Sequence is given as an example of a suitable
      NF-kB decoy sequence.

<400> SEQUENCE: 6
gggatttccc                                                              10

<210> SEQ ID NO 7
<211> LENGTH: 22
<212> TYPE: DNA
<213> ORGANISM: Unknown
<220> FEATURE:
<223> OTHER INFORMATION: Sequence is given as an example of a suitable
      NF-kB decoy sequence.

<400> SEQUENCE: 7
agttgagggg actttcccag gc                                                22
```

I claim:

1. A transcription factor decoy comprising a concatemerized double-stranded oligonucleotide molecule, wherein the concatemerized double-stranded oligonucleotide molecule is selective for a single target transcription factor and comprises at least 10 repeated copies of a domain, wherein each of said domains comprises a nucleotide sequence that acts as a transcription factor decoy for the transcription factor, wherein each of said domains comprises from about 10 to about 40 nucleotide base pairs, and wherein each of said domains is separated by an identical engineered spacer sequence comprising 10 or more non-naturally occurring nucleic acids.

2. The transcription factor decoy of claim 1, further comprising at least one tissue-specific promoter.

3. The transcription factor decoy of claim 1, wherein the transcription factor decoy is capable of blocking signaling and gene expression associated with pathogenesis.

4. The transcription factor decoy of claim 1, wherein the domain is NF-kB-specific.

5. The transcription factor decoy of claim 1, wherein the transcription factor is selected from NF-kB, AP-1, ATF2, ATF3, and SP1.

6. The transcription factor decoy of claim 1, wherein each domain comprises from about 14 to about 40 nucleotide base pairs.

7. The transcription factor decoy of claim 1, wherein each domain comprises from about 12 to about 25 nucleotide base pairs.

8. The transcription factor decoy of claim 1, wherein the concatemerized double-stranded oligonucleotide molecule comprises at least 15 end-to-end repeated copies of a domain.

9. The transcription factor decoy of claim 1, wherein the concatemerized double-stranded oligonucleotide molecule comprises at least 20 end-to-end repeated copies of a domain.

* * * * *